(12) United States Patent
Lee et al.

(10) Patent No.: US 11,085,019 B2
(45) Date of Patent: Aug. 10, 2021

(54) PRECURSORY REGULATORY CYTOTROPHOBLAST CELLS AND USES THEREOF

(71) Applicant: ACCELERATED BIOSCIENCES CORP., Carlsbad, CA (US)

(72) Inventors: Jau-Nan Lee, Kaohsiung (TW); Yuta Lee, Kaohsiung (TW); Tony Tung-Yin Lee, Yakima, WA (US)

(73) Assignee: ACCELERATED BIOSCIENCES CORP., Carlsbad, CA (US)

( * ) Notice: Subject to any disclaimer, the term of this patent is extended or adjusted under 35 U.S.C. 154(b) by 0 days.

(21) Appl. No.: 16/868,905

(22) Filed: May 7, 2020

(65) Prior Publication Data

US 2020/0354672 A1  Nov. 12, 2020

Related U.S. Application Data

(63) Continuation of application No. PCT/US2020/031509, filed on May 5, 2020.

(60) Provisional application No. 62/843,925, filed on May 6, 2019.

(51) Int. Cl.
| | |
|---|---|
| *C12N 5/073* | (2010.01) |
| *A61K 35/50* | (2015.01) |
| *A61K 35/54* | (2015.01) |
| *A61K 35/12* | (2015.01) |

(52) U.S. Cl.
CPC .......... *C12N 5/0605* (2013.01); *A61K 35/50* (2013.01); *A61K 35/54* (2013.01); *C12N 5/0603* (2013.01); *A61K 2035/122* (2013.01); *C12N 2501/115* (2013.01); *C12N 2501/2306* (2013.01); *C12N 2501/2308* (2013.01); *C12N 2506/025* (2013.01)

(58) Field of Classification Search
CPC .......... C12N 2506/45; C12N 2506/03; C12N 2506/02
See application file for complete search history.

(56) References Cited

U.S. PATENT DOCUMENTS

| | | |
|---|---|---|
| 7,642,091 B2 | 1/2010 | Lee et al. |
| 9,457,053 B2 | 10/2016 | Lee et al. |
| 9,574,173 B2 | 2/2017 | Lee et al. |
| 9,808,490 B2 | 11/2017 | Lee et al. |
| 2008/0213387 A1* | 9/2008 | Moore ............ C12N 5/0606 424/548 |
| 2015/0342577 A1 | 12/2015 | Fleming et al. |
| 2016/0074439 A1 | 3/2016 | Herzberg et al. |

FOREIGN PATENT DOCUMENTS

| | | |
|---|---|---|
| WO | WO-2007047468 A2 | 4/2007 |
| WO | WO-2008100498 A2 | 8/2008 |
| WO | WO-2012083021 A1 | 6/2012 |
| WO | WO-2014031553 A1 | 2/2014 |
| WO | WO-2017160804 A1 | 9/2017 |

OTHER PUBLICATIONS

Li et al., BMP4-directed trophoblast differentiation of human embryonic stem cells is mediated through a ΔNp63+ cytotrophoblast stem cell state. Development, vol. 140 (Oct. 2013) pp. 3965-3976. (Year: 2013).*
Alijotas-Reig, J, Liurba, E., and Gris, J.M. (2014). Potentiating maternal immune tolerance in pregnancy: a new challenging role for regulatory T cells. Placenta 34, 241-248.
Amant, F., Vandenbroucke, T., Verheecke, M., Fumagalli, M., Halaska, M.J, Boere, I., Han, S., Gziri, M.M., Peccatori, F., Rob, L., et al. (2015). Pediatric outcome after maternal cancer diagnosed during pregnancy. N. Engl. J. Med. 373, 1824-1834.
Arck, P.C. and Hecher, A.K. (2013). Fetomaternal immune crosstalk and its consequences for maternal and offspring's health. Nat. Med. 19, 548-556.
Becker, J., Kinast, V., Döring, M., Lipps, C., Duran, V., Spanier, J., Tegtmeyer, P.K., Wirth, D., Cicin-Sain, L., Alcamí, A., et al. (2018). Human monocyte-derived macrophages inhibit HCMV spread independent of classical antiviral cytokines. Virulence 9, 1669-1684.
Bilate, A.M., and Lafaille, J.J. (2012). Induced CD4+Foxp3+ regulatory T cells in immune tolerance. Ann. Rev. Immunol. 30, 733-758.
Carosella, E.D., Rouas-Freissm, N., Tronik-Le Roux, D., Moreau, P., and LeMaoult, J. (2015). Chapter two-HLA-G: immune checkpoint molecule. Adv. Immunol. 127, 33-144.
Carter, A.M., Enders, A.C., and Pijnenborg, R. (2015). The role of invasive trophoblast in implantation and placentation of primates. Philos. Trans. R. Lond. B Biol. Sci. 370(1633), 20140070.
Chen, H., Guo, J., Wang, C., Luo, F., Yu, X., Zhang, W., Li, J., Zhao, D., Xu, D., Gong, Q., et al. (2020). Clinical characteristics and intrauterine vertical transmission potential of COVID-19 infection in nine pregnant women: a retrospective review of medical records. Lancet 395, 809-815.
Choudhury, R.H., Dunk, C.E., Lye, S.J., Aplin, J.D., Harris, L.K., Jones, R.I. (2017). Extravillous trophoblast and endothelial cell crosstalk mediates leukocyte infiltration to the early remodeling decidual spiral arteriole wall. J. Immunol. 198, 4115-4128.
Cory, S., Roberts, A., Colman, P.M., and Adams, J.M. (2016). Targeting BCL-2-like proteins to kill cancer cells. Trend Cancer 2, 443-460.
DaSilva-Arnold, S., James, J.L., Al-Khan, A., Zamudio, S., and Illsley, N.P. (2015). Differentiation of first trimester cytotrophoblast to extravillous trophoblast involves an epithelial-mesenchymal transition. Placenta 36, 1412-1418.
Davies, J.E., Pollheimer, J., Yong, H.E.J., Kokkinos, M.I., Kalionis, B., Knofler, M., and Murthi, P. (2016). Epithelial-mesenchymal transition during extravillous trophoblast differentiation. Cell Adh. Migr. 10, 310-321.

(Continued)

*Primary Examiner* — Kara D Johnson
(74) *Attorney, Agent, or Firm* — Wilson Sonsini Goodrich & Rosati

(57) ABSTRACT

Disclosed herein are precursory regulatory cytotrophoblast cells produced in vitro and compositions thereof. Also disclosed herein are methods of treating a disorder or condition by utilizing the cells disclosed herein.

23 Claims, 34 Drawing Sheets

Specification includes a Sequence Listing.

(56) References Cited

OTHER PUBLICATIONS

De Oliveira, L.G., Lash, G.E., Murry-Dunning, C., Bulmer, J.N., Innes, B.A., Searle, R.F., Sass, N., and Robson, S.C. (2010). Role of interleukin 8 in regulation of extravillous trophoblast cell invasion. Placenta 31, 595-601.

Flores-Romero, H., Landeta, O., Ugate-Uribe, B., Cosentino, K., Garcia-Porras, M., Garcia-Saez, A.J., and Basanez, G. (2019). BFL1 modulates apoptosis at the membrane level through a bifunctional and multimodal mechanism showing key differences with BCLXL. Cell Death & Differentiation 26, 1880-1894.

Gregori, S., Amodio, G., Quattrone, F., and Panina-Bordignon, P. (2015). HLA-G orchestrates the early interaction of human trophoblasts with the maternal niche. Front. Immunol. 6,128.

Gregori, Silvia et al., "HLA-G orchestrates the early interaction of human trophoblasts with the maternal niche", Frontiers in Immunology, Mar. 2015, vol. 6, Article 128, pp. 1-8.

Hanna, J., Goldman-Wohl, D., Hamani, Y., Avraham, I., Greenfield, C., Natanson-Yaron, S., Prus, D., Cohen-Daniel, L., Arnon, T.I., Manaster, I., Gazit, R., et al. (2006). Decidual NK cells regulate key developmental processes at the human fetal-maternal interface. Nat. Med. 12, 1065-1074.

He, N., van Iperen, L., de Jong, D., Szuhai, K., Helmerhorst, F.M., van der Westerlaken, L.A., and Chuva de Sousa Lopes, S.M. (2018). Human extravillous trophoblasts penetrate decidual veins and lymphatics before remodeling spiral arteries during early pregnancy. PLoS One 12(1):e0169849.

He, S., Carman, C.V., Lee. J.H., Lan, B., Kolehler, S., Atia, L., Park, C.Y, Kim JH, Mitchel JA, Park JA, ButlerJP, Lu Q, and Fredberg JJ. (2019). The tumor suppressor p53 can promote collective cellular migration. PLoS One 14(2): e0202065.

Iversen, A.C., Norris, P.S., Ware, C.F., and Benedict, C.A. (2005). Human NK cells inhibit cytomegalovirus replication through a noncytolytic mechanism involving lymphotoxin-dependent induction of IFN-β. J. Immunol. 175, 7568-7574.

Iwai, Y., Hamanishi, J., Chamoto, K., and Honjo, T. (2017). Cancer immunotherapies targeting the PD-1 signaling pathway. J. Biomed. Sci. 24, 26.

Jacquir, A., Dumont,C., Carosella, E.D., Rouas-Freiss, N., and LeMaoult, J. (2020). Cytometry-based analysis of HLA-G functions according to ILT2 expression. Hum. Immunol. Available online Feb. 18, in Press. https://doi.org/10.1016/j.humimm.2020.02.001.

Lagendijk, A.K., and Hogan, B.M. (2015). Chapter Ten—VE-cadherin in vascular-development: a coordinator of cell signaling and tissue morphogenesis. Curr. Topic Devel. Biol. 112, 325-352.

Lash, G.E., Pitman, H., Morgan, H.L., Innes, B.A., Agwu, C.N., and Bulmer, J.B. (2016). Decidual macrophages: key regulators of vascular remodeling in human pregnancy. J. Leukocyte Biol. 100, 315-325.

Latos, P.A., and Hemberger, M. (2016). From the stem of placental tree: trophoblast stem cells and their progeny. Development 143, 3650-3660.

Lee, T.Y., Tsai, C.F., Hsieh, T.H., Chen, J.J., Wang, Y.C., Kao, M.C., Wu, R.M., Singh, S., Tsai, E.M., and Lee, J.N. (2012). Ectopic pregnancy-derived human trophoblastic stem cells regenerate dopaminergic nigrostriatal pathway to treat parkinsonian rats. PLoS One 7(12):e52491.

Evans, J. (2016). Hyper glycosylated hCG: a unique human implantation and invasive factor. Am. J. Reprod. Immunol. 75, 333-340.

Kurowski, A., Molotkov, A., and Soriano, P. (2019). FGFR1 regulates trophectoderm development and facilitates blastocyst implantation. Dev. Biol. 446, 94-101.

Nassiri, F., Cusimano, M.D., Scheithauer, B.W., Rotondo, F., Fazio, A., Yousef, G.M., Syro, L.V., Kovacs, K., and Lloyd, R.V. (2011). Endoglin (CD105): a review of its role in angiogenesis and tumor diagnosis, progressive and therapy. Anticancer Res. 31, 2283-2290.

Okae, H., Toh, H., Sato, T., Hiura, H., Takahashi, S., Shirane, K., Kabayama, Y., Suyama, M., Sasaki, H., and Arima, T. (2018). Derivation of trophoblast stem cells. Cell Stem Cell 22, 50-63.

Phillips, S., Chokshi, S., Riva, A., Evans, A., William, R., and Naoumov, N.V. (2010). CD8+ T cell control of hepatitis B virus replication: direct comparison between cytotytic and noncytolytic functions. J. Immunol. 184, 287-295.

Pollheimer, J., Vondra, S., Baltayeva, J., Beristan, A.G., and Knofler, M. (2018). Regulation of placental extravillous trophoblasts by maternal environment. Front. Immunol. 9, 2579.

Rajagopalan, S., and Long, E.O. (2012). KIR2DL4 (CD158d): an activation receptor for HLA-G. Front. Immunol. 3, 258. DOI: 10.3389/fimmu.2012.00258.

Robson, A., Lash, G.E., Innes, B.A., Zhang, J.Y., Robson, S.C., Bulmer, J.N. (2019). Uterine spiral artery muscle dedifferentiation. Hum. Reprod. 34, 1428-1438.

Sharma, S., Godbole, G., and Modi, D. (2016). Decidual control of trophoblast invasion. Am. J. Reprod. Immunol. 75, 341-350.

Spitalier, P., Cortese, G., Pietropolli, A., Filareto, A., Dolci, S., Klinger, F.G., Giardina, E., Cesare, S.D., Bernardini, L., Lauro, D., et al. (2009). Identification of multipotentcytotrophoblast cells from human first trimester chorionic villi. Cloning and Stem Cells. 11, 535-556.

Sung, B.H., Ketova, T., Hoshino, D., Zijlstra, A., and Weaver, A.M. (2015) Directional cell movement through tissue is controlled by exosome secretion. Nat. Comm. 6, 7164.

Svensson-Arvelind, J., and Emenrudh, J. (2015). The role of macrophages in promoting and maintaining homeostasis at the feto-maternal interface. Am. J. Reprod. Immunol. 74, 100-109.

Tabiasco, J., Rabot, M., Aguerre-Girr, M., El Costa, H., Berrebi, A., Parant, O., Laskarin, G., Juretic, K., Bensussan, A., Rukavina, D.P., et al. (2006). Human decidual NK cells: unique phenotype and functional properties—a review. Placenta 27 (Suppl.), 34-39.

Tilburgs, T., Crespo, A.C., van der Zwan, A., Rybalove, B., Raj, T., Stranger, B., Gardner, L., Moffett, A., and Strominger, J.L. (2015). Human HLA-G+ extravillous trophoblasts: immune-activating cells that interact with decidual leukocytes. Proc. Natl. Acad. Sci. U.S.A 112, 7219-7224.

Tsai, E.M., Wang, Y.C., Lee, T.T.,.Tsai, C.F., Chen, H.S., Lai, F.J., Yokoyama, K.K., Hsieh, T.H., Wu, R.M., and Lee, J.N. (2015). Dynamic Trk and G protein signalings regulate dopaminergic neurodifferentiation in human trophoblast stem cells. PLoS One 10, e0143852.

Vacca, P., Vitale, C., Munari, E., Cassatella, M.A., Mingari, M.C., and Moretta, L. (2018). Human innate lymphoid cells: Their functional and cellular interactions in decidua. Front. Immunol. 9, 1897.

Villa-Morales, M., and Fernandez-Piqueras, J. (2012). Targeting the Fas/FasL signaling parhway in cancer therapy. Expert Opinion on Therapeutic Targets. 16, 85-101.

Wallace, A.E., Fraser, R., and Cartwright, J.E. (2012). Extravillous trophoblast and decidual natural killer cells: a remodelling partnership. Hum. Reprod. Update 18, 458-471.

Wheeler, K.C., Jena, M.K., Pradhan, B.S., Nayak, N., Das, S., Hus, C.D., Wheeler, D.S., Chen, K., and Nayak, N.R. (2018). VEGF may contribute to macrophage recruitment and M2 polarization in the decidua. PLoS One 13(1):e0191040.

Windsperger, K.. Dekan, S., Pils, G., Golletz, V., Kunihs, C., Fiala, G., Kristiansen, M., Knofler, M., and Pollheimer, J. (2017). Extravillous trophoblast invasion of venous as well as lymphatic vessels is altered in idiopathic, recurrent, spontaneous abortions. Hum. Reprod. 32, 1208-1217.

Wu, D., Hong, H., Huang, X., Huang, L., He, Z,. Fang, Q., and Luo, Y. (2016). CXCR2 is decreased in preeclamptic placentas and promotes human trophoblast invasion through the Akt signaling pathway. Placenta 43, 17-25.

Yuri, T., Kinoshita, Y., Emoto, Y., Yoshizawa, K. and Tsubura, A. (2014). Human chorionic gonadotropin suppresses human breast cancer cell growth directly via p53-mediated mitochondrial apoptotic pathway and indirectly via ovarian steroid secretion. Anticancer Res. 34, 1347-1354.

Zhang, J.H., Dunk, C.E., Kwan, M., and Lye, S.J., Jones, R.L., Harris, L.K., and Keating, S. (2017). Human dNK cell function is differentially regulated by extrinsic cellular engagement and intrinsic activating receptors in first and second trimester pregnancy. Cell Mol. Immunol. 14, 203-213.

(56) References Cited

OTHER PUBLICATIONS

Zhao, L., Shao, Q., Zhang, Y., Zhang, L., He, Y., Wang, L., Kong, B., and Qu, X. (2016). Human monocytes undergo functional re-programming during differentiation to dendritic cell mediated by human extravillous trophoblasts. Sci. Rep. 6, 20409.

Cohen et al. "Status of p53 in first-trimester cytotrophoblastic cells" Molecular Human Reproduction, Feb. 2007, vol. 13, No. 2, pp. 111-116.

International Search Report and Written Opinion dated Sep. 30, 2020 for International Application Serial No. PCT/US2020/031509, (15 pages).

Li et al. "BMP4-directed trophoblast differentiation of human embryonic stem cells is mediated through adeltaNp63+ cytotrophoblast stem cell state" Development. Oct. 2013, vol. 140, No. 19, pp. 3965-3976.

Marzusch et al. "Expression of the p53 Tumour Suppressor Gene in Human Placenta: An Immunohistochemical Study" Placenta, Jan. 1995, vol. 16, No. 1, pp. 101-104.

\* cited by examiner

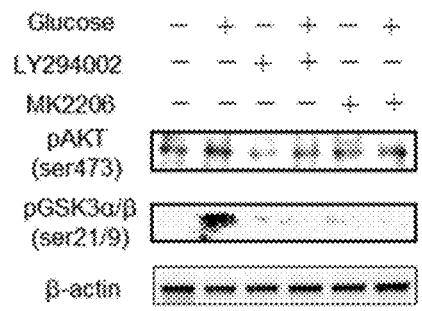
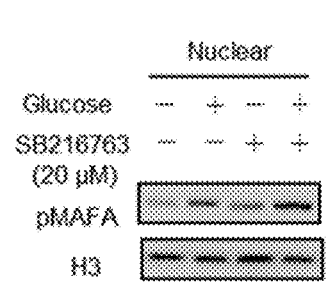
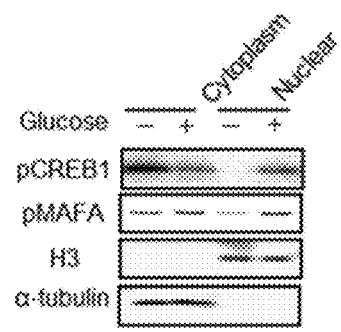
FIG. 2H					FIG. 2I					FIG. 2J
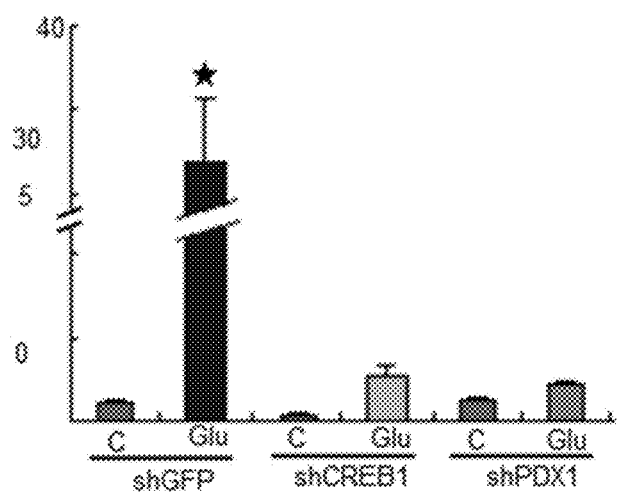
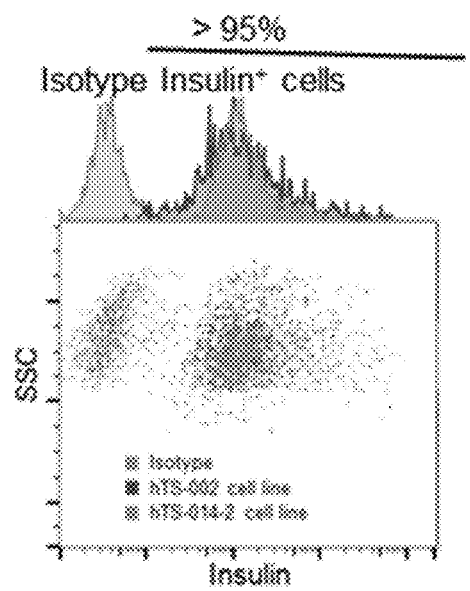
FIG. 2K					FIG. 2L

A. Distribution of CD molecule in hTS cells and prCTBs by flow cytometry.

| Population of CD (%) | hTS cells (n = 8) Mean ± SD | prCTBs (n = 8) Mean ± SD | p-Value* |
|---|---|---|---|
| CD45+ | 0.16 ± 0.10 | 0.06 ± 0.06 | 0.033 |
| CD34+ | 0.83 ± 0.67 | 0.59 ± 0.30 | ns |
| CD3+ | 0.25 ± 0.32 | 0.11 ± 0.20 | ns |
| CD3+ gdTCR+ | 0.03 ± 0.03 | 0.02 ± 0.04 | ns |
| CD4+ | 2.47 ± 3.62 | 3.26 ± 5.71 | ns |
| CD8+ | 5.32 ± 5.62 | 3.44 ± 1.65 | ns |
| CD19+ | 0.17 ± 0.16 | 0.06 ± 0.04 | ns |
| (CD16+56)+ | 21.81 ± 21.48 | 18.58 ± 18.76 | ns |
| CD107a+ | 10.55 ± 5.85 | 7.16 ± 4.33 | ns |

B. Distribution of subtypes of T cells and NK cells detected in hTS cells and prCTBs by flow cytometry.

| Population (%) | hTS cell (n = 8) Mean ± SD | prCTBs (n = 8) Mean ± SD | p-Value* |
|---|---|---|---|
| CD3+(CD16+56)+ | 0.15 ± 0.17 | 0.08 ± 0.14 | ns |
| CD4+(CD16+56)+ | 0.33 ± 0.36 | 0.21 ± 0.18 | ns |
| CD8+(CD16+56)+ | 1.32 ± 2.11 | 0.76 ± 0.93 | ns |
| CD19+(CD16+56)+ | 0.09 ± 0.11 | 0.04 ± 0.02 | ns |
| CD107a+(CD16+56)+ | 3.22 ± 3.29 | 2.15 ± 2.82 | ns |
| CD4+(CD16+56)+CD107a+ | 0.20 ± 0.27 | 0.12 ± 0.13 | ns |
| CD8+(CD16+56)+CD107a+ | 0.84 ± 1.42 | 0.55 ± 0.69 | ns |
| CD19+(CD16+56)+CD107a+ | 0.04 ± 0.04 | 0.04 ± 0.03 | ns |

*: Student t-test, p- value < 0.05 as significant, ns: not significance

FIG. 8

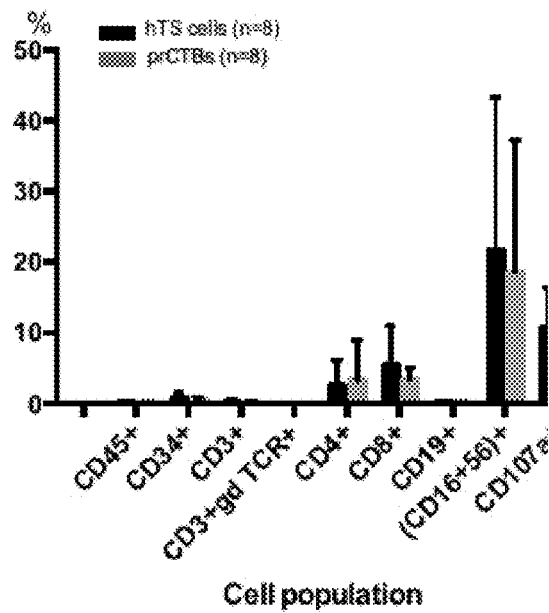
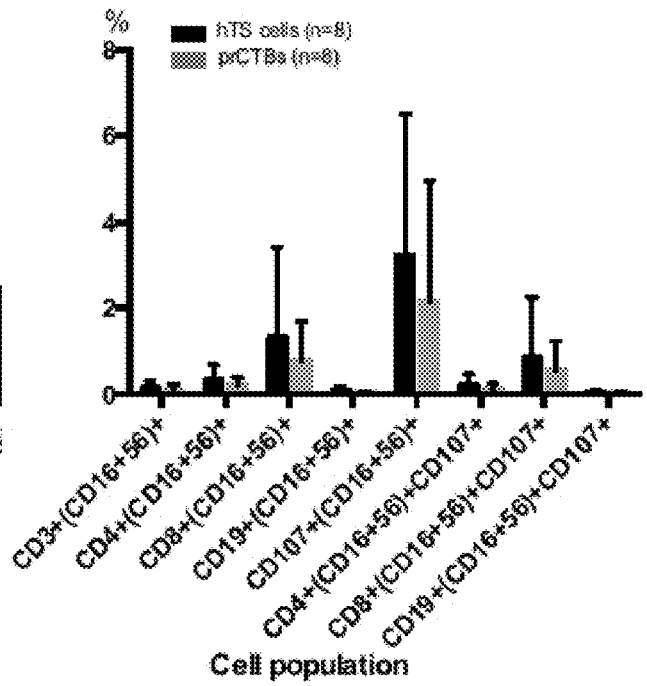
FIG. 9L
FIG. 9M
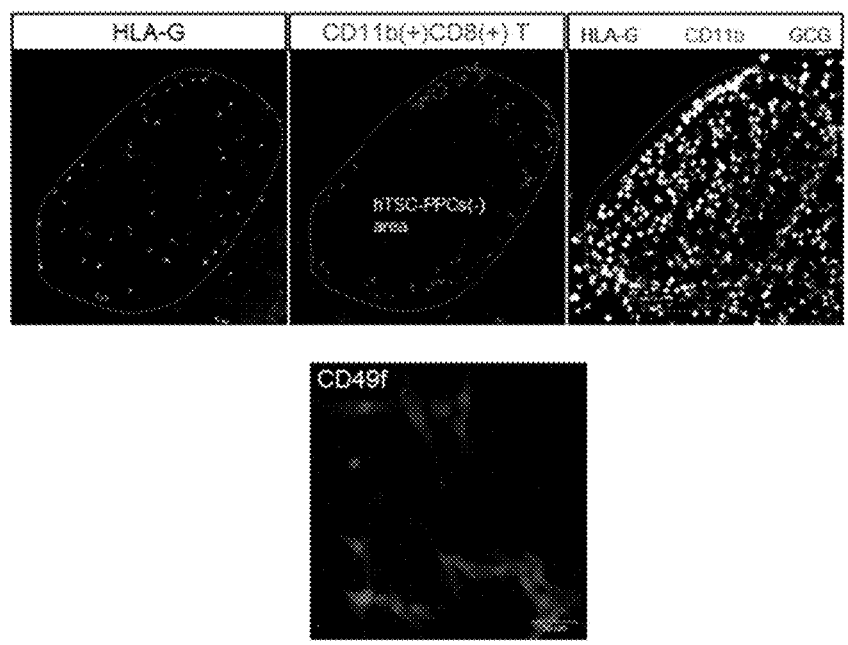
FIG. 9N

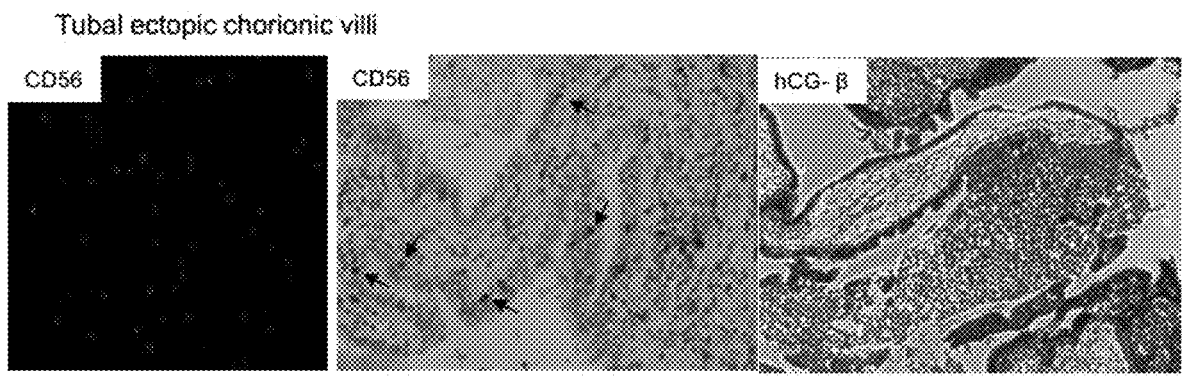
FIG. 12A
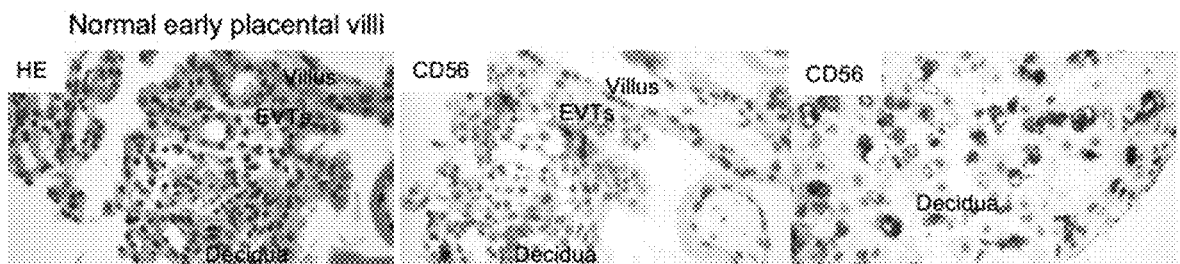
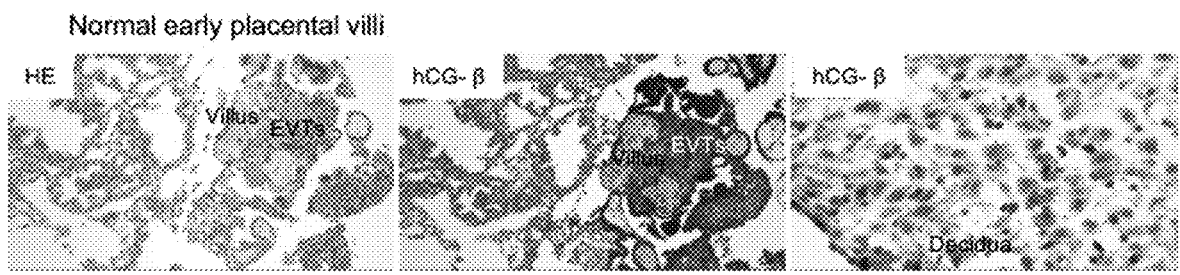
FIG. 12B

```
                         SEQUENCE LISTING

<160> NUMBER OF SEQ ID NOS: 18

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaattataag ctgtttgggt tgttggtct                                        29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaacaattgc ccccataatt tctgactgc                                        29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaattataac tcccaaagtg ctgggatta                                        29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaacaattgc tgcactgttc acaggagga                                        29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaattataac agttgtccca gtgctgcta                                        29

<210> SEQ ID NO 6
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 6
aaacaattga tgacttgccc aaaggtcac                                   29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaattataac ccacaactgg ggtaaaaga                                   29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaacaattgc tgtggaaggg gcaaagata                                   29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctgcggctc tttggtttca                                             20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctgccttca gcacaagagg                                             20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcggctcttt ggtttcaagg                                             20

<210> SEQ ID NO 12
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 12
ctgccttcag cacaagagga                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccgcagttc tcaaggacac                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agaagggagc caggcaagtc                                                 20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttgtagattg ctctctctcc tcc                                             23

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgaagcctt ggctagggg                                                  19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccatcattg attcctggat                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
primer

<400> SEQUENCE: 18
ttgggaggct gagatttgtc                                          20
```

PRECURSORY REGULATORY CYTOTROPHOBLAST CELLS AND USES THEREOF

CROSS-REFERENCE

This application is a continuation of PCT/US2020/031509 filed May 5, 2020, which claims the benefit of U.S. Provisional Patent Application No. 62/843,925, filed May 6, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 31, 2020, is named 44980-705_601_SL.txt and is 4,363 bytes in size.

BACKGROUND

There exists a need for novel stem cell therapies for treating a variety of diseases or conditions, as an alternative to overcome certain shortcomings of existing embryonic stem cells and iPS cells.

Incorporation by Reference

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF SUMMARY

The inventive embodiments provided in this Brief Summary of the Invention are meant to be illustrative only and to provide an overview of selective embodiments disclosed herein. The Brief Summary of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

Disclosed herein, in some aspects, is an isolated precursory regulatory cytotrophoblast (prCTB), wherein: (i) the prCTB expresses beta-hormone human chorionic gonadotropin (β-hCG), human leukocyte antigen G (HLA-G), CD56, insulin, heat shock protein 90 (HSP90), CD4, CD16, CD56, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof; and (ii) the prCTB expresses p53, Ki67, glutamate decarboxylase (GAD65), heat shock protein 70 (HSP70), soluble CD40-ligand (sCD40L), B cell leukemia/lymphoma 2 related protein A1 (BCL2A1 or Bfl-1), myeloid cell leukemia sequence 1 (Mcl-1), or any combination thereof. In some cases, the prCTB expresses CD4, CD16, CD56, CD107a, CD8, or any combination thereof.

Disclosed herein, in some aspects, is an isolated population of cells comprising precursory regulatory cytotrophoblast (prCTBs), wherein: (i) the population of cells express beta-hormone human chorionic gonadotropin (β-hCG), human leukocyte antigen G (HLA-G), CD56, insulin, heat shock protein 90 (HSP90), CD4, CD16, CD56, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof; and (ii) the population of cells express p53, Ki67, glutamate decarboxylase (GAD65), heat shock protein 70 (HSP70), soluble CD40-ligand (sCD40L), B cell leukemia/lymphoma 2 related protein A1 (BCL2A1 or Bfl-1), myeloid cell leukemia sequence 1 (Mcl-1), or any combination thereof.

In some cases, at least about 10% of the population are prCTBs expressing CD16 and CD56. In some cases, at least about 2% of the population are prCTBs expressing CD4. In some cases, at least about 2% of the population are prCTBs expressing CD8. In some cases, at least about 5% of the population are prCTBs expressing CD107.

Disclosed herein, in some aspects, is an isolated population of cells comprising precursory regulatory cytotrophoblast (prCTBs), wherein: (i) at least about 10% of the population are prCTBs expressing CD16 and CD56; (ii) at least about 2% of the population are prCTBs expressing CD4; (iii) at least about 2% of the population are prCTBs expressing CD8; or (iv) at least about 5% of the population are prCTBs expressing CD107, or any combination thereof.

In some cases, (i) at least about 10% of the population are prCTBs expressing CD16 and CD56; (ii) at least about 2% of the population are prCTBs expressing CD4; (iii) at least about 2% of the population are prCTBs expressing CD8; and (iv) at least about 5% of the population are prCTBs expressing CD107. In some cases, the population of cells comprise at least about 2% of the population are prCTBs expressing CD16, CD56, and CD107. In some cases, the prCTB or a plurality of the prCTBs express interleukin 15 (IL-15). In some cases, the prCTB or a plurality of the prCTBs express leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), or any combination thereof. In some cases, the prCTB or a plurality of the prCTBs further express beta-hormone human chorionic gonadotropin (β-hCG), soluble human leukocyte antigen G (sHLA-G), transformation growth factor β1 (TGF-β1), Plasminogen activator inhibitor-1 (PAI-1), interleukin 10 (IL-10), CD105, CD146, or any combination thereof. In some cases, the prCTB or a plurality of the prCTBs lack expression of syncytin, programmed cell death protein 1 (PD-1), or a combination thereof. In some cases, the prCTB or a plurality of the prCTBs secrete a chemokine, a cytokine, a growth factor, or any combination thereof or an exosome carrying a chemokine, a cytokine, a growth factor, or any combination thereof. In some cases, the cytokine comprises chemokine (C-C motif) ligand 5 (CCL5), monocyte chemoattractant protein-1 (MCP-1), monocyte chemoattractant protein-1 (MCP-3), chemokine (C-X-C motif) ligand 1 (CXCL1), chemokine (C-X-C motif) ligand 2 (CXCL2), chemokine (C-C motif) ligand 11 (CCL11), chemokine (C-C motif) ligand 24 (CCL24), chemokine (C-C motif) ligand 26 (CCL26), chemokine (C-C motif) ligand 22 (CCL22), chemokine (C-X-C motif) ligand 10 (CXCL10), fractalkine, and chemokine (C-C motif) ligand 4 (CCL4), or any combination thereof. In some cases, the cytokine comprises interleukin 1α (IL-1α), interleukin 1β (IL-1β), interleukin (IL-2), interleukin 3 (IL-3), interleukin 4 (IL-4), interleukin 6 (IL-6), interleukin 7 (IL-7), interleukin 8 (IL-8), interleukin 10 (IL-10), interleukin 12p40 (IL-12p40), interleukin 13 (IL-13), interleukin 15 (IL-15), or any combination thereof. In some cases, the cytokine comprises interferon α (IFN-α) or interferon γ (IFN-γ). In some cases, the growth factor comprises platelet-derived growth factor homodimer AA (PDGF-AA), PDGF homodimer BB (PDGF-BB), PDGF heterodimer (PDGF-AB), vascular endothelial growth factor (VEGF), granulocyte-macrophage colony-stimulating factor (GM-CSF), epidermal growth factor (EGF), a fibroblast growth factor (FGF) family protein, FMS-like tyrosine kinase 3 ligand (Flt3L), soluble CD40 ligand (sCD40L), tumor necrosis factor α (TNFα), interleukin 1β (IL-1β), or any combination thereof. In some cases, the prCTB or a plurality of the prCTBs have a higher level of activated signal transducer and activator of transcription 3 (STAT3) or transcription factor c-JUN than a progenitor cell from which the isolated prCTB is differentiated in vitro, as measured by immunoblotting. In some cases, the prCTB has a level of activated signal transducer and activator of transcription 3 (STAT3) or transcription factor c-JUN at least about 1.1, 1.2, 1.5, 1.5, 2, 2.2, 2.5, 2.8, 3, 3.5, 4, 5, 8, 10 fold higher than a progenitor cell from which the isolated prCTB is differentiated in vitro, as measured by immunoblotting. In some cases, the prCTB expresses a higher level of SOX2 protein at least about 1.1, 1.2, 1.5, 1.5, 2, 2.2, 2.5, 2.8, 3, 3.5, 4, 5, 8, 10 fold higher than a progenitor cell from which the isolated prCTB is differentiated in vitro, as measured by immunoblotting. In some cases, the isolated prCTB is differentiated in vitro from a chorionic villi-derived progenitor cell that lacks expression of glutamate decarboxylase (GAD65), Ki67, heat shock protein 70 (HSP70), p53, soluble CD40-ligand (sCD40L), or any combination thereof. In some cases, the isolated prCTB is differentiated in vitro from a chorionic villi-derived progenitor cell, and wherein both the chorionic villi-derived progenitor cell and the isolated prCTB express heat shock protein 90 (HSP90). In some cases, the isolated prCTB is a human cell. In some cases, the isolated prCTB is originated from a rodent, rabbit, cow, sheep, pig, dog, cat, monkey, or ape. In some cases, the isolated prCTBs are genetically engineered. In some cases, the isolated prCTBs comprise an exogenous polynucleotide encoding a cellular receptor, an immunological checkpoint protein, a cytokine, or any combination thereof. In some cases, the isolated prCTBs comprise an exogenous polynucleotide encoding a T cell receptor (TCR), a B cell receptor (BCR), a chimeric antigen receptor (CAR), or any combination thereof.

Disclosed herein, in some aspects, is a pharmaceutical composition, comprising: a pharmaceutically acceptable excipient or carrier; and the prCTB or the population of cells as described herein.

Disclosed herein, in some aspects, is a method for treating a disease or condition, comprising administering to a subject in need thereof the prCTB or the population of cells as described herein.

In some cases, the method kills an antigen-bearing target cell. In some cases, the antigen-bearing cell is not an antigen-presenting cell, for example not being a dendritic cell, macrophage, or B cell. In some cases, the antigen-bearing target cell is a cancer cell. In some cases, the cancer cell comprises bladder cancer cell, bone cancer cell, brain cancer cell, breast cancer cell, carcinoma of cervix, colorectal cancer cell, esophageal cancer cell, gastrointestinal cancer cell, hematopoietic malignancy, head and neck squamous cell carcinoma, leukemia, liver cancer cell, lung cancer cell, lymphoma, myeloma, nasal cancer cell, nasopharyngeal cancer cell, oral cancer cell, oropharyngeal cancer cell, ovarian cancer cell, prostate cancer cell, sarcoma, stomach cancer cell, melanoma, thyroid cancer cell, or any combination thereof. In some cases, the antigen-bearing target cell is a pathogen. In some cases, the pathogen comprises virus, bacterium, protozoa, prion, fungus, or any combination thereof. In some cases, the method kills at least about 5%, at least about 10%, at least about 20%, at least about 50%, at least about 80%, at least about 90%, at least about 95%, at least about 99%, or about 100% of a population of antigen-bearing target cells. In some cases, the method downregulates an inflammatory pathway. In some cases, the method treats a disease or condition that comprises transplant rejection, infection, endotoxic shock associated with infection, arthritis, rheumatoid arthritis, psoriatic arthritis, systemic onset juvenile idiopathic arthritis (JIA), inflammatory bowel disease (IBD), systemic lupus erythematosus (SLE), asthma, pelvic inflammatory disease, Alzheimer's disease, Crohn's disease, ulcerative colitis, irritable bowel syndrome, multiple sclerosis, ankylosing spondylitis, dermatomyositis, uveitis, Peyronie's disease, coeliac disease, gallbladder disease, Pilonidal disease, peritonitis, psoriasis, vasculitis, surgical adhesions, stroke, Type I diabetes, Lyme arthritis, meningoencephalitis, immune mediated inflammatory disorders of the central and peripheral nervous system, pancreatitis, trauma from surgery, graft-versus-host disease, heart disease, bone resorption, burns patients, myocardial infarction, Paget's disease, osteoporosis, sepsis, liver or lung fibrosis, periodontitis, or hypochlorhydria. In some cases, the method treats an autoimmune disease. In some cases, method treats Type I diabetes, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, dense deposit disease, inflammatory bowel disease, or psoriasis. In some cases, the method treats Type 1 diabetes. In some cases, the method ameliorates transplant rejection.

Disclosed herein, is a composition, comprising secretomes including an exosome, wherein the secretome comprise or exosome carries a chemokine, a cytokine for example an interleukin, a growth factor, or any combination thereof, and a pharmaceutically or cosmetically acceptable excipient, and wherein the composition is free from a cell.

In some cases, the secretome comprise or exosome carries: (i) a chemokine that comprises CXCL2, MCP-1, Fractalkine, IP-10, MCP-3, Eotaxin, MIP-1β, or any combination thereof; (ii) an interleukin that comprises IL-6, IL-8, IL-4, IL-1RA, IL-10, IL-12P40, IL-15, IL-1α, IL-17A, or any combination thereof; and (iii) a growth factor that comprises PDGF-AA, VEGF, bFGF, G-CSF, Flt-3L, GM-CSF, or any combination thereof. In some cases, the composition comprises MCP-1 and one, two, three, or all of CXCL2, IL-6, IL-8, and VEGF proteins. In some cases, MCP-1 and CXCL2 in the composition have a weight ratio of about 1:1 to about 2:1. In some cases, MCP-1 and CXCL2 in the composition have a weight ratio of about 3:1 to about 4:1. In some cases, MCP-1 and IL-6 in the composition have a weight ratio of from about 2:1 to about 3:1. In some cases, MCP-1 and IL-6 in the composition have a weight ratio of from about 3:1 to about 4:1. In some cases, MCP-1 and IL-8 in the composition have a weight ratio of from about 4:1 to about 6:1. In some cases, MCP-1 and VEGF in the composition have a weight ratio of from about 4:1 to about 6:1. In some cases, MCP-1 and VEGF in the composition have a weight ratio of from about 7:1 to about 9:1. In some cases, the composition further comprises PDGF-AA and wherein MCP-1 and PDGF-AA are present in a weight ratio of from about 3:1 to about 5:1. In some cases, the composition further comprises PDGF-AA and wherein MCP-1 and PDGF-AA are present in a weight ratio of from about 6:1 to about 9:1. In some cases, the composition further comprises PDGF-AA and G-CSF. In some cases, the composition further comprises PDGF-AA and FGF-2 (bFGF). In some cases, the composition further comprises one or more proteins of IP-10, Eotaxin, Flt-3L, GM-CSF, MIP-1a, MIP-1b, IL-1a, IL-1RA, IL-4, IL-7, IL-10, IL-12P40, IL-13, IL-15, IL-17A, CCL5 (RANTES), MDC, MCP-3, IL-12P70, IFNa, IFNr, PDGF-AB/BB, or EGF.

Disclosed herein, in some aspects, is a method for modulating a skin condition, comprising administering to a subject in need thereof the composition as described herein.

In some cases, the method treats a disease or provides a cosmetic application. In some cases, the method tightens skin. In some cases, the method hydrates skin. In some cases, the method rejuvenates skin. In some cases, the composition is free from a stem cell. In some cases, the composition is administered to the subject topically, subcutaneously, percutaneously, intramuscularly, or intratumorally. In some cases, the composition is a dosage form of a lotion, cream, liquid, gel, emulsion, suspension, paste, stick, aerosol, foam, patch, powder, ointment, bead, mask, pad, sheet, wound dressing, bandage, or any combination thereof. In some cases, the subject is a mammal. In some cases, the subject is a primate. In some cases, the subject is a human.

Disclosed herein, in some aspects, is a method of obtaining precursory regulatory cytotrophoblasts (prCTBs), comprising: differentiating pluripotent stem cells in vitro by contacting the stem cells with a fibroblast growth factor and a culture medium comprising nucleosides, L-glutamine, a dipeptide comprising L-glutamine, platelet lysate, or a combination thereof.

In some cases, the culture medium comprises nucleosides, the dipeptide, and platelet lysate. In some cases, the culture medium comprises from about 2 mM to about 200 mM of L-glutamine. In some cases, the contacting lasts for about 24 hours to 48 hours. In some cases, the stem cells are chorionic villi-derived progenitor cells. In some cases, the method comprises culturing the stem cells with the culture medium before contacting them with the fibroblast growth factor to differentiate into the prCTBs. In some cases, the culture medium is free from an antibiotic. In some cases, the antibiotic is penicillin, streptomycin, or any combination thereof. In some cases, the culture medium is free from retinoic acid. In some cases, the culture medium is free from mercaptoethanol, nicotinamide, or a combination thereof. In some cases, the culture medium is free from dexamethasone, recombinant human oncostatin M, BMP4, HGF, or any combination thereof. In some cases, the culture medium is free from an animal component. In some cases, the culture medium is free from a human derived component. In some cases, the culture medium is free from a serum. In some cases, the culture medium is free from fetal bovine serum. In some cases, the fibroblast growth factor is basic fibroblast growth factor (bFGF).

In some aspects, disclosed herein is an isolated precursory regulatory cytotrophoblast (prCTB), wherein: (i) the prCTB expresses beta-hormone human chorionic gonadotropin (β-hCG), human leukocyte antigen G (HLA-G), CD56, insulin, heat shock protein 90 (HSP90), CD4, CD16, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof; and (ii) the prCTB expresses p53, Ki67, glutamate decarboxylase (GAD65), heat shock protein 70 (HSP70), soluble CD40-ligand (sCD40L), B cell leukemia/lymphoma 2 related protein A1 (BCL2A1 or Bfl-1), myeloid cell leukemia sequence 1 (Mcl-1), or any combination thereof. In some instances, the prCTB kills a cancer cell or a pathogen. In some instances, the prCTB induces apoptosis of a cancer cell, e.g., by infiltrating a colony of cancer cells, optionally wherein the prCTB itself does not undergo apoptosis from contacting the cancer cell. In some instances, the cancer cell is a solid tumor cell. In some instances, the cancer cell is a pancreatic cancer cell, a breast cancer cell, liver tumor cell, ovarian tumor cell, lung tumor cell, stomach tumor cell, melanoma cell, or any combination thereof. In some instances, the prCTB downregulates an inflammatory pathway. In some instances, the prCTB expresses CD4, CD16, CD56, CD107a, CD8, or any combination thereof. In some instances, the prCTB lacks expression of syncytin, programmed cell death protein 1 (PD-1), or a combination thereof. In some instances, the prCTB further expresses interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), beta-hormone human chorionic gonadotropin (β-hCG), soluble human leukocyte antigen G (sHLA-G), transformation growth factor β1 (TGF-β1), Plasminogen activator inhibitor-1 (PAI-1), interleukin 6 (IL-6), interleukin 8 (IL-8), interleukin 10 (IL-10), CD105, CD146, or any combination thereof. In some instances, the prCTB is a human cell. In some instances, the prCTB is genetically engineered. In some instances, the genetically engineered prCTB comprises a polynucleotide encoding an exogenous protein comprising a cellular receptor, an immunological checkpoint protein, a cytokine, a T cell receptor (TCR), a B cell receptor (BCR), a chimeric antigen receptor (CAR), or any combination thereof. In some instances, the prCTB secretes a chemokine, a cytokine, a growth factor, or any combination thereof, or an exosome carrying any of the foregoing. In some aspects, disclosed herein is a pharmaceutical composition that comprises the prCTB disclosed herein and a pharmaceutically acceptable excipient. In some aspects, disclosed herein is a method for treating a disease or condition, comprising administering to a subject in need thereof the pharmaceutical composition described herein. In some aspects, disclosed herein is a population of cells that comprise a plurality of prCTBs disclosed herein. In some instances, at least about 10% of the population of the prCTBs express expressing CD16 and CD56. In some instances, at least about 2% of the population of the prCTBs express CD4; at least about 2% of the population of the prCTBs express CD8; at least about 5% of the population of the prCTBs express CD107; or any combination thereof. In some instances, at least about 10% of the population of the prCTBs express expressing CD16 and CD56; at least about 2% of the population of the prCTBs express CD4; at least about 2% of the population of the prCTBs express CD8; and at least about 5% of the population of the prCTBs express CD107. In some instances, at least about 2% of the population of the prCTBs express CD16, CD56, and CD107.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A is a schematic illustration of molecular mechanisms of insulin synthesis and secretion in hTS cells. FIG. 1B shows that CREB1 and MAFA antibodies inhibited insulin (INS) gene transcription by reducing CREB1 and MAFA levels by ChIP-qPCR analysis. Data representing mean±SD, n=5; Input: positive control (as 100%); IgG: negative control. FIG. 1C shows that glucose (Gluc; 20 mM) and sulfonylurea (Gli, gliclazide; 10 μM) promoted insulin secretion in hTS cells (1×106 cells); while VDCC inhibitor nifedipine (Nif; 10 μM) inhibits insulin secretion by RIA in secretomic analysis. Data representing mean±SD, n=3; Student t-test, *p<0.05 as significant compared to control. FIG. 1D shows representative imaging of immunoreactive molecules characterized the biological role in hTS cells. Scale bar as indicated.

FIGS. 2A-2M illustrate Gα$_{q/11}$/PIP2/IP3/IP3R/CaMKII/CREB1 and Gβ/PI3K/AKT/GSK3β/MAFA signaling pathways in insulin-expressing hTS Cells. FIGS. 2A-2C show that in hTS cells, glucose (20 mM) stimulated rapid, transient activation of the sweet taste receptors T1R2/T1R3 at the cell membrane by qPCR analysis (FIG. 2A) to consequently activate G protein signals, including Gα$_{q/11}$ and Gβ (FIG. 2B) in 15 min by blotting analysis (FIG. 2C). This action was inhibited by T1R2/T1R3 inhibitor 2,4-dichlorophenoxyacetic acid (2,4-D; 100 μg) (FIG. 2B). Data representing mean±SD, n=5. Student t-test: *p<0.05 statistical significance. FIGS. 2D-2F illustrate establishment of the Gα$_{q/11}$/PIP2/IP3/IP3R/CaMKII/CREB1 pathway by blotting analysis. Active Gα$_{q/11}$ induced inositol trisphosphate (IP3) to act on its receptor IP3R at the membrane of endoplasmic reticulum (ER) to elevate intracellular calcium levels which consequently activate CaMKII. This action was inhibited by shGα that links Gα$_{q/11}$ and CaMKII molecules. CaMKII then activates downstream CREB1 via phosphorylation (p), further verified by using CaMKII inhibitor KN93. FIGS. 2G-2I depict establishment of the Gβ/PI3K/AKT/GSK3α/β pathway. Active Gβ rapidly induced PI3K/AKT signaling by phosphorylation of AKT (pAKT) at ser473 site and its downstream inhibitory GSK3α/β via phosphorylation at ser21/9 site. These actions were inhibited by PI3K inhibitor LY294002 and AKT inhibitor MK2206. Inhibitory pGSKα/β then promoted pMAFA for nuclear localization, confirmed by its presence in the nucleus, and pMAFA expression was inhibited by GSK3 inhibitor SB216763. FIG. 2J shows that both pCREB1 and pMAFA entered the nucleus evidenced by the nuclear cytoplasmic fractionation. β-actin: loading control; α-tubulin and H3 indicating cytoplasmic and nuclear compartment, respectively. FIG. 2K shows that pre-treatment with CREB1 shRNA, but not PDX1 shRNA, significantly reduced insulin expression in response to glucose stimulation (Glu; 20 mM) in hTS cells by qPCR analysis. C as control, shGFP as positive control. Student t-test; *: p<0.05, n=4. FIG. 2L shows insulin expression in two hTS cell lines with two different anti-insulin antibodies by flow cytometry. Isotype: control. FIG. 2M shows that naïve hTS cells do not express stress proteins or proliferation marker Ki67, but express HSP90 by immunocytochemistry. Scale bar: 50 μm.

FIG. 4A shows hTSCs express TGF-β1 immunocytochemically. FIG. 4B shows that bFGF (10 ng/ml) up-regulated TGF-β1 and vimentin but down-regulated E-cadherin by Western blot assay, while FIG. 4D shows that anti-TGF-β1 antibody neutralized these actions. Data representing Mean±SD, n=3, Student t-test: statistical significance: *p<0.05, **p<0.001. FIG. 4C shows that bFGF (10 ng/ml) up-regulated TGF-β1 and vimentin but down-regulated E-cadherin by immunocytochemistry. FIG. 4E shows that bFGF (10 ng/ml) induced morphological changes of hTSCs after one-day incubation, switching from long and spindle towards shortened and fat in cell shape, while from oval to more round in nucleal shape. FIG. 4F shows confirmation of bFGF-induced FOXA2 activation by which FOXA2 was attenuated at the presence of shRNAs against β-catenin. Cells transfected with shGFP (non-specific shRNA) were used as control and β-actin as loading control.

FIG. 5A shows representative images of immunoreactive molecules associated with insulin expression and oxidative stress proteins in the chorionic villi of tubal ectopic pregnancy (7-8 weeks' gestation). Scale bar: 50 μm. FIG. 5B shows distribution of insulin and stress proteins in the chorionic villi of normal pregnancy (7-8 weeks' gestation) by imaging. Scale bar: 200 μm. FIG. 5C is a schematic illustration of differences of prCTBs and hTS cells in expression of stress proteins and also compared to cells in normal uterine pregnancy in the pathways of trophoblast differentiation.

FIG. 7A shows Luminex analysis of exosomes secreted from hTS cells (dark column on the left) and prCTB cells (light column on the right) in culture media with PLUS (upper panel), and exosomes presented in naive hTS cells (dark column on the left) and naïve prCTBs (light column on the right) after excluding the effect of components in PLUS media used (lower panel). FIG. 7G shows that bFGF activated its receptor FGFR1 and downstream PI3K signal, which was inhibited by FGFR inhibitor PD166866. FIG. 7H shows that PI3K phosphorylated (p) AKT to form PI3K/pAKT signaling, which was inhibited by PI3K shRNA. FIG. 7I shows that pAKT activated its downstream CREB1, which was neutralized by using AKT antibodies, including AKT1 shRNA, AKT2 shRNA, and AKT3 shRNA. FIG. 7J shows that pAKT activated its downstream CREB1 through direct interaction by immunoprecipitation (IP) assay. FIG. 7M shows that IL-6 (10 ng/ml) induced β-hCG via GnRHR and IL-6R, inhibited by GnRHR inhibitor Elagolix sodium and CREB1 inhibitor 666-15. FIG. 7N shows that IL-8 (30 ng/ml) induced CD56 via CXCR2/STAT3 signaling, inhibited by CXCR2 inhibitor SB225002 and STAT3 inhibitor Stattic. FIG. 7Q shows that bFGF induced co-expression of CD4 and Foxp3 in prCTBs immunocytochemically. Bar scale: 50 μm.

FIG. 8 shows two tables listing CD molecules in hTS cells and prCTBs as measured by flow cytometry, and markers of subtypes of T cells and NK cells detected in hTS cells and prCTBs as measured by flow cytometry.

FIGS. 9A to 9N show representative flow cytometric analysis on distribution of CD biomarkers in hTS Cells and prCTBs. FIGS. 9A-9K show FACS plots analysis in a representative sample out of 8 in total, showing undetectable CD3 and CD45 (FIG. 9A), CD34 (FIG. 9B) as well as CD3 and gdTCR (FIG. 9C), however, detectable CD (16+56) and CD107a (FIG. 9D), CD (16+56) (FIG. 9E), detectable CD (16+56) but few CD4 (FIG. 9F), detectable CD (16+56) and CD8 (FIG. 9G), detectable CD (16+56) but no CD19 (FIG. 9H), detectable CD107a but few CD4 (FIG. 9I), detectable CD107a and CD8 (FIG. 9J), and detectable CD107a but no CD19 (FIG. 9K) in hTS cells (left panel) and prCTBs (right panel). FIGS. 9L and 9M show distribution of CD molecules (FIG. 9L) and subtypes of NK cells and T cells (FIG. 9M) in population of hTS cells (black column) and prCTBs (gray column). Data representing mean±SD, n=8 independent samples. FIG. 9N shows expression of CD11b and CD49f in prCTBs by immunostaining.

FIGS. 10A-10D show results of transwell invasion and migration assay. MCP-1 (FIGS. 10A and 10B) and CXCL2 (FIGS. 10C and 10D) significantly induced movement of both hTSCs and prCTBs in a dose- and time-dependent manner. FIG. 10E shows immunohistochemistry in normal chorionic villi of 7-8 gestational weeks, revealing that the invading EVTs expressed immunoreactive p53(+), syncytin, β-hCG, and HLA-G molecules. FIGS. 10F-10G show that CD56(+) prCTBs (brown, upper and middle panels of FIG. 10F) and β-hCG(+) prCTBs (brown, upper pane of FIG. 10G) move towards EVTs for implantation (red arrow). Plenty of CD56 (+) (lower panel of F) and β-hCG(+) prCTBs (middle panel of FIG. 10G) under the decidual epithelium. Replacement of arterial endothelial cells by β-hCG(+) prCTBs in maternal deciduas, suggesting SA remodeling (middle panel of FIG. 10G) and β-hCG(+) prCTBs inside the vessel cavity of decidual vein (Lower panel of FIG. 10G), suggesting the invasion of vein as well. FIGS. 10H-10K show photographs of Invasion and Migration assay. FIGS. 10H-10I show that MCP-1 drove movement of hTSCs ($4\times10^3$ cells/ml) in a dose-dependent manner (FIG. 10H) and in a time-dependent manner (FIG. 10I) in both hTSCs and prCTBs (each $4\times10^3$ cells/ml). FIGS. 10J-10K show that CXCL2 drove movement of hTSCs ($4\times10^3$ cells/ml) in a time-dependent manner (FIG. 10J) and a dose-dependent manner (FIG. 10K) in both hTSCs and prCTBs (each $4\times10^3$ cells/ml). Blue color indicating cell-staining with 0.2% Crystal violet (Sigma-Aldrich; 115940). The number of migrated cells (blue color) is counted by using hemocytometer or flow cytometer. n=3 independent samples in each test.

FIGS. 11A-11D show co-culture of prCTBs (arrowhead) and PANC-1 (arrow) at ratio of 2:1 ($3\times104$ cells/well) in time course showing apoptotic changes of PANC-1 encompassed by prCTBs by light microscope (FIG. 11A). Immunocytochemistry showing interaction of two live cells: prCTBs (blue, CytoCalcein 450 stain) and PANC-1 (red, PKH26 stain) in co-culture (FIG. 11B). Apoptotic PANC-1 (green, apopxin stain, upper) and intact prCTBs (blue, middle) seen by interaction (merge, arrow, lower) (FIG. 11C) 3D fluomicroscopy showing apoptotic PANC-1 (green) and intact prCTB (blue) upon interaction (FIG. 11D). FIG. 11E shows immunocytochemistry revealing that prCTBs expressed PD-L1 (upper, left column) but no PD-1 (lower, left column); while PANC-1 expressed both PD-1 (upper, right column) and PD-L1 (lower, right column). FIG. 11F shows that FasL appeared in prCTBs (upper, left column) but not PANC-1 (lower, right column), while Fas was in both prCTBs (lower, left column) and PANC-1 (upper, right column). Bar scale as indicated. FIGS. 11G-11K show that prCTBs induced apoptosis of solid tumor cells upon interaction. FIG. 11G shows by 3D cell explorer-fluo microscopy that prCTBs (blue) induced apoptosis of breast MCF-7 cells (green) upon interaction (FIG. 11G). FIG. 11H shows that prCTBs expressed PD-L1 but no PD-1 (left column); while PANC-1 expressed both PD-1 and PD-L1 (right column). FIG. 11I shows that prCTBs expressed both FasL and Fas (left column); while PANC-1 expressed both of them (right column). FIG. 11J shows by RT-qPCR analysis that prCTBs significantly upregulated anti-apoptotic Mcl-1 mRNA and Bfl-1 mRNA. Data representing Mean±SD, n=4, Student-t test: statistical significance: *p<0.05, **p<0.01. FIG. 11K shows that prCTBs caused apoptosis (apopxin, green) of Huh7 cells (liver), H1299 cells (lung), MKN45 cells (stomach), PA-1 cells (ovary), and A375 cells (melanoma) upon 24 hr co-culture analyzed by 3D cell explorer-fluo microscopy (Nanolive, Swiss). Bar scale as indicated.

FIGS. 12A-12B show cellular processes of CD56(+) β-hCG (+) cells in migration from EVT to maternal decidua. In tubal ectopic chorionic villi. Left panel: CD56-expressing cells immunocytochemistry. Middle panel: Sporadic distribution of CD56(+) cells among villous stroma, inner layer of villous CTBs (black arrow), and concentrated at the EVT areas. Right panel: Distribution of β-hCG-expressing trophoblasts at the villous surface and EVT areas. In normal placental villi. Left panel: Histological identification of anchoring villi, EVTs, and maternal decidual tissues by H&E stain. Middle panel: Appearance of CD56(+) cells at the EVT areas and nearby decidual tissues. Right panel: Prominent CD56(+) cells appear at maternal decidua. Similar distribution of β-hCG (+) trophoblasts as CD56(+) cells.

DETAILED DESCRIPTION

Figure 1A:
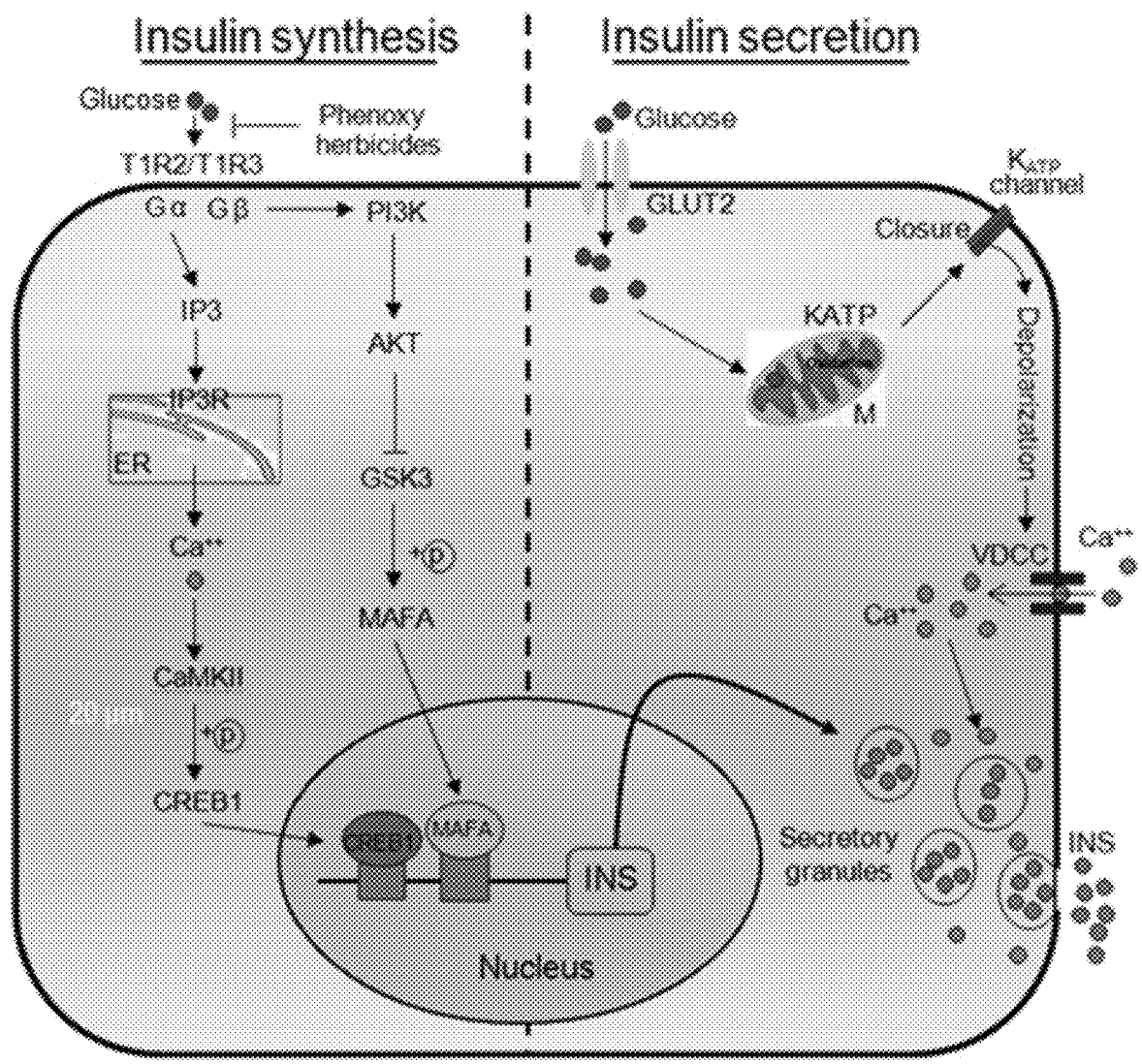
FIGS. 1A-1D show characteristics of insulin expression in human trophoblast stem (hTS) cells.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Disclosed herein are unique precursory regulatory cytotrophoblast cells produced in vitro, compositions thereof, and uses thereof in treating disorders (e.g., cancers, inflammations, or autoimmune diseases) or improving conditions (e.g., skin conditions). The precursory regulatory cytotrophoblast cells are distinct from trophoblast stem cells. The precursory regulatory cytotrophoblast cells are also distinct from embryonic stem cells. The precursory regulatory cytotrophoblast cells are also distinct from primitive cytotrophoblasts and primitive cytotrophoblasts derived cells including villous cytotrophoblasts (villous CTBs), primitive syncytiotrophoblasts (pSTBs), syncytiotrophoblasts (STBs), and extravillous cytotrophoblasts (EVTs), see FIG. 5C. The precursory regulatory cytotrophoblast cells are also distinct from placental cytotrophoblasts. In some instances, precursory regulatory cytotrophoblast cells are not precursor villous cytotrophoblast cells.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range, e.g., ±15% of a referenced numeral value. About also includes the exact amount. Hence "about 5 μL" means "about 5 μL" and also "5 μL." Generally, the term "about" includes an amount that would be expected to be within experimental error.

The terms "treating," "treatment," and the like are used herein to mean obtaining a desired pharmacologic and/or physiologic effect. In some instances, an individual (e.g., an individual suspected to be suffering from and/or genetically pre-disposed to a liver-associated disease or disorder is treated prophylactically with a preparation of cells described herein and such prophylactic treatment completely or partially prevents a liver-associated disease or disorder or sign or symptom thereof. In some instances, an individual is treated therapeutically (e.g., when an individual is suffering from a liver-associated disease or disorder), such therapeutic treatment causes a partial or complete cure for the disease or disorder and/or reverses an adverse effect attributable to the disease or disorder and/or stabilizes the disease or disorder and/or delays progression of the disease or disorder and/or causes regression of the disease or disorder.

Administration (e.g., transplantation) of cells disclosed herein to an area in need of treatment is achieved by, for example and not by way of limitation, local infusion during surgery, by injection, by means of a catheter, or by means of an implant, said implant being of a porous, non-porous, or gelatinous material, including membranes, such as sialastic membranes, or fibers.

"Transplanting" a composition into a mammal refers to introducing the composition into the body of the mammal by any method established in the art. The composition being introduced is the "transplant", and the mammal is the "recipient". The transplant and the recipient can be syngeneic, allogeneic or xenogeneic. Further, the transplantation can be an autologous transplantation.

The term "isolated," when used in relation to a cell or a population of cells, refers to the state of the cell or population of cells being separate from a host organism, from which the cell or the population of cells are derived. In some cases, an isolated cell is in contact with other cells that are isolated from the same host organism. In some cases, an isolated cell is separate from any other cells. In some cases, an isolated prCTB is derived in vitro from a progenitor cell. In some cases, an isolated prCTB is obtained from a host organism and separated from the host organism.

An "effective amount" is an amount of a therapeutic agent sufficient to achieve the intended purpose. An effective amount of a composition to treat or ameliorate a disorder is an amount of the composition sufficient to reduce or remove the symptoms of the disorder.

The section headings used herein are for organizational purposes only and are not to be construed as limiting the subject matter described.

Cells and Compositions

In some cases, disclosed herein is an in vitro isolated precursory regulatory cytotrophoblast (prCTB), wherein the isolated prCTB expresses one or more proteins of: HSP90, insulin, CD4, CD16, CD56, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, B cell leukemia/lymphoma 2 related protein A1 (BCL2A1 or Bfl-1), myeloid cell leukemia sequence 1 (Mcl-1), or any combination thereof; or the prCTB secretes a chemokine, a cytokine, a growth factor, or any combination thereof, or secretes an exosome carrying a chemokine, a cytokine, a growth factor, or any combination thereof; and/or wherein the prCTB expresses p53, Ki67, glutamate decarboxylase (GAD65), heat shock protein 70 (HSP70), soluble CD40-ligand (sCD40L), or any combination thereof. In some instances, the isolated prCTB expresses CD4, CD16, CD56, CD107a, CD8, or any combination thereof. In some instances, the prCTB induces apoptosis of a cancer cell, e.g., by infiltrating a colony of cancer cells, optionally wherein the prCTB itself does not undergo apoptosis from contacting the cancer cell. In some instances, the cancer cell is a solid tumor cell. In some instances, the cancer cell is a pancreatic cancer cell, a breast cancer cell, liver tumor cell, ovarian tumor cell, lung tumor cell, stomach tumor cell, melanoma cell, or any combination thereof. In some instances, the cancer cell expresses PD-1 and PD-L1, while the prCTB expresses PD-L1 but not PD-1. In some instances, the cancer cell expresses Fas but not FasL, while the prCTB expresses Fas and FasL. In some instances, the prCTB expresses Bfl-1 and Mcl-1.

In some cases, disclosed herein is an isolated population of cells comprising precursory regulatory cytotrophoblast (prCTBs), wherein the population of prCTBs express one or more proteins of: HSP90, insulin, CD4, CD16, CD56, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), CD11b, CD49f, CD3, CD19, CD34, or any combination thereof; or the prCTB secretes a chemokine, a cytokine, a growth factor, or any combination thereof, or secretes an exosome carrying a chemokine, a cytokine, a growth factor, or any combination thereof; and/or wherein the population of prCTBs express p53, Ki67, glutamate decarboxylase (GAD65), heat shock protein 70 (HSP70), soluble CD40-ligand (sCD40L), or any combination thereof. In some cases, at least about 10% of the population are prCTBs expressing CD16 and CD56. In some cases, at least about 2% of the population are prCTBs expressing CD4. In some cases, at least about 2% of the population are prCTBs expressing CD8. In some cases, at least about 5% of the population are prCTBs expressing CD107.

In some cases, disclosed herein is and isolated population of cells comprising precursory regulatory cytotrophoblast (prCTBs), wherein: (i) at least about 10% of the population are prCTBs expressing CD16 and CD56; (ii) at least about 2% of the population are prCTBs expressing CD4; (iii) at least about 2% of the population are prCTBs expressing CD8; or (iv) at least about 5% of the population are prCTBs expressing CD107, or any combination thereof. In some cases, disclosed herein is and isolated population of cells comprising precursory regulatory cytotrophoblast (prCTBs), wherein: (i) at least about 10% of the population are prCTBs expressing CD16 and CD56; (ii) at least about 2% of the population are prCTBs expressing CD4; (iii) at least about 2% of the population are prCTBs expressing CD8; and (iv) at least about 5% of the population are prCTBs expressing CD107, or any combination thereof. In some cases, the population of cells comprises at least about 2% of the population are prCTBs expressing CD16, CD56, and CD107.

In some instances, the isolated prCTB expresses interleukin 15 (IL-15). In some instances, the isolated prCTB expresses leukocyte immunoglobulin-like receptor subfamily B member 1 (LILRB1), Leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), CD11b, CD49f, CD3, CD19, CD34, or any combination thereof. In some instances, the isolated prCTB further expresses beta-hormone human chorionic gonadotropin (β-hCG or hCG-β), soluble human leukocyte antigen G (sHLA-G), transformation growth factor β1 (TGF-β1), Plasminogen activator inhibitor-1 (PAI-1), interleukin 10 (IL-10), CD105, CD146, or any combination thereof. In some instances, the isolated prCTB lacks expression of syncytin, programmed cell death protein 1 (PD-1), or a combination thereof. In some instances, the isolated prCTB secretes a chemokine, a cytokine, a growth factor, or any combination thereof, or an exosome carrying a chemokine, a cytokine, a growth factor, or any combination thereof. In some instances, the cytokine comprises chemokine (C-C motif) ligand 5 (CCL5), monocyte chemoattractant protein-1 (MCP-1), monocyte chemoattractant protein-1 (MCP-3), chemokine (C-X-C motif) ligand 1 (CXCL1), chemokine (C-X-C motif) ligand 2 (CXCL2), chemokine (C-C motif) ligand 11 (CCL11), chemokine (C-C motif) ligand 24 (CCL24), chemokine (C-C motif) ligand 26 (CCL26), chemokine (C-C motif) ligand 22 (CCL22), chemokine (C-X-C motif) ligand 10 (CXCL10), fractalkine, and chemokine (C-C motif) ligand 4 (CCL4), or any combination thereof. In some instances, the cytokine comprises interleukin 1α (IL-1α), interleukin 1β (IL-1β), interleukin (IL-2), interleukin 3 (IL-3), interleukin 4 (IL-4), interleukin 6 (IL-6), interleukin 7 (IL-7), interleukin 8 (IL-8), interleukin 10 (IL-10), interleukin 12p40 (IL-12p40), interleukin 13 (IL-13), interleukin 15 (IL-15), or any combination thereof. In some instances, the cytokine comprises interferon α (IFN-α) or interferon γ (IFN-γ). In some instances, the growth factor comprises platelet-derived growth factor homodimer AA (PDGF-AA), PDGF homodimer BB (PDGF-BB), PDGF heterodimer (PDGF-AB), vascular endothelial growth factor (VEGF), granulocyte-macrophage colony-stimulating factor (GM-CSF), epidermal growth factor (EGF), a fibroblast growth factor (FGF) family protein, FMS-like tyrosine kinase 3 ligand (Flt3L), soluble CD40 ligand (sCD40L), tumor necrosis factor α (TNFα), interleukin 1β (IL-1β), or any combination thereof. In some instances, the isolated prCTB has a higher level of activated signal transducer and activator of transcription 3 (STAT3) or transcription factor c-JUN than a progenitor cell from which the isolated prCTB is differentiated in vitro, as measured by immunoblotting. In some instances, the isolated prCTB has a level of activated signal transducer and activator of transcription 3 (STAT3) or transcription factor c-JUN at least about 1.1, 1.2, 1.5, 1.5, 2, 2.2, 2.5, 2.8, 3, 3.5, 4, 5, 8, 10 fold higher than a progenitor cell from which the isolated prCTB is differentiated in vitro, as measured by immunoblotting. In some instances, the isolated prCTB expresses a higher level of SOX2 protein at least about 1.1, 1.2, 1.5, 1.5, 2, 2.2, 2.5, 2.8, 3, 3.5, 4, 5, 8, 10 fold higher than a progenitor cell from which the isolated prCTB is differentiated in vitro, as measured by immunoblotting. In some instances, the chorionic villi-derived progenitor cell lacks expression of glutamate decarboxylase (GAD65), Ki67, heat shock protein 70 (HSP70), p53, soluble CD40-ligand (sCD40L), or any combination thereof. In some instances, both the chorionic villi-derived progenitor cells and the isolated prCTB express heat shock protein 90 (HSP90). In some instances, the isolated prCTB is a human cell. In some instances, the isolated prCTB is originated from a rodent, rabbit, cow, sheep, pig, dog, cat, monkey, or ape. In some instances, the isolated prCTB is present in a pharmaceutical composition that further comprises a pharmaceutically acceptable excipient.

In some cases, the cells provided herein, e.g., prCTBs, are genetically modified. In some cases, the cell is genetically modified to express an exogenous gene, e.g., transgene. The term "transgene" and its grammatical equivalents as used herein can refer to a gene or genetic material that is transferred into an organism. For example, a transgene can be a stretch or segment of DNA containing a gene that is introduced into an organism. When a transgene is transferred into an organism, the organism is then referred to as a transgenic organism. A transgene can retain its ability to produce RNA or polypeptides (e.g., proteins) in a transgenic organism. A transgene can be composed of different nucleic acids, for example RNA or DNA. A transgene may encode for an engineered T cell receptor, for example a TCR transgene. A transgene may comprise a TCR sequence. A transgene can comprise an oncogene. A transgene can comprise an immune oncogene. A transgene can comprise recombination arms. A transgene can comprise engineered sites. In some cases, a transgene is an oncogene. In some cases, a transgene is an immune oncogene. In some cases, a transgene is a tumor suppressor gene. In some cases, a transgene encodes a protein that directly or indirectly promotes proteolysis. In some cases, a transgene is an oncolytic gene. In some cases, a transgene can aid a lymphocyte in targeting a tumor cell. In some cases, a transgene is a T cell enhancer gene. In some cases, a transgene is an oncolytic virus gene. In some cases, a transgene inhibits tumor cell growth. In some cases, a transgene is an anti-cancer receptor. In some cases, a transgene is an anti-angiogenic factor. In some cases, a transgene is a cytotoxic gene. Exemplary transgenes include, but are not limited to, CD28, inducible co-stimulator (ICOS), CD27, 4-1BB (CD137), ICOS-L, CD70, 4-1BBL, Signal 3, a cytokine such as IL-2, IL-7, IL-12, IL-15, IL-21, ICAM-1 (CD54), LFA-3 (CD58), HLA class I genes, B7, CD80, CD83, CD86, CD32, CD64, 4-1BBL, CD3, CD1d, CD2, membrane-bound IL-15, membrane-bound IL-17, membrane-bound IL-21, membrane-bound IL-2, truncated CD19, VEGF, Caspase, a chemokine, or one or more genes encoding an antibody (e.g., a monoclonal antibody) to any of the above, or any combination thereof. In some cases, a transgene encodes a protein involved in cell or tissue repair (e.g., proteins associated with DNA repair, the immune response (e.g., interferons and interleukins), and structural proteins). In some cases, a transgene encodes a growth factor receptor. In some cases, a prCTB as described herein comprises a transgene coding for a TCR, a B cell receptor (BCR), a chimeric antigen receptor (CAR), or any combination thereof. In some instances, the CAR can comprise an antigen recognition domain, a hinge region, a transmembrane domain, and an intracellular signaling domain. In some instances, the antigen recognition domain can be exposed to the outside of the cell and may interact with a potential target molecule. The antigen recognition domain can comprise variable regions of a monoclonal antibody that may be linked as a single chain variable fragment. In some instances, the single chain variable fragment can comprise a variable light chain and a variable heavy chain of an immunoglobin that may be connected with a linker peptide. In some instances, a ligand or receptor system may be used as an alternative to the antibody-based antigen recognition domain. The hinge domain may be designed to combine the transmembrane domain to the antigen recognition domain. In some instances, the hinge region can be a peptide that may be designed to increase the flexibility of the antigen recognition domain. The transmembrane domain can comprise a hydrophobic alpha helix that may span the cell membrane. For example, a CD28 transmembrane domain can be used as the transmembrane domain in the CAR. In some instances, the transmembrane domain can anchor the CAR to the plasma membrane. The intracellular T-cell signaling domain can be connected to the transmembrane domain and may be inside the cell. In some instance, when the target protein binds to the antigen recognition domain, the intracellular signaling domain can transmit an activation signal. In some cases, activation of a signaling domain can comprise phosphorylation of immunoreceptor tyrosine-based activation motif (ITAM). An intracellular signaling domain can comprise a modified ITAM. In some instances, a modified ITAM can comprise a signaling domain, such as a CD3-zeta domain. In some cases, a modified ITAM signaling domain can comprise: CD3-zeta, CD3-epsilon, CD3-gamma, CD3-delta, a derivative thereof, or any combination thereof. In some cases, a intracellular signaling domain may comprise one or more co-stimulatory domains. In some instances, an intracellular signaling domain can comprise one or more signaling domains and one or more co-stimulatory signaling domains. In some instances, a costimulatory domain can comprise a signaling domain from CD28, CD27, CD40, CD134, CD137, inducible costimulatory (ICOS), DAP10, a derivative thereof, or any combination thereof. In some cases, a prCTB as described herein comprises a transgene coding for an oncogene receptor.

In some instances, a composition comprising cells disclosed herein is formulated as a pharmaceutical composition for intravenous administration to a mammal, including a human. In some instances, compositions for intravenous administration are solutions in sterile tonic aqueous buffer. Where necessary, the composition also includes a local anesthetic to ameliorate any pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients are mixed prior to administration.

In one aspect, disclosed herein is a composition (e.g., pharmaceutical composition) comprising a cell disclosed herein. In some instances, the compositions further comprise a pharmaceutically acceptable carrier or excipient. Such a carrier includes, but is not limited to, saline, buffered saline, dextrose, water, and combinations thereof. In other examples, a colloidal dispersion system is used. Colloidal dispersion systems include macromolecule complexes, nanocapsules, microspheres, beads, and lipid-based systems, including oil-in-water emulsions, micelles, mixed micelles, and liposomes.

Secretome and Composition

In some aspects, disclosed herein is a composition comprising a secretome of a trophoblast stem cell or a prCTB as described herein. In some cases, the secretome comprises exosomes secreted by the trophoblast stem cell or the prCTB and other soluble molecules (e.g., proteins, nucleic acids, and lipids) secreted by the trophoblast stem cell or the prCTB.

In some cases, disclosed herein is a composition comprising a chemokine, a cytokine, a growth factor, or any combination thereof. In some instances, the composition comprises an exosome, wherein the exosome carries a chemokine, an interleukin, a growth factor, or any combination thereof, and a pharmaceutically or cosmetically acceptable excipient. In some instances, the composition is free from a cell. In some cases, the composition comprises or exosome carries: (i) a chemokine that comprises CXCL2, MCP-1, Fractalkine, IP-10, MCP-3, Eotaxin, MIP-1β, or any combination thereof; (ii) an interleukin that comprises IL-6, IL-8, IL-4, IL-1RA, IL-10, IL-12P40, IL-15, IL-1α, IL-17A, or any combination thereof; and (iii) a growth factor that comprises PDGF-AA, VEGF, bFGF, G-CSF, Flt-3L, GM-CSF, or any combination thereof.

In some cases, the composition comprises MCP-1 and one, two, three, or all of CXCL2, IL-6, IL-8, and VEGF proteins. In some cases, MCP-1 and CXCL2 in the composition have a weight ratio of about 1:1 to about 2.5:1. For instance, MCP-1 and CXCL2 in the composition have a weight ratio of about: 1.0:1, 1.1:1, 1.2:1, 1.3:1, 1.4:1, 1.5:1, 1.6:1, 1.7:1, 1.8:1, 1.9:1, 2.0:1, 2.1:, 2.2:1, 2.3:1, 2.4:1, or 2.5:1. In some cases, MCP-1 and CXCL2 in the composition have a weight ratio of about 2.0. In some cases, MCP-1 and CXCL2 in the composition have a weight ratio of about 3:1 to about 4:1 or about 3:1 to about 5:1. For instance, MCP-1 and CXCL2 in the composition have a weight ratio of about 3:1, 3.1, 3.2, 3.3, 3.4, 3.5, 3.6, 3.7, 3.8, 3.9, 4.5, 5, or 4.0. In some cases, MCP-1 and CXCL2 in the composition have a weight ratio of about 3.2.

In some cases, the composition comprises MCP-1 and one, two, three, or all of CXCL2, IL-6, IL-8, and VEGF proteins. In some cases, MCP-1 and CXCL2 in the composition have a weight ratio of about 1:7 to about 1:4. For instance, MCP-1 and CXCL2 in the composition have a weight ratio of about 1:7.0, 1:6.8, 1:6.6, 1:6.4, 1:6.2, 1:6, 1:5.8, 1:5.6, 1:5.4, 1:5.2, 1:5.0, 1:4.8, 1:4.6, 1:4.4, 1:4.2, or 1:4.0. In some cases, MCP-1 and CXCL2 in the composition have a weight ratio of about 1:5.0. In some cases, MCP-1 and CXCL2 in the composition have a weight ratio of about 1:4 to about 1:1.5. For instance, MCP-1 and CXCL2 in the composition have a weight ratio of about 1:4.0, 1:3.8, 1:3.6, 1:3.4, 1:3.2, 1:3.0, 1:2.8, 1:2.6, 1:2.4, 1:2.2, 1:2.0, 1; 1.8, 1:1.7, 1:1.6, or 1:1.5. In some cases, MCP-1 and CXCL2 in the composition have a weight ratio of about 1:4 to about 1:2.5.

In some cases, MCP-1 and IL-6 in the composition have a weight ratio of from about 2:1 to about 3:1. For instance, MCP-1 and IL-6 in the composition have a weight ratio of from about 2.0, 2.1, 2.2, 2.3, 2.4, 2.5, 2.6, 2.7, 2.8., 2.9, or 3.0. In some cases, MCP-1 and IL-6 in the composition have a weight ratio of about 2.3. In some cases, MCP-1 and IL-6 in the composition have a weight ratio of about 2.5. In some cases, MCP-1 and IL-6 in the composition have a weight ratio of from about 3:1 to about 4:1. For instance, MCP-1 and IL-6 in the composition have a weight ratio of from about 3.0, 3.1, 3.2, 3.3, 3.4, 3.5, 3.6, 3.7, 3.8., 3.9, or 4.0. In some cases, MCP-1 and IL-6 in the composition have a weight ratio of about 3.6. In some cases, MCP-1 and IL-6 in the composition have a weight ratio of about 3.8.

In some cases, MCP-1 and IL-8 in the composition have a weight ratio of from about 4:1 to about 6:1. For instance, MCP-1 and IL-8 in the composition have a weight ratio of from about: 4.0, 4.1, 4.2, 4.3, 4.4, 4.5, 4.6, 4.7, 4.8., 4.9, 5.0, 5.1, 5.2, 5.3, 5.4, 5.5, 5.6, 5.7, 5.8., 5.9, or 6.0. In some cases, MCP-1 and IL-8 in the composition have a weight ratio of about 4.6. In some cases, MCP-1 and IL-8 in the composition have a weight ratio of about 4.4. In some cases, MCP-1 and IL-8 in the composition have a weight ratio of about 4.9. In some cases, MCP-1 and IL-8 in the composition have a weight ratio of about 4.5.

In some cases, MCP-1 and VEGF in the composition have a weight ratio of from about 5:1 to about 7:1. For instance, MCP-1 and VEGF in the composition have a weight ratio of from about 5.0, 5.1, 5.2, 5.3, 5.4, 5.5, 5.6, 5.7, 5.8., 5.9, 6.0, 6.1, 6.2, 6.3, 6.4, 6.5, 6.6, 6.7, 6.8., 6.9, or 7.0. In some cases, MCP-1 and VEGF in the composition have a weight ratio of about 5.6. In some cases, MCP-1 and VEGF in the composition have a weight ratio of about 6.0. In some cases, MCP-1 and VEGF in the composition have a weight ratio of from about 7:1 to about 9:1. for instance, about 7.0, 7.1, 7.2, 7.3, 7.4, 7.5, 7.6, 7.7, 7.8., 7.9, 8.0, 8.1, 8.2, 8.3, 8.4, 8.5, 8.6, 8.7, 8.8., 8.9, or 9.0. In some cases, MCP-1 and VEGF in the composition have a weight ratio of about 7.6:1. In some cases, MCP-1 and VEGF in the composition have a weight ratio of about 7.3:1.

In some cases, the composition further comprises PDGF-AA. In some cases, MCP-1 and PDGF-AA are present in a weight ratio of from about 3:1 to about 5:1, for instance, about 3.0, 3.1, 3.2, 3.3, 3.4, 3.5, 3.6, 3.7, 3.8., 3.9, 4.0, 4.1, 4.2, 4.3, 4.4, 4.5, 4.6, 4.7, 4.8., 4.9, or 5.0. In some cases, MCP-1 and PDGF-AA are present in a weight ratio of about 3.5. In some cases, MCP-1 and PDGF-AA are present in a weight ratio of from about 6:1 to about 9:1, for instance about 6.0, 6.2, 6.4, 6.6, 6.8, 7.0, 7.2, 7.4, 7.6, 7.8, 8.0, 8.2, 8.4, 8.6, 8.8, or 9.0. In some cases, MCP-1 and PDGF-AA are present in a weight ratio of about 7.8.

In some cases, the composition further comprises PDGF-AA. In some cases, MCP-1 and PDGF-AA are present in a weight ratio of from about 1:2.5 to about 1:1.5, for instance, about 1:2.5, 1:2.4, 1:2.3, 1:2.2, 1:2.1, 1:2.0, 1:1.9, 1:1.8, 1:1.7, 1:1.6, or 1:1.5. In some cases, MCP-1 and PDGF-AA are present in a weight ratio of about 0.6. In some cases, MCP-1 and PDGF-AA are present in a weight ratio of from about 1:1.5 to about 1.5:1, for instance about 1:1.5, 1:1.4, 1:1.3, 1:1.2, 1:1.1, 1:1.0, 1.1:1, 1.2:1, 1.3:1, 1.4:1, or 1.5:1. In some cases, MCP-1 and PDGF-AA are present in a weight ratio of about 1.2.

In some cases, the composition further comprises PDGF-AA. In some cases, MCP-1 and PDGF-AA are present in a weight ratio of from about 3:1 to about 5:1, for instance, about 3.0, 3.1, 3.2, 3.3, 3.4, 3.5, 3.6, 3.7, 3.8., 3.9, 4.0, 4.1, 4.2, 4.3, 4.4, 4.5, 4.6, 4.7, 4.8., 4.9, or 5.0. In some cases, MCP-1 and PDGF-AA are present in a weight ratio of about 3.5. In some cases, MCP-1 and PDGF-AA are present in a weight ratio of from about 6:1 to about 9:1, for instance about 6.0, 6.2, 6.4, 6.6, 6.8, 7.0, 7.2, 7.4, 7.6, 7.8, 8.0, 8.2, 8.4, 8.6, 8.8, or 9.0. In some cases, MCP-1 and PDGF-AA are present in a weight ratio of from about 7.8.

In some cases, the composition further comprises PDGF-AA and G-CSF. In some cases, the composition further comprises PDGF-AA and FGF-2 (bFGF). In some cases, the composition further comprises one or more proteins of IP-10, Eotaxin, Flt-3L, GM-CSF, MIP-1a, MIP-1b, IL-1a, IL-IRA, IL-4, IL-7, IL-10, IL-12P40, IL-13, IL-15, IL-17A, CCL5 (RANTES), MDC, MCP-3, IL-12P70, IFNa, IFNr, PDGF-AB/BB, or EGF.

In some cases, the composition further comprises nucleic acids, such as, mRNA, siRNA, shRNA, or DNA. In some cases, the composition further comprises lipid molecules that are secreted from the prCTB or trophoblast stem cells.

In some cases, a composition disclosed herein can be aseptic. In some cases, the composition can comprise resident microbes. The microbes can be viruses, bacteria, eukaryotic cells or any combination thereof. In some instances, the microbes may not be pathogenic. In some instances, the composition can comprise a bacterium or bacteria at a concentration of less than about: 10 colony forming units (CFU)/gram (g), 50 CFU/g 100 CFU/g, 150 CFU/g, 200 CFU/g, 300 CFU/g, 400 CFU/g, 500 CFU/g, 600 CFU/g, 700 CFU/g, 800 CFU/g, 900 CFU/g, or 1000 CFU/g. In some cases, the composition can comprise bacteria at a concentration of about: 10 CFU/g to about 1000 CFU/g, 10 CFU/g to about 50 CFU/g, 20 CFU/g to about 100 CFU/g, 50 CFU/g to about 200 CFU/g, 100 CFU/g to about 250 CFU/g, 200 CFU/g to about 500 CFU/g, 500 CFU/g to about 700CFU/g, or 600 CFU/g to about 1000 CFU/g. In some instances, the composition may be substantially free (e.g., at least 95% free) or free of: *Staphylococcus aureus, Streptococcus pyogenes, Pseudomonas aeruginosa, Pseudomonas* species, *Klebsiella pneumoniae*, or any combination thereof.

In some cases, a composition disclosed herein may not contain a heavy metal such as lead, bithionol, chlorofluorocarbon propellants, nitrosamines, chloroform, halogenated salicylanilides, hexachlorophene, mercury compounds, 1,4-dioxane, methylene chloride, prohibited cattle materials, sunscreen compounds, vinyl chloride, zirconium-containing complexes, or any combination thereof. In some instances, the prohibited cattle materials can comprise the brain, skull, eyes, trigeminal ganglia, spinal cord, vertebral column, dorsal root ganglia, tonsils, distal ileum of the small intestine or any combination thereof. In some instances, the composition may comprise lead at levels of 10 (parts per million) ppm or less.

In some cases, a composition herein does not comprise a color additive, a fragrance, a paraben, a phthalate, an alcohol, or any combination thereof. In some cases, the color additive, fragrance, paraben, phthalate, or alcohol is present in an insignificant level in the composition, for example less than: 5%, 4%, 3%, 2%, 1%, 0.5%, or 0.1%. In some cases, the incidental ingredient may have no technical/structural, functional or any combination thereof effect in the composition, e.g., no an active ingredient. In some instances, the composition is free from.

In some cases, an excipient disclosed herein can comprise water, glycerol, saline, a vegetable oil (e.g., seed oil), a fruit oil, a flower extract, a mineral oil, a synthetic oil, a sugar compound, a silicate, a calcium salt, a magnesium salt, sodium chloride, potassium chloride, lactic acid, a starch, a sugar alcohol, a cellulose, an activated charcoal, a glycerin, a butter, an amino acid, a paraffin, honey, a wax, beeswax, an agar, calcium carbonate, a citric acid, tartaric acid, a steric acid, xanthan gum, benzoic acid, a polyethylene glycol, a silicon, derivatives thereof, salts thereof, or any combination thereof.

Methods of Use

In some cases, an isolated prCTB is administered to the subject intravenously, subcutaneously, percutaneously, inhalationally, orally, intramuscularly, or intratumorally. In some instances, the subject is a mammal. In some instances, the subject is a primate. In some instances, the subject is a human. In some instances, the isolated prCTB expresses interleukin 15 (IL-15). In some instances, the isolated prCTB expresses CD4, CD16, CD56, CD107a, CD8, or any combination thereof. In some instances, the isolated prCTB expresses leukocyte immunoglobulin-like receptor subfamily B member 1 (LILRB1), Leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof. In some instances, the isolated prCTB further expresses beta-hormone human chorionic gonadotropin (β-hCG), soluble human leukocyte antigen G (sHLA-G), transformation growth factor β1 (TGF-β1), Plasminogen activator inhibitor-1 (PAI-1), interleukin 10 (IL-10), CD105, CD146, or any combination thereof. In some instances, the isolated prCTB lacks expression of syncytin, programmed cell death protein 1 (PD-1), or a combination thereof. In some instances, the isolated prCTB secretes a chemokine, a cytokine, a growth factor, or any combination thereof, or an exosome carrying a chemokine, a cytokine, a growth factor, or any combination thereof. In some instances, the cytokine comprises chemokine (C-C motif) ligand 5 (CCL5), monocyte chemoattractant protein-1 (MCP-1), monocyte chemoattractant protein-1 (MCP-3), chemokine (C-X-C motif) ligand 1 (CXCL1), chemokine (C-X-C motif) ligand 2 (CXCL2), chemokine (C-C motif) ligand 11 (CCL11), chemokine (C-C motif) ligand 24 (CCL24), chemokine (C-C motif) ligand 26 (CCL26), chemokine (C-C motif) ligand 22 (CCL22), chemokine (C-X-C motif) ligand 10 (CXCL10), fractalkine, chemokine (C-C motif) ligand 4 (CCL4), or any combination thereof. In some instances, the cytokine comprises interleukin 1α (IL-1α), interleukin 1β (IL-1β), interleukin (IL-2), interleukin 3 (IL-3), interleukin 4 (IL-4), interleukin 6 (IL-6), interleukin 7 (IL-7), interleukin 8 (IL-8), interleukin 10 (IL-10), interleukin 12p40 (IL-12p40), interleukin 13 (IL-13), interleukin 15 (IL-15), or any combination thereof. In some instances, the cytokine comprises interferon α (IFN-α) or interferon γ (IFN-γ). In some instances, the growth factor comprises platelet-derived growth factor homodimer AA (PDGF-AA), PDGF homodimer BB (PDGF-BB), PDGF heterodimer (PDGF-AB), vascular endothelial growth factor (VEGF), granulocyte-macrophage colony-stimulating factor (GM-CSF), epidermal growth factor (EGF), a fibroblast growth factor (FGF) family protein, FMS-like tyrosine kinase 3 ligand (Flt3L), soluble CD40 ligand (sCD40L), tumor necrosis factor α (TNFα), interleukin 1β (IL-1β), or any combination thereof. In some instances, the isolated prCTB has a higher level of activated signal transducer and activator of transcription 3 (STAT3) or transcription factor c-JUN than a progenitor cell from which the isolated prCTB is differentiated in vitro, as measured by immunoblotting. In some instances, the isolated prCTB has a level of activated signal transducer and activator of transcription 3 (STAT3) or transcription factor c-JUN at least about 1.1, 1.2, 1.5, 1.5, 2, 2.2, 2.5, 2.8, 3, 3.5, 4, 5, 8, 10 fold higher than a progenitor cell from which the isolated prCTB is differentiated in vitro, as measured by immunoblotting. In some instances, the isolated prCTB expresses a higher level of SOX2 protein at least about 1.1, 1.2, 1.5, 1.5, 2, 2.2, 2.5, 2.8, 3, 3.5, 4, 5, 8, 10 fold higher as than a progenitor cell from which the isolated prCTB is differentiated in vitro, as measured by immunoblotting. In some instances, the progenitor cell lacks expression of p53, glutamate decarboxylase (GAD65), Ki67, heat shock protein 70 (HSP70), soluble CD40-ligand (sCD40L), or any combination thereof. In some instances, the isolated prCTB is a human cell. In some instances, the isolated prCTB is originated from a rodent, rabbit, cow, sheep, pig, dog, cat, monkey, or ape.

In some cases, disclosed herein is a method for killing an antigen-bearing target cell, comprising administering to a subject in need thereof a precursory regulatory cytotrophoblast (prCTB), wherein the isolated prCTB expresses one or more proteins that comprises: HSP90, insulin, CD4, CD16, CD56, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), CD11b, CD49f, CD3, CD19, CD34, or any combination thereof; and glutamate decarboxylase (GAD65), Ki67, heat shock protein 70 (HSP70), p53, soluble CD40-ligand (sCD40L), or any combination thereof. In some instances, the antigen-bearing cell is not an antigen-presenting cell, for example not being a dendritic cell, macrophage, or B cell. In some instances, the antigen-bearing target cell is a cancer cell. In some cases, the cancer cell is a solid tumor cell. In some cases, the cancer cell is a blood cancer cell. In some instances, the cancer cell comprises bladder cancer cell, bone cancer cell, brain cancer cell, breast cancer cell, carcinoma of cervix, colorectal cancer cell, esophageal cancer cell, gastrointestinal cancer cell, hematopoietic malignancy, head and neck squamous cell carcinoma, leukemia, liver cancer cell, lung cancer cell, lymphoma, myeloma, nasal cancer cell, nasopharyngeal cancer cell, oral cancer cell, oropharyngeal cancer cell, ovarian cancer cell, prostate cancer cell, sarcoma, stomach cancer cell, melanoma, thyroid cancer cell, or any combination thereof. In some instances, the antigen-bearing target cell is a pathogen. In some instances, the pathogen comprises virus, bacterium, protozoa, prion, fungus, or any combination thereof. In some instances, the method kills at least about 5%, at least about 10%, at least about 20%, at least about 50%, at least about 80%, at least about 90%, at least about 95%, at least about 99%, or about 100% of a population of antigen-bearing target cells.

In some cases, disclosed herein is a method for down-regulating an inflammatory pathway, comprising administering to a subject in need thereof a precursory regulatory cytotrophoblast (prCTB), (i) wherein the isolated prCTB expresses one or more proteins that comprises: (a) HSP90, insulin, CD4, CD16, CD56, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), CD11b, CD49f, CD3, CD19, CD34, or any combination thereof; and (b) glutamate decarboxylase (GAD65), Ki67, heat shock protein 70 (HSP70), p53, soluble CD40-ligand (sCD40L), or any combination thereof, and (ii) wherein the isolated prCTB secretes a chemokine, a cytokine, a growth factor, or any combination thereof, or secretes an exosome carrying a chemokine, a cytokine, a growth factor, or any combination thereof.

In some instances, the method treats a disease or condition that comprises transplant rejection, infection, endotoxic shock associated with infection, arthritis, rheumatoid arthritis, psoriatic arthritis, systemic onset juvenile idiopathic arthritis (JIA), inflammatory bowel disease (IBD), systemic lupus erythematosus (SLE), asthma, pelvic inflammatory disease, Alzheimer's disease, Crohn's disease, ulcerative colitis, irritable bowel syndrome, multiple sclerosis, ankylosing spondylitis, dermatomyositis, uveitis, Peyronie's disease, coeliac disease, gallbladder disease, Pilonidal disease, peritonitis, psoriasis, vasculitis, surgical adhesions, stroke, Type I diabetes, Lyme arthritis, meningoencephalitis, immune mediated inflammatory disorders of the central and peripheral nervous system, pancreatitis, trauma from surgery, graft-versus-host disease, heart disease, bone resorption, burns patients, myocardial infarction, Paget's disease, osteoporosis, sepsis, liver or lung fibrosis, periodontitis, or hypochlorhydria. In some instances, the method treats an autoimmune disease that comprises Type I diabetes, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, dense deposit disease, inflammatory bowel disease, or psoriasis. In some instances, the method treats Type 1 diabetes. In some instances, the method ameliorates transplant rejection.

In some cases, disclosed herein is a method for modulating a skin condition, comprising administering to a subject in need thereof a composition (e.g., a pharmaceutical composition) that comprises a chemokine, a cytokine such as interleukin, a growth factor, or any combination thereof, or an exosome carrying a chemokine, a cytokine such as an interleukin, a growth factor, or any combination thereof. In some cases, the method improves a skin condition, so that the skin condition has one or more better characteristic after the application of the method as compared to before the application of the method. In some instances, the chemokine comprises GRO, MCP-1, Fractalkine, IP-10, MCP-3, Eotaxin, MIP-1β, or any combination thereof. In some instances, the composition comprises an interleukin that comprises IL-6, IL-8 IL-4, IL-1RA, IL-10, IL-12P40, IL-15, IL-1α, IL-17A, or any combination thereof. In some instances, the growth factor comprises PDGF-AA, VEGF, bFGF, G-CSF, Flt-3L, GM-CSF, or any combination thereof. In some instances, the method provides a cosmetic application. In some instances, the method tightens skin. In some instances, the method hydrates skin. In some instances, the method rejuvenates skin. In some instances, the composition is a medium post-passaging a stem cell. In some instances, the stem cell is an isolated precursory regulatory cytotrophoblast (prCTB) described herein. In some instances, a number of the passaging is at least: 1, 2, 3, 4, 5, 6, 7, 8, 9, or 10. In some instances, the stem cell is cultured in the medium for at least about: 1-3 days, such as 1-2 days, for example before collecting the medium. In some instances, the stem cell is cultured in the medium for at least about 12-24 hours, for example before collecting the medium. In some instances, a number of the passaging is 5 to 10. In some instances, the passaging occurs about every 1, 2, or 3 days. In some instances, the passaging occurs about every 2, 4, 6, 8, 12, 16, 20, or 24 hours. In some instances, the medium is free from a stem cell. In some instances, the composition is in a form of a cream, liquid, gel, lotion, mist, capsule, or mask. In some instances, the methods can be used to treat a skin disease. In some instances, the skin disease can be eczema, psoriasis, acne, rosacea, ichthyosis, vitiligo, hives, seborrheic dermatitis, shingles, sunburn, a burn, contact dermatitis, rash, or any combination thereof. In some instances, the method can reduce the appearance of skin aging, photoaging, or any combination thereof. In some instances, the method can reduce the appearance of a scar. In some instances, the method can improve wound healing. In some instances, the method can prevent, reduce or eliminate bruising, benign growths, age spots, cancerous growths, ulcers, infections, or any combination thereof. In some instances, the method can prevent, reduce, or eliminate lines, wrinkles, or any combination thereof of skin. In some instances, the lines or wrinkles can be crow's feet, smile lines, frown lines, forehead furrows, tear troughs, bunny lines, nasolabial folds, marionette lines, mental crease, necklines, age-related wrinkles, crinkle lines, elastotic creases, expression lines, gravitational folds, dynamic wrinkles, static wrinkles, atrophic wrinkles, atrophic crinkling rhytids, or any combination thereof. In some instances, the method can prevent, reduce or eliminate loss of volume, elasticity, or any combination thereof of skin. In some instances, the method can prevent, reduce or eliminate, sagging skin, dull skin tone, mottled discoloration, rough skin, dry skin, itchy skin, thin skin, or any combination thereof. In some cases, the method can improve or ameliorate a skin condition, skin disease or any combination thereof. In some instances, the method can moisturize, tighten, lift, or rejuvenate skin. In some instances, the method can restore or sustain a healthy, smooth, blemish-free, translucent, resilient, or any combination thereof skin. In some cases, the method can heal, treat, remedy or any combination thereof the glycosaminoglycan, the dermis, the collagen and the elastin of skin. In some cases, the improved health of skin can be measured by a wrinkle severity rating scale, a trans-epidermal water loss measurement, a skin color measurement, a skin surface topography measurement, a viscoelastic measurement by a CUTOMETER®, a histological examination, or any combination thereof. In some cases, improved skin health can be measured by a diagnostic image, such as magnetic resonance imaging (MRI). In some cases, measurements can be compared before and after administration of the composition. In some instances, measurements can be compared to a standard.

In another aspect, disclosed herein is a method of treating a condition in a subject, comprising administering to a subject a pharmaceutical composition that comprises a cell herein, in an amount effective for the cells to engraft to the subject (e.g., to the subject's liver). In some instances, the cells are administered in a pharmaceutically acceptable carrier. In some instances, the pharmaceutically acceptable carrier comprises a saline for example a phosphate buffer saline, or fetal bovine serum. In some instances, the cells are administered in a suspension containing about $1\times10^6$ to about $100\times10^6$ cells per ml, about $1\times10^6$ to about $250\times10^6$ cells per ml, about $1\times10^6$ to about $500\times10^6$ cells per ml, or about $10\times10^6$ to about $40\times10^6$ cells per ml. In some instances, the cells are administered in a volume of about: 1-5 ml, 1-10 ml, 1-50 ml, 1-100 ml, or 10-150 ml. In some instances, the subject is a human. In some instances, the administering comprises an injection, e.g., intravenous injection. In some instances, the injection is administered at a hepatic vein. In some instances, the injection is administered at a hepatic artery. In some instances, the condition is a liver-associated disease or disorder. In some instances, the condition is a liver failure. In some instances, the liver-associated disease or disorder comprises alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (optionally, acute fatty liver of pregnancy, intrahepatic cholestasis of pregnancy, preeclampsia, or HELLP Syndrome (hemolysis, elevated liver tests, low platelets)), neonatal hepatitis, primary biliary cirrhosis, primary sclerosing cholangitis, porphyria, Reye's Syndrome, sarcoidosis, toxic hepatitis, type 1 glycogen storage disease, tyrosinemia, viral hepatitis, Wilson disease, or any combination thereof.

Modes of administration of cells disclosed herein include, but are not limited to, systemic intravenous injection and injection directly to the intended site of activity (e.g., endoscopic retrograde injection). The preparation can be administered by any convenient route, for example, by infusion or bolus injection, and can be administered together with other biologically active agents. In some instances, the administration is systemic localized administration.

In some aspects, provided herein are compositions and methods for transplanting cells disclosed herein to subjects. In some instances, the subject is injected by the cells (e.g., intravenously, intramuscularly, transdermally, endoscopic retrograde injection, or intraperitoneally). In some instances, the subject is not treated with an immunosuppressive agent prior to the transplanting. In some instances, the method further comprises treating the patient with an immunosuppressive agent, e.g., FK-506, cyclosporin, or GAD65 antibodies.

In some instances, cells described herein are delivered to a targeted site (e.g., a defect section of the liver) by a delivery system suitable for targeting cells to a particular tissue. For example, the cells are encapsulated in a delivery vehicle that allows for the slow release of the cell(s) at the targeted site. The delivery vehicle is modified such that it is specifically targeted to a particular tissue. The surface of the targeted delivery system is modified in a variety of ways. In the case of a liposomal-targeted delivery system, lipid groups are incorporated into the lipid bilayer of the liposome in order to maintain the targeting ligand in stable association with the liposomal bilayer.

The administration of cells described herein is optionally tailored to an individual, by: (1) increasing or decreasing the amount cells injected; (2) varying the number of injections; or (3) varying the method of delivery of the cells.

Detection Methods

Methods for determining the expression or presence of biomarkers described supra are well known in the art, and can be measured, for example, by flow cytometry, immunohistochemistry, western blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

By "detecting expression" or detecting "expression levels" is intended for determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In some instances, the expression or presence of a biomarker described herein is determined at a nucleic acid level, using, for example, immunohistochemistry techniques or nucleic acid-based techniques such as in situ hybridization and RT-PCR. In some instances, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In some instances, the determining the expression or presence of a biomarker is carried out through gel electrophoresis. In some instances, the determination is carried out through transfer to a membrane and hybridization with a specific probe. In some instances, the determining the expression or presence of a biomarker is carried out by a diagnostic imaging technique. In some instances, the determining the expression or presence of a biomarker is carried out by a detectable solid substrate. In some instances, the detectable solid substrate is paramagnetic nanoparticles functionalized with antibodies.

In some instances, the expression or presence of a biomarker is at an RNA (e.g. mRNA) level. In some instances, techniques that detect RNA (e.g. mRNA) level include, but are not limited to, Southern or Northern analyses, polymerase chain reaction analyses and probe arrays.

One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker described herein. Hybridization of an mRNA with the probe indicates that the biomarker or other target protein of interest is being expressed.

In some instances, the mRNA is immobilized on a solid surface and contacted with a probe, for example by running the isolated mRNA on an agarose gel and transferring the mRNA from the gel to a membrane, such as nitrocellulose. In some instances, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR, ligase chain reaction, self-sustained sequence replication, transcriptional amplification system, Q-Beta Replicase, rolling circle replication or any other nucleic acid amplification method, followed by the detection of the amplified molecules using techniques well known to those of skill in the art. These detection schemes are especially useful for the detection of nucleic acid molecules if such molecules are present in very low numbers. In some instances, biomarker expression is assessed by quantitative fluorogenic RT-PCR (e.g., the TAQMAN® System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). The detection of expression also comprises using nucleic acid probes in solution.

In some instances, microarrays are used to determine expression or presence of one or more biomarkers. Nucleic acid microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. High-density oligonucleotide arrays are particularly useful for determining the gene expression profile for a large number of RNA's in a sample.

In some instances, an array is fabricated on a surface of virtually any shape or even a multiplicity of surfaces. In some instances, an array is a planar array surface. In some instances, arrays include peptides or nucleic acids on beads, gels, polymeric surfaces, fibers such as fiber optics, glass or any other appropriate substrate. In some instances, arrays are packaged in such a manner as to allow for diagnostics or other manipulation of an all-inclusive device.

In some instances, the expression or presence of a biomarker described herein is determined at a protein level, using, for example, antibodies that are directed against specific biomarker proteins. These antibodies are used in various methods such as western blot, ELISA, multiplexing technologies, immunoprecipitation, or immunohistochemistry techniques. In some instances, detection of biomarkers is accomplished by ELISA. In some instances, detection of biomarkers is accomplished by electrochemiluminescence (ECL).

Any means for specifically identifying and quantifying a biomarker in the biological sample is contemplated. Thus, in some instances, expression level of a biomarker protein of interest in a biological sample is detected by means of a binding protein capable of interacting specifically with that biomarker protein or a biologically active variant thereof. In some instances, labeled antibodies, binding portions thereof, or other binding partners are used. The word "label" when used herein refers to a detectable compound or composition that is conjugated directly or indirectly to the antibody so as to generate a "labeled" antibody. In some instances, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art.

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (e.g., ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In some instances, expression or presence of one or more biomarkers or other proteins of interest within a biological sample is determined by radioimmunoassays or enzyme-linked immunoassays (ELISAs), competitive binding enzyme-linked immunoassays, dot blot, Western blot, chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

Methods of Obtaining precursory regulatory Cytotrophoblasts

In some embodiments, a prCTB herein (e.g., a human prCTB) is derived in vitro from a pluripotent stem cell, e.g., a chorionic villi-derived progenitor cell. In some cases, a prCTB is differentiated from a pluripotent stem cell in a culture medium supplemented with one or more differentiation factors. In some cases, the stem cells are chorionic villi-derived progenitor cells. In some cases, a chorionic villi-derived progenitor cell comprises a mammalian trophoblast stem cell, e.g., a human trophoblast stem cell.

In some cases, disclosed herein is a method of obtaining precursory regulatory cytotrophoblasts (prCTBs), comprising: differentiating pluripotent stem cells in vitro by contacting the stem cells with a fibroblast growth factor in a culture medium. In some cases, the culture medium comprises nucleosides, L-glutamine, a dipeptide comprising L-glutamine, platelet lysate, or a combination thereof. In some cases, the culture medium comprises nucleosides, the dipeptide, and platelet lysate. In some cases, the culture medium comprises from about 2 mM to about 200 mM of L-glutamine.

In some cases, a pluripotent stem cell, e.g., a human trophoblast stem cells is contacted with a fibroblast growth factor for about 24 hours to 48 hours, thereby generating a prCTB. In some cases, the contacting is at least about 18 hours, 20 hours, 22 hours, 24 hours, 26 hours, 28 hours, 30 hours, 32 hours, 34 hours, 36 hours, 40 hours, or 44 hours. In some cases, the contacting is at most about 20 hours, 22 hours, 24 hours, 26 hours, 28 hours, 30 hours, 32 hours, 34 hours, 36 hours, 40 hours, 44 hours, or 48 hours.

In some cases, a pluripotent stem cell, e.g., a human trophoblast stem cells is contacted with a fibroblast growth factor when the stem cell is at passage 5 to 10. In some cases, pluripotent stem cell is contacted with a fibroblast growth factor when the stem cell is at passage 2, 3, 4, 5, 6, 7, 8, 9, 10, 11, 12, 13, 14, or 15.

In some instances, the method comprises culturing the stem cells with the culture medium before contacting them with the fibroblast growth factor to differentiate into the prCTBs.

In some cases, the culture medium for obtaining and/or maintaining prCTBs is free from an antibiotic, for instance, penicillin, streptomycin, or any combination thereof. In some cases, the culture medium for obtaining and/or maintaining prCTBs is free from retinoic acid. In some cases, the culture medium for obtaining and/or maintaining prCTBs is free from mercaptoethanol, nicotinamide, or a combination thereof. In some cases, the culture medium for obtaining and/or maintaining prCTB is free from dexamethasone, recombinant human oncostatin M, BMP4, HGF, or any combination thereof. In some cases, the culture medium for obtaining and/or maintaining prCTB is xeno-free, e.g., free from an animal component. In some cases, the culture medium for obtaining and/or maintaining prCTB is free from a human-derived component and an animal-derived component, e.g., being a chemically defined medium. In some cases, the culture medium for obtaining and/or maintaining prCTB is free from a serum. In some cases, the culture medium for obtaining and/or maintaining prCTB is free from fetal bovine serum.

In some cases, the fibroblast growth factor is basic fibroblast growth factor (bFGF). In some cases, the stem cell is contacted with about 1 ng/ml to about 100 ng/ml bFGF. In some cases, the stem cell is contacted with about 2 ng/ml to about 50 ng/ml, about 4 ng/ml to about 30 ng/ml, about 6 ng/ml to about 15 ng/ml, or about 8 ng/ml to about 12 ng/ml bFGF. In some cases, the stem cell is contacted with about 6 ng/ml, 7 ng/ml, 8 ng/ml, 9 ng/ml, 10 ng/ml, 11 ng/ml, 12 ng/ml, 13 ng/ml, 14 ng/ml, or 15 ng/ml bFGF. In some cases, the stem cell is contacted with about 10 ng/ml bFGF.

Methods of Obtaining Mammalian Trophoblast Stem Cells

In some embodiments, a mammalian trophoblast stem cell herein (e.g., a human trophoblast stem hTS cell) can be isolated from umbilical cord, amniotic fluid, amniotic membrane, the Wharton's jelly, the chorionic villi, placenta, or ectopic pregnancy, in a manner that is not disturbing nor destructive to an embryo.

In some cases, a mammalian trophoblast stem cell described herein is cultured in a culture medium free from an antibiotic, for instance, penicillin, streptomycin, or any combination thereof. In some cases, the culture medium for obtaining the mammalian trophoblast stem cell is free from retinoic acid. In some cases, the culture medium obtaining and/or passaging the mammalian trophoblast stem cell is free from mercaptoethanol, nicotinamide, or a combination thereof. In some cases, the culture medium obtaining and/or passaging the mammalian trophoblast stem cell is free from dexamethasone, recombinant human oncostatin M, BMP4, HGF, or any combination thereof. In some cases, the culture medium obtaining and/or passaging the mammalian trophoblast stem cell is xeno-free, e.g., free from an animal component. In some cases, the culture medium for obtaining and/or passaging the mammalian trophoblast stem cell is free from a human-derived component and an animal-derived component, e.g., being a chemically defined medium. In some cases, the culture medium obtaining and/or passaging the mammalian trophoblast stem cell is free from a serum. In some cases, the culture medium obtaining and/or passaging the mammalian trophoblast stem cell is free from fetal bovine serum.

In one instance, a mammalian trophoblast stem cell herein (e.g., an hTS cell) can be isolated from amniocentesis biopsies or from amniotic fluid. In one instance, amniocentesis can be a procedure used to obtain a small sample of the amniotic fluid that surrounds the fetus during pregnancy. In one instance, an amniocentesis can be offered to women between the 15th and 20th weeks of pregnancy who are at increased risk for chromosome abnormalities, e.g., women who are over 35 years of age at delivery, or those who have had an abnormal maternal serum (blood) screening test indicating an increased risk for a chromosomal abnormality or neural tube defect. In one instance, a needle, e.g., a long, thin, hollow needle, can be used with ultrasound guide through your abdomen, into the uterus and the amniotic sac. A predetermined amount of amniotic fluid, e.g. one ounce, can be drawn into a syringe.

In another instance, a mammalian trophoblast stem cell herein (e.g., an hTS cell) can be obtained from blastomere biopsy during preimplantation genetic diagnosis (PGD), e.g., in conjunction with reproductive therapies such as in vitro fertilization (IVF). In one instance, the cells herein can be produced by methods for biopsy of a blastocyst, wherein the remainder of the blastocyst is implanted and results in a pregnancy and later in a live birth, e.g., the zona pellucida is removed from the blastocyst and then the blastocyst is biopsied.

In another instance, a mammalian trophoblast stem cell herein (e.g., an hTS cell) can be obtained from prenatal chorionic villus sampling (CVS). In one instance, CVS can be a prenatal test that involves taking a sample of tissue from the placenta to test for chromosomal abnormalities and certain other genetic problems. In one instance, CVS can be performed between the 10th and 12th weeks of pregnancy. In one instance, the CVS procedure is transcervical, e.g., a catheter is inserted through the cervix into the placenta to obtain the tissue sample. In one instance, the CVS procedure is transabdominal, e.g., a needle is inserted through the abdomen and uterus into the placenta to obtain the tissue sample.

In one instance, a mammalian trophoblast stem cell herein (e.g., an hTS cell) can be obtained from placental biopsies after full-term pregnancies. In one instance, a mammalian trophoblast stem cell herein (e.g., an hTS cell) herein can be isolated from a placenta after a vaginal delivery or a cesarean section delivery.

In some embodiments, a mammalian trophoblast stem cell herein (e.g., an hTS cell) can be isolated from first trimester chorionic villous sampling (e.g., $8^{+3}$ to $12^{+0}$ weeks gestational age) or term placenta from caesarean section deliveries. The chorionic tissue can be separated from the amnion, minced, and/or enzymatically digested (e.g., with 0.05% trypsin EDTA, e.g., for 20 min). Cells are subsequently centrifuged (e.g., at 1500 rpm, e.g., for 5 min), counted, and/or replated (e.g., 104 cells per $cm^2$) in a medium (e.g., Dulbecco's modified Eagle's medium+10% fetal bovine serum). In one instance, isolated cells can be plastic adherent. In one instance, the cells can be used at passage 4-8.

In one instance, a mammalian trophoblast stem cell herein (e.g., an hTS cell) can be isolated from term (e.g., 38-40 weeks' gestation) placentas according to the following procedure. Umbilical cord blood is allowed to drain from the placentas, which are then dissected carefully. The harvested pieces of tissue are washed several times (e.g., in phosphate-buffered saline) and then minced (e.g., mechanically) and enzymatically digested (e.g., with 0.25% trypsin-EDTA). The homogenate is subsequently pelleted by centrifugation and suspended in complete medium (e.g., Dulbecco's modified Eagle's medium supplemented by 10% fetal bovine serum, 100 U/ml penicillin, and/or 100 g/ml streptomycin). Cell cultures are maintained at a suitable condition, e.g., 37° C. with a water-saturated atmosphere and 5% $CO_2$. Medium is replaced periodically, e.g., one to two times every week. When cells are reach a desired level of confluence, e.g., more than 80% confluence, they are recovered, e.g., with 0.25% trypsin/EDTA, and replated at a dilution, e.g., of 1:3.

In another instance, a mammalian trophoblast stem cell herein (e.g., an hTS cell) can be isolated from human placentas following delivery according to a procedure as follows. The chorion is separated from the amnion by peeling them apart. The decidual tissue are scrapped (e.g., mechanically) and washed (e.g., in Dulbecco's phosphate-buffered saline) before being cut into small pieces (e.g., –2×2 cm). The chorion are chopped into small pieces and subjected in to an enzyme (e.g., 0.5% trypsin-EDTA, e.g., for 5 min), followed by digestion with collagenase I (e.g., at 0.3% in 37° C. incubator for 20 to 30 min). The mobilized cells are then collected and passed through a cell strainer (e.g., 100 µm). The filtered cells are collected by centrifugation (e.g., at 2,500 rpm, e.g., for 5 min). The cells are resuspended in a medium (e.g., α-modified minimum essential medium supplemented with 10% fetal bovine serum and/or 1% penicillin-streptomycin), and cultured in a container, e.g., T25 flasks, at a suitable condition (e.g., at 37° C. and/or 5% $CO_2$). The media is changed periodically, e.g., every 3 days, until the chorionic MSCs reached a desired level of confluency, e.g., 70% confluency.

In another instance, chorionic villi can be obtained from the fallopian tubes of un-ruptured pre-implantation embryos in women with ectopic pregnancy (e.g., gestational age: 5-7 weeks). Tiny villous tissues can be well-minced in a suitable medium (e.g., serum-free α-MEM) and identified under microscopy followed by trypsinization (e.g., with 0.025% trypsin/EDTA) for a period of time (e.g., 15 min) and by adding a medium (e.g., α-MEM containing 10% FBS) to halt the reaction. Adherent cells can be obtained and cultured in a suitable condition (e.g., in conditioned α-MEM, 10% FBS, and 1% penicillin-streptomycin at 37° C. in 5% $CO_2$). After two passages, the level of hCG can become undetectable measured by a commercial kit (e.g., Dako, Carpinteria, Calif.).

Kits/Articles of Manufacture

Disclosed herein are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some instances, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of use.

For example, the container(s) include hTS cells, optionally in a composition as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some instances, a label is on or associated with the container. In some instances, a label is on a container when letters, numbers or other characters forming the label are attached, molded or etched into the container itself; a label is associated with a container when it is present within a receptacle or carrier that also holds the container, e.g., as a package insert. In some instances, a label is used to indicate that the contents are to be used for a specific therapeutic application. The label also indicates directions for use of the contents, such as in the methods described herein.

EXAMPLES

The Examples below are non-limiting and merely representative of various aspects and features of the present inventions.

Example 1

Transforming Character of human Trophoblast Stem (hTS) Cells upon Stress.

Figure 1B:
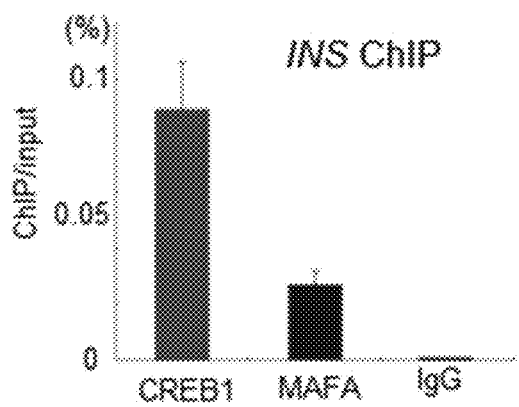
Figure 1C:
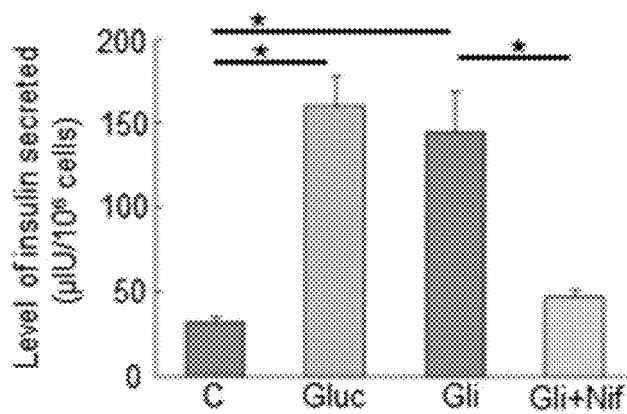
Figure 2A:
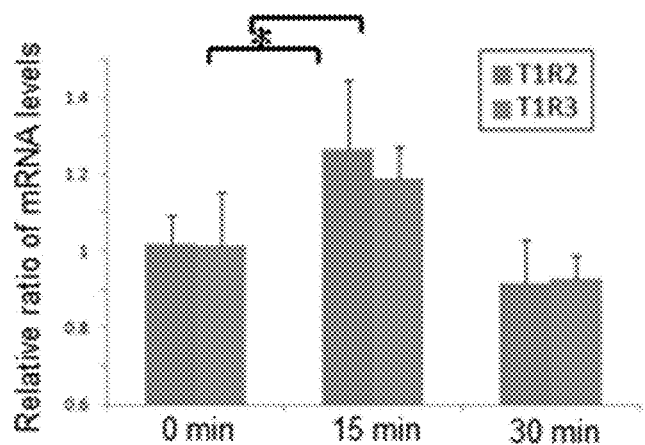
Figure 2B:
Figure 2C:
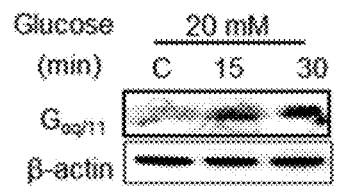
Figure 2D:
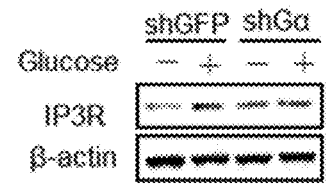
Figure 2E:
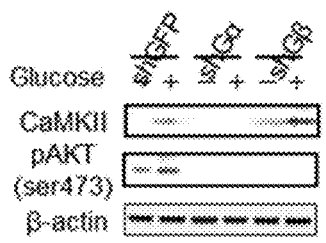
Figure 2F:
Figure 2G:
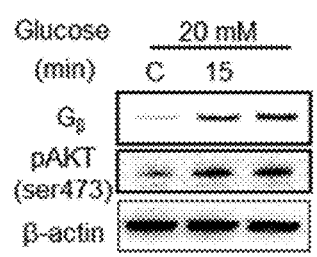

To examine how blastocystic trophoblasts challenge the maternal hyperglycemic threat during the embryonic transportation in the fallopian tube, the effect of high glucose (20 mM) was tested on the hTS cells. It was found that glucose rapidly induced transiently activation of sweet taste receptors T1R2/T1R3 at the cell membrane to subsequently activate G-protein signalings in cell, giving rise to the Gαq/11/CaMKII/CREB1 and the Gβ/GSK3β/MAFA signaling pathways (FIG. 1A). The regulatory molecular mechanisms were depicted in Supplementary Information (FIGS. 2A to 2J). In the nucleus, two G-protein pathways coordinately targeted at the promoters of insulin gene for transcription to produce insulin (FIG. 1A). Knockdown of transcription factors CREB1 and MAFA by specific shRNAs reduced insulin expression by ChIP-qPCR analysis (FIG. 1B). Meanwhile, the activated T1R2/T1R3 signaling induced the glucose sensor and transporter GLUT2 to promote glucose entrance into the cells. Glucose augmented ATP production to open the L-type voltage-gated Ca2+ channels (VGCC), resulting in the entrance of extracellular calcium into the cells that promotes insulin secretion into the culture medium detected by radioimmunoassay (RIA). This action was confirmed by that sulfonylurea promoted insulin secretion, while a VGCC inhibitor nifedipine blocked insulin secretion measured by RIA (FIG. 1C). These results suggested that glucose enables control of insulin synthesis and secretion in hTS cells. This insulin expression can be attributed to CREB1 signal but not conventional pancreatic and duodenal homeobox 1 (PDX1) measured by qPCR analysis (FIG. 2K).

Figure 1D:
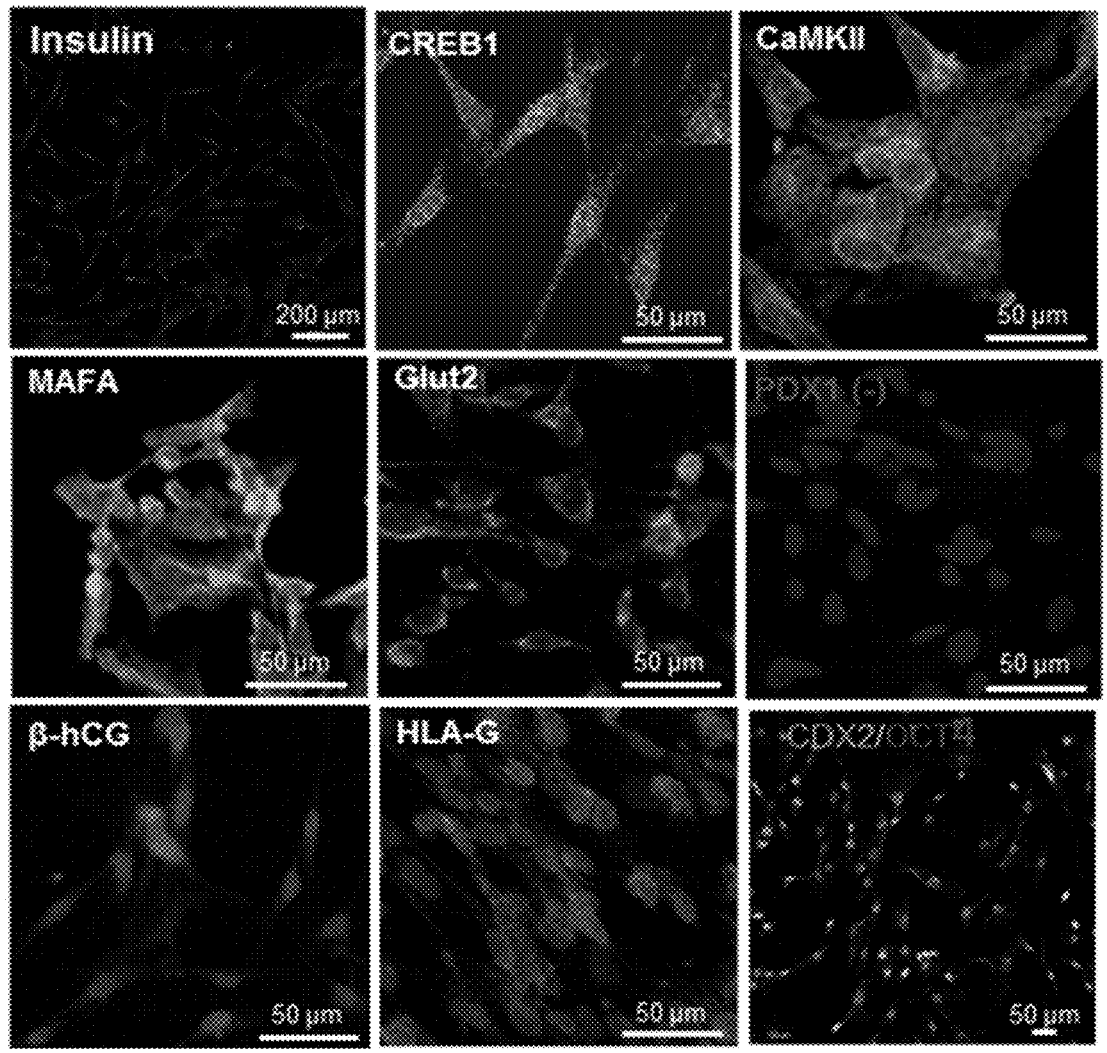

Furthermore, immunofluorescence imaging study revealed the not only insulin, CREB1, CaMKII, GLUT2, and MAFA, but also β-hCG, histocompatibility antigen HLA-G, and pluripotency transcription factor CDX2 but not OCT4 (octamer-binding transcription factor 4) were expressed in hTS cells (FIG. 1D). Stress protein heat shock protein HSP90 was also expressed. But hTSCs also did not express proliferation marker Ki-67, protein folding activator HSP70, tumor suppressor p53, autoantigen GAD65, and cell-cell fusion protein Syncytin (FIG. 2M), supporting the concept that hTSCs stand at the first position of TE-differentiated trophoblasts.

The stress effect of glucose on hTS cells morphologically was further examined, showing that high glucose rapidly induced cellular changes from adhered fibroblastic feature to a 3D aggregated cell cluster with positive staining of zinc-chelating agent dithizone (DTZ), a specific staining for β-cells in vitro culture. Withdrawal of high glucose led to a swift release of cells from the cluster to re-adhere on dish again, reverting to the original fibroblastic features. The cellular processes were recorded by a computer microscopy video system (Olympus, IX-81, DP30, MIU-IBC-IF-2) shown in the Supplementary Online Video (Video S1). Moreover, ultrastructural study of the cell cluster revealed a large cytoplasm to nuclear ratio with desmosomes junction between two cells. Various empty vesicles, abundant mitochondria, and immature granules in vesicles were observed in the cytoplasmic compartment similar to that in pancreatic β-cell. To this end, it was demonstrated that hTS cells can have the ability to express insulin and stress protein HSP90 to cope with the external threats, wherein hTS cells can be highly susceptible to glucose stimulation, which can cause reversible cellular transformation of the hTS cells.

Example 2

In Vitro Induction of Precursory Regulatory Cytotrophoblasts (prCTBs).

The impact of bFGF on the trophectoderm-derived hTS cells was examined in this example. In one experiment, prCTBs were induced in vitro from hTS cells.

bFGF Induces Epithelial-Mesenchymal Transition (EMT) via TGF-β1.

Figure 4A:
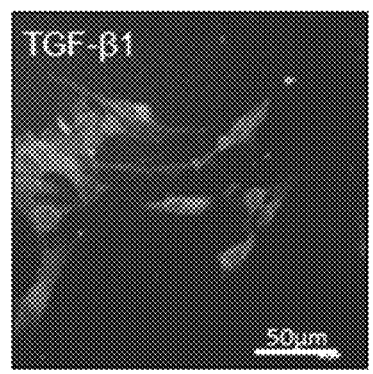
FIGS. 4A to 4F are described herein.
Figure 4B:
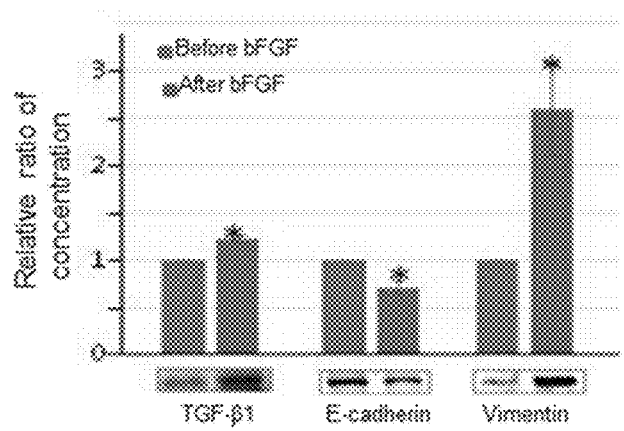
Figure 4C:
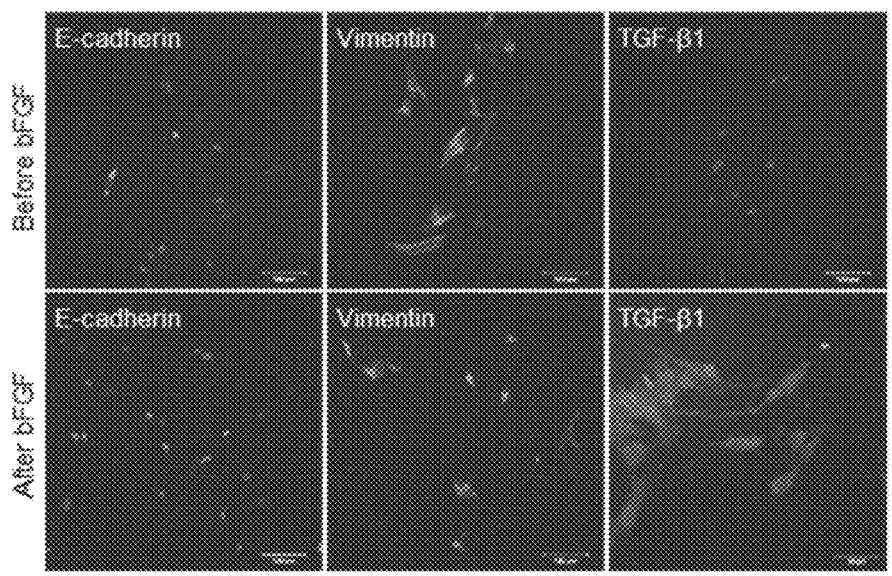
Figure 4D:
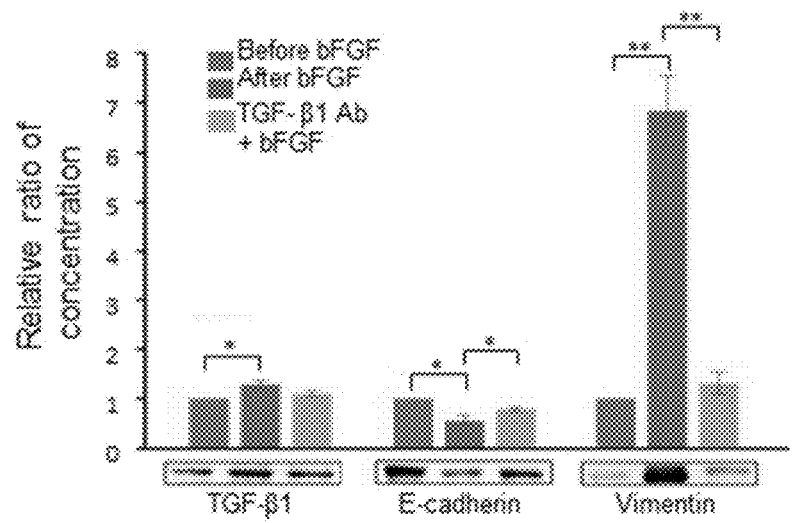
Figure 4E:
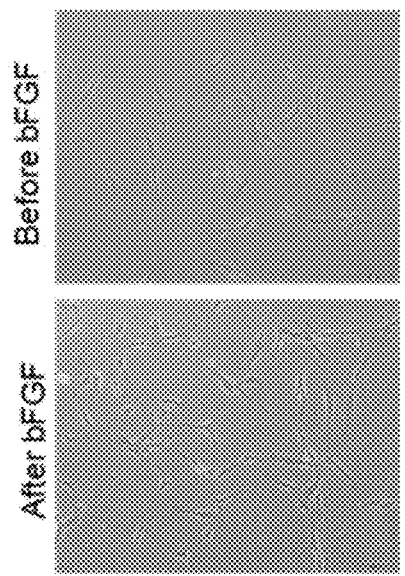

It was uncovered that bFGF induced TGF-β1 expression in hTSCs (FIG. 4A) and upregulated mesenchymal cell marker vimentin, but downregulated cell-cell adhesion protein E-cadherin by Western blot assay (FIG. 4B) and by immunocytochemistry (FIG. 4C). These actions were neutralized by pre-treatment with TGF-β1 antibody (FIG. 4D). Light microscopy revealed a cellular shape switching from elongated spindles towards fat and shortened features with a more rounded nucleus (FIG. 4E). These phenomena suggested that bFGF induces EMT to gain the capacity in migration and invasion.

bFGF Promotes Signatures of Definitive Endoderm (DE) via mRNA-124a.

It was found that bFGF targeted receptor FGFR1 at the cell membrane to induce activation of PI3K/AKT/CREB1 signaling pathway. By computational survey of DIANA-mirGen 2.0, it was verified that the bFGF-induced CREB1 targeted the consensus CREB binding sequence (TGACGTCA) at the promoter of microRNA-124a (miR-124a) by qPCR analysis, while knockdown of CREB1 reduced miR-124a expression. A positive correlation of CREB1 and miR-124a was observed.

Figure 4F:
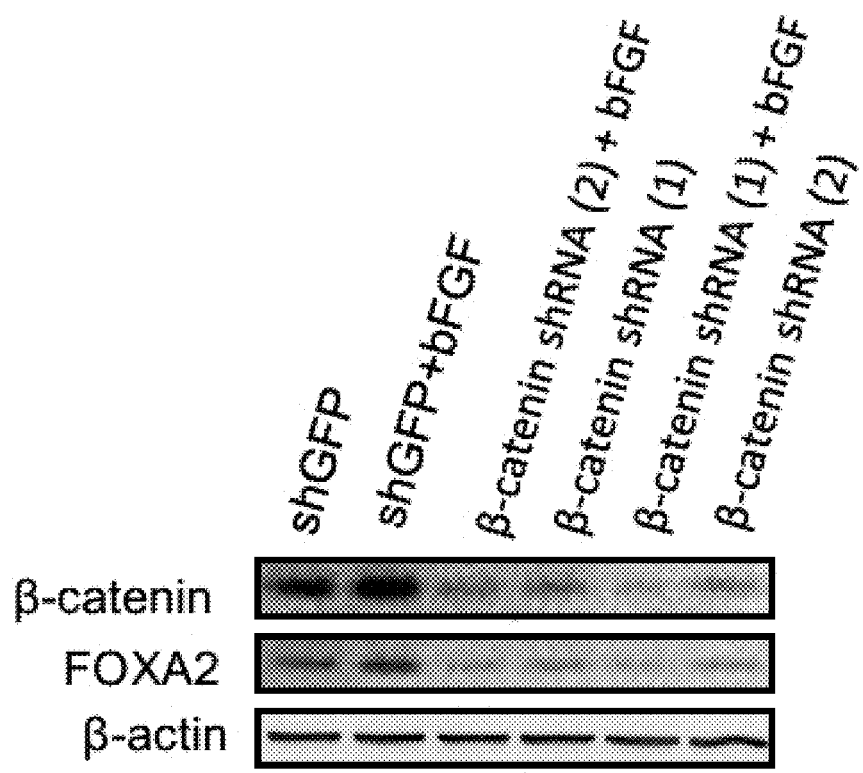

To gain insights into the downstream effectors of miR-124a, plasmids of SMAD4, GSK3β, and CDX2 using pGL4.51 vector (Promega, Madison, Wis.) were constructed for luciferase reporter gene assay. First, miR-124a was shown to target the SMAD4 gene, producing the inhibitory SMAD4. Since SMAD4 can interact with SMAD2/3 to bind to the sequences in the proximal promoters of MIXL1 gene for transcription, an inhibitory SMAD4 caused an inhibitory homeodomain protein MIXL1. This was verified by using SMAD4 shRNAs and supported imaging study (revealing that bFGF (10 ng/ml) induced apparent expression of MIXL1 at 15 min compared to control. MIXL1 expression decreased in intensity at 4 hr induction, indicating a transient expression). Second, miR-124a was shown to suppress glycogen synthase kinase 3β (GSK3β), verified by the pretreatments of miR-124a and anti-miR-124a antibody. As a result, an inhibitory GSK3β caused accumulation of downstream β-catenin, leading to the nuclear translocation to target at FOXA2 gene for transcription, evidenced by using shRNAs against β-catenin assay (FIG. 4F). In turn, forkhead box protein A2 (FOXA2) controlled PDX1 expression, contributing to the pro-endocrine transcription factor neurogenin 3 (NGN3) to involve in the specification of endocrine cell differentiation. Third, miR-124a targeted at CDX2 gene to inhibit CDX2 synthesis, verified by the pretreatments of miR-124a and anti-miR-124a antibody. Downregulated CDX2 resulted in upregulation of OCT4. In turn, OCT4 targeted at SOX17 gene for transcription to produce SOX17 (SRY-Box protein 17), supported by the imaging study. Together, it was demonstrated that bFGF can promote miR-124a to consequently get signatures of definitive endoderm (DE) by upregulation of SOX17, FOXA2, and OCT4 as well as downregulation of MIXL1 in 8 hr induction, which can contribute to further insulin expression.

bFGF Induces Generation of prCTBs from hTS Cells.

Figure 3:
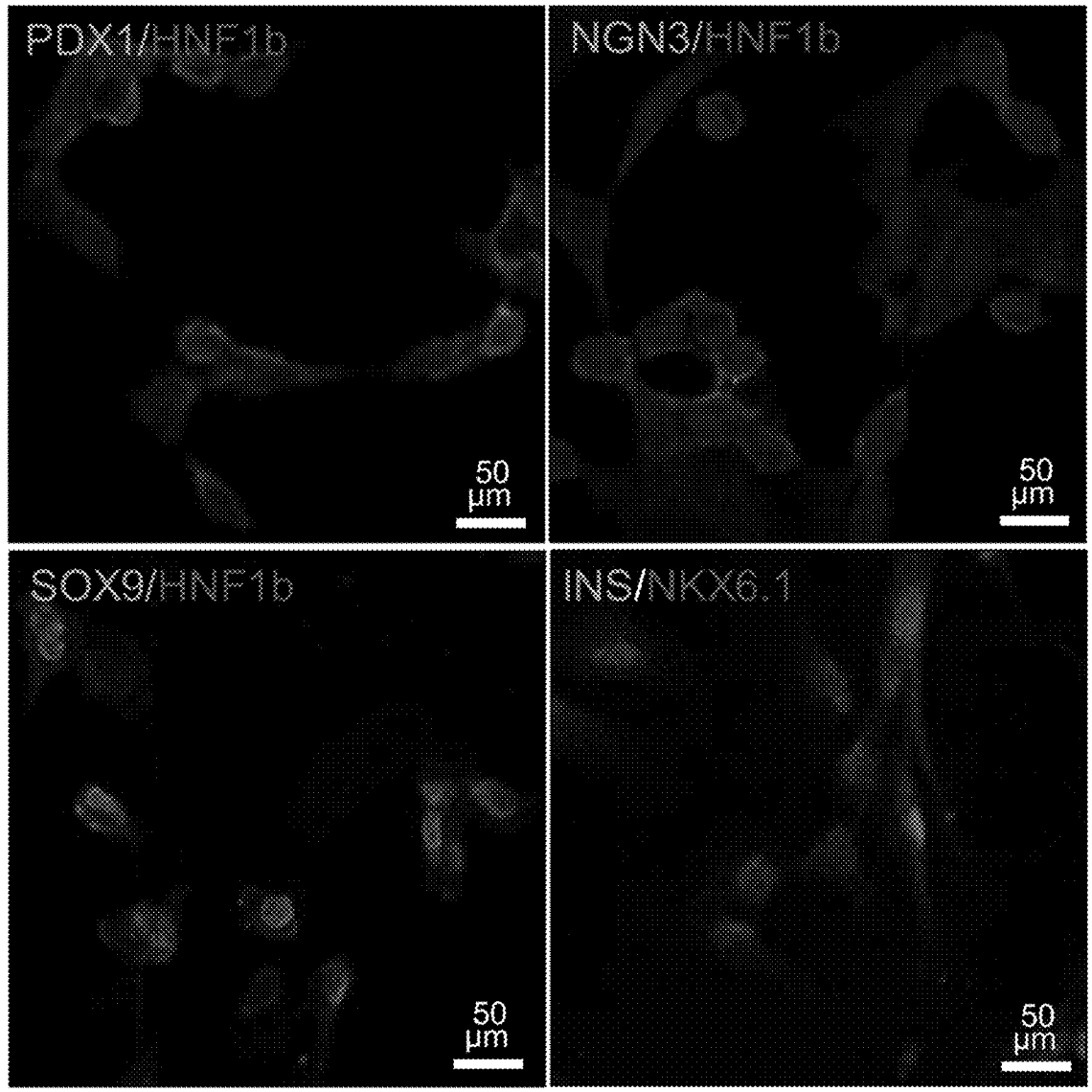
FIG. 3 shows representative images of insulin-related immunoreactive molecules, including PDX1, HNF-1β, NGN3, SOX9, NKX6.1, and insulin in prCTBs. Bar Scale bar: 50 μm.

The significant upregulation of pancreatic progenitor biomarkers, including PDX1, pancreas transcription factor 1 protein (PTF1a), SOX9, and homeobox 1 protein NKX (NKX6.1) were noted at 8 hr of bFGF induction. The appearance of these molecular signals initiated the expressions of NGN3, pro-insulin C-peptide, and insulin at 20 hr of induction. Besides insulin, immunofluorescence imaging confirmed the presence of a variety of pancreatic progenitor- and endocrine cell-markers, including PDX1, hepatocyte nuclear factor-1-beta (HNF1B), NGN3, SOX9, NKX6.1, and insulin as well as NANOG, SOX2, glucagon, somatostatin, GLUT2, and polypeptide (PP) in the bFGF-treated hTS cells (FIG. 3).

Figure 5A:
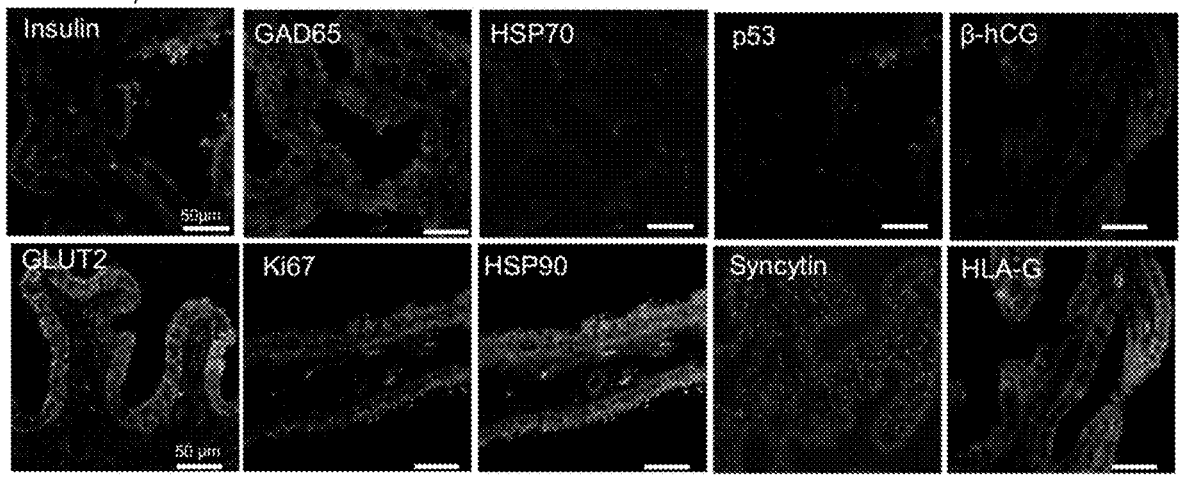
FIGS. 5A-5C illustrate biological characteristics of precursory regulatory cytotrophoblasts (prCTBs).
Figure 5B:
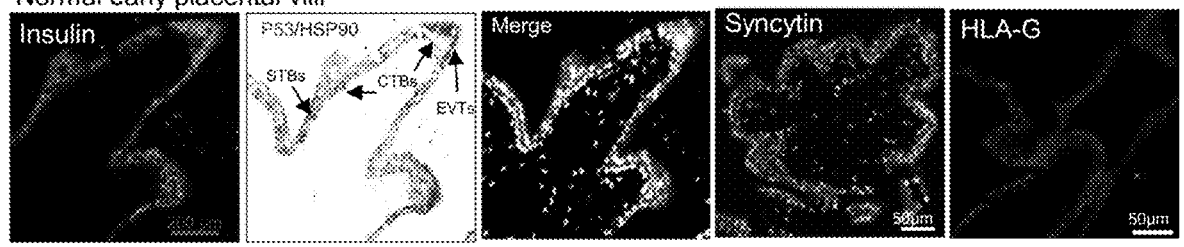
Figure 5C:
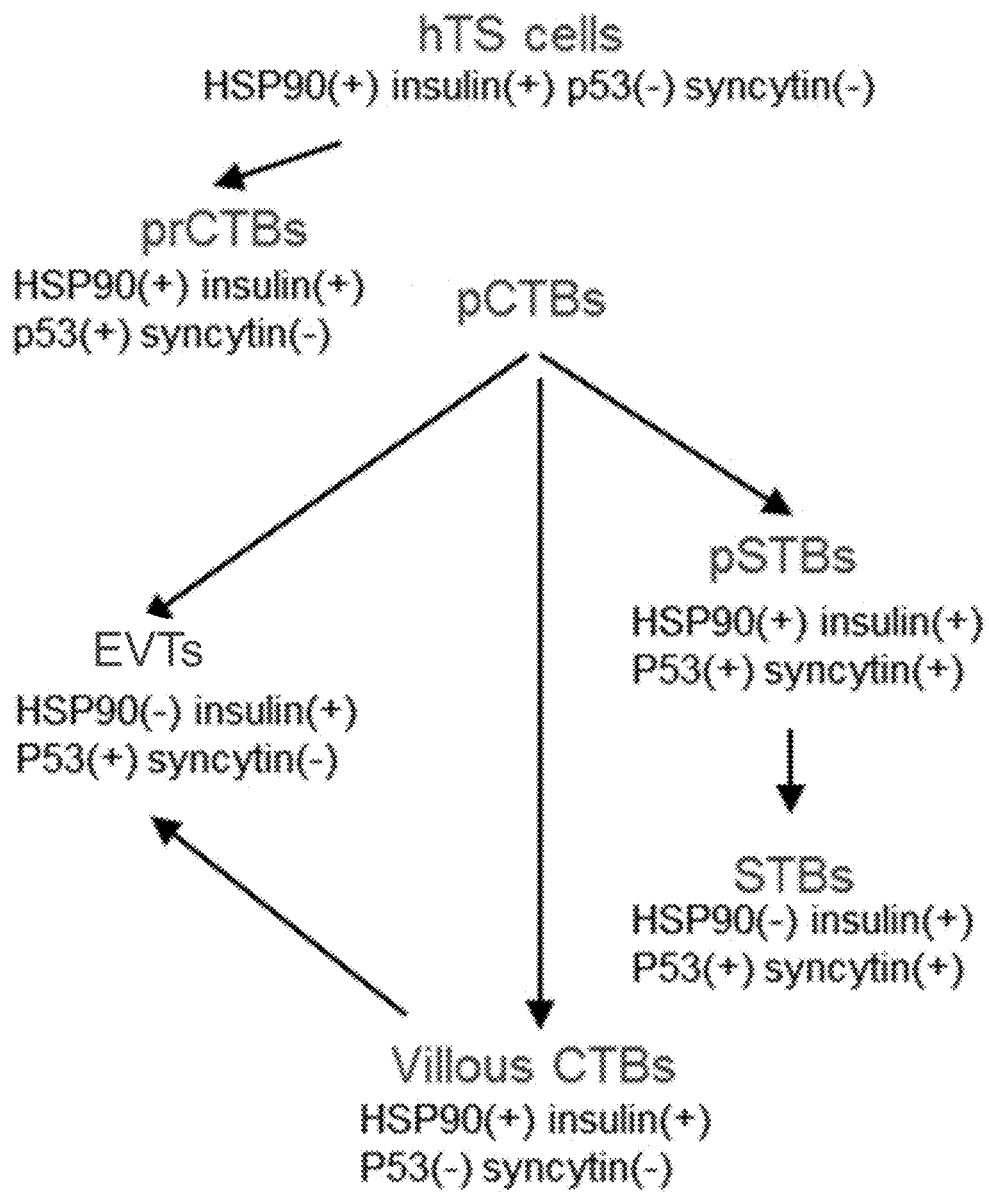
Figure 6A:
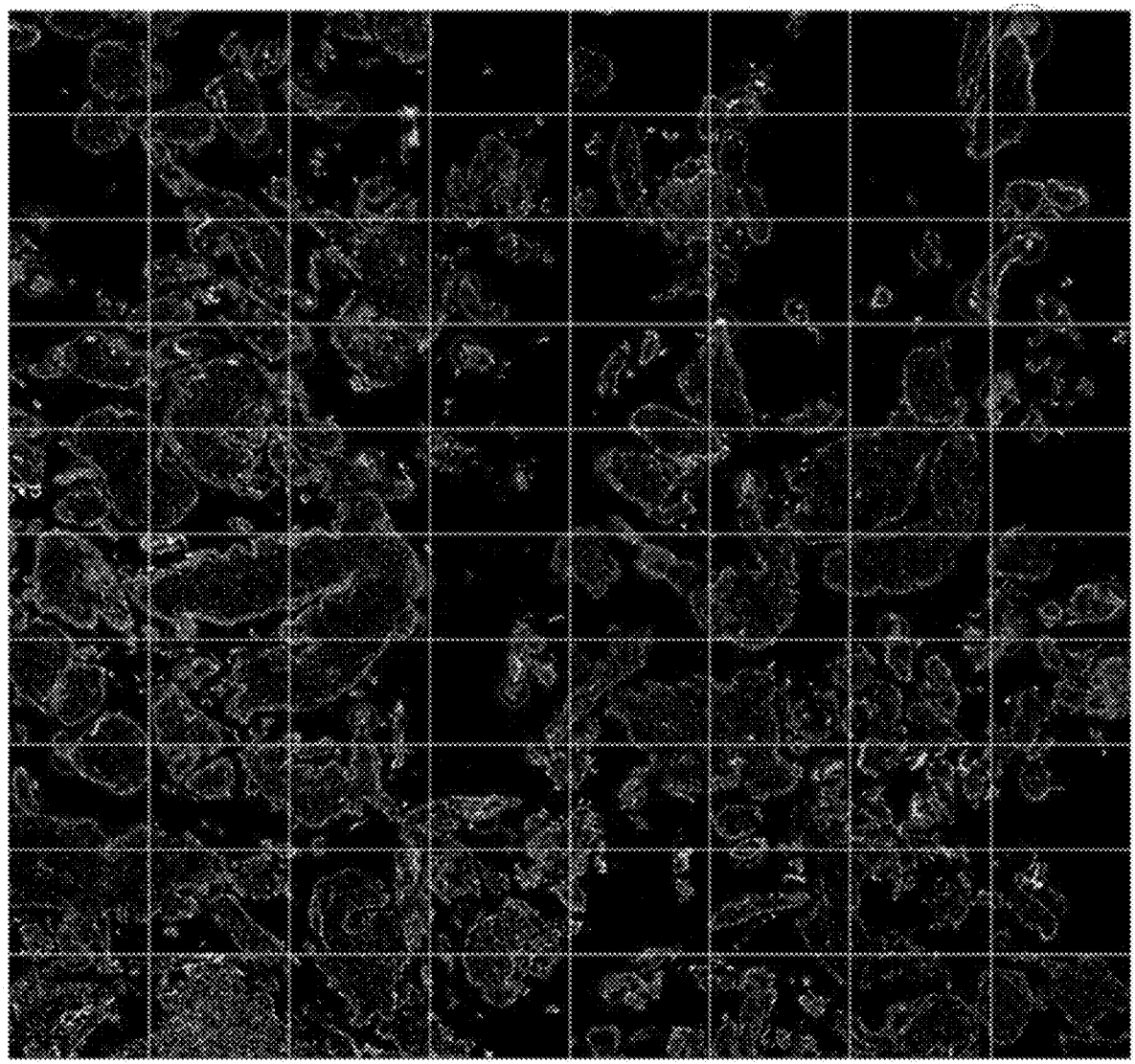
FIGS. 6A and 6B show comparison of stress protein p53- and insulin-expressing syncytial knots in chorionic villi between normal pregnancy and blighted ovum. The stressed syncytial knots are defined by expressing insulin and p53 at an area containing over 15 positive cells counted in a single chorionic villi at 8 weeks of normal gestation (FIG. 6A); while chorionic villi of patient with blighted ovum at 7-8 weeks of gestation (FIG. 6B), showing that the frequency of stress syncytial knot occurs in (FIG. 6B) is 1.96-fold higher than that in (FIG. 6A). The number of syncytial knot has been counted independently by two assistants in 80 fields (FIG. 6A) and in 50 fields (FIG. 6B). Whereas another 25 fields are not shown.
Figure 6B:
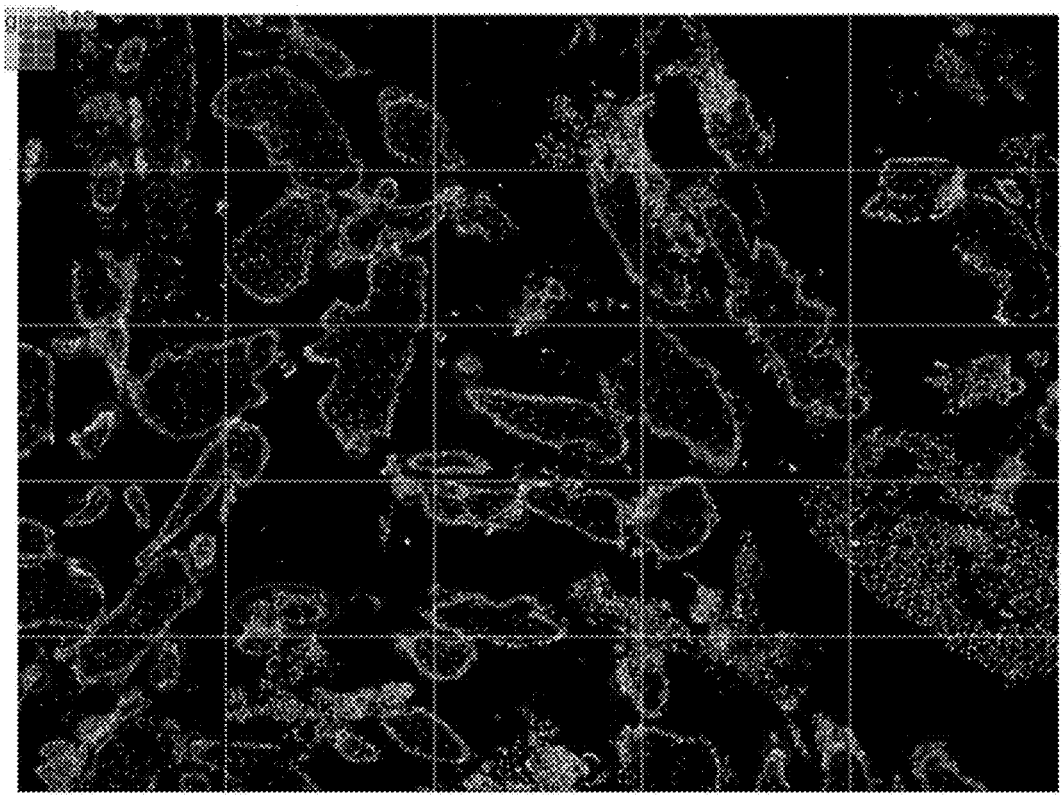
Figure 6C:
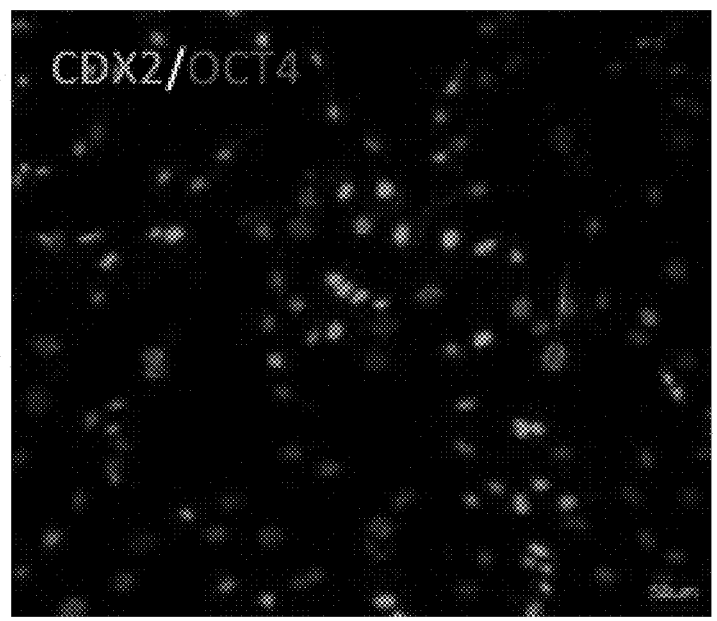
FIG. 6C shows change in expression of pluripotent transcription factors during cell transformation immunoreactive OCT4 but not CDX2 imaging at DE stage by 4 hr induction.

Next, it was discovered that initially, the bFGF-induced hTS cells expressed CDX2 but not OCT4 (FIG. 5C). As differentiation proceeded, OCT4 upregulated while CDX2 downregulated, regulating the pluripotency of DE stage at 8 hr induction. When OCT4 gradually downregulated and NANOG upregulated to peak at 12 hr induction similar to the stage of mesendoderm. Wherein, HSP90 maintained the levels of OCT4 and NANOG in the differentiating trophoblasts. As differentiation entered the stage of progenitors, NANOG was downregulated but SOX2 sustained upregulation after 12 hr induction toward the end of day, where insulin-expressing prCTBs were formed. Notably, these molecular processes are similar to the development of β-cells in pancreas but distinguish from the glucose-induced insulin expression in hTS cells as described previously. The spatiotemporal swift in pluripotency transcription factors is mainly attributed from reciprocal negative autoregulatory mechanisms, whereas SOX2 plays a main role in the maintenance of stemness of prCTBs. To this end, it was demonstrated in our experiments that bFGF efficiently can induce differentiation of isolated hTS cells toward a novel extrapancreatic tissue-specific phenotype that expresses insulin, which is termed precursory regulatory cytotrophoblasts (prCTBs) herein. As demonstrated here, prCTBs can be maintained mainly by SOX2 during trophoblast differentiation in vitro.

Example 3

Differences of prCTBs from hTS cells and Primitive Cytotrophoblasts

Figure 2M:
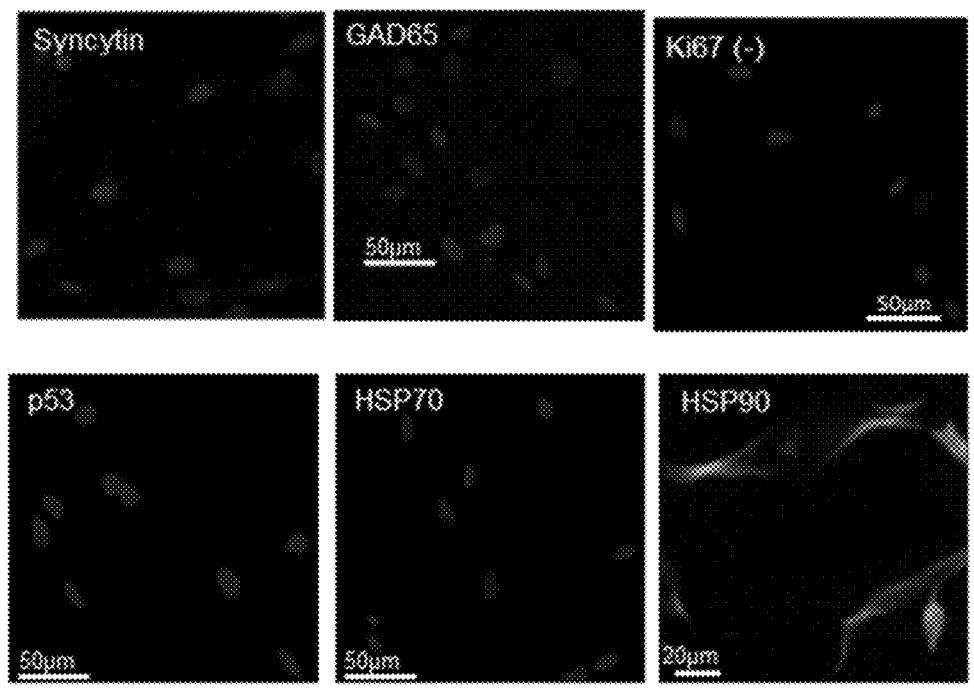

Immunohistochemistry revealed that most of prCTB cells were stained by insulin, GLUT2, CaMKII, Ki67 (a proliferation factor), β-hCG, and HLA-G, suggesting prCTBs have proliferating character (FIG. 5A). The stress proteins including GAD65, HSP70, HSP90, and p53 excluding syncytin were also expressed in the prCTBs, but distinguish from the findings in the hTS cells (FIG. 2M). These results implied that the effects of extracellular stressors can drive the transformation of hTS cells towards prCTBs in vitro.

In normal uterine pregnancy, primitive cytotrophoblasts (pCTBs) can give rise to: 1) villous cytotrophoblasts; 2) primitive syncytiotrophoblasts (pSTBs) and later syncytiotrophoblasts (STBs); and 3) extravillous cytotrophoblasts (EVTs). It was uncovered that villous cytotrophoblasts expressed HSP90 and insulin, but no p53 and syncytin (FIG. 5B). STBs expressed insulin, p53, and syncytin, but no HSP90. EVTs expressed apparent insulin and p53 but no HSP90 and syncytin, suggesting an invasive but no proliferative character. FIG. 5C depicts such developmental process.

Example 4

Secretomes or Exosomes from hTS Cells and prCTBs.

The levels of chemokines, cytokine, and growth factors were measured in the culture media of both hTS cells and prCTBs by MILLIPLEX® assay based on LUMINEX® technology. The results revealed that both hTS cells and prCTBs are able to release apparent amount of a variety of secretomes or exosomes (FIG. 7A, upper panel), including:

1) Chemokines

This group included RANTES (also as CCL5), MCP-1 (also CCL2, monocyte chemoattractant protein-1), GROα (also CXCL1, CXCL2, macrophage inflammatory protein 2-α or MIP2-α), MCP-3 (also CCL7), IL-8, Eotaxin (also CCL11, CCL24, and CCL26), MDC (also CCL22), IP-10 (also IFN γ-induced CXCL10), Fractalkine (also CX3CL1), MIP-1β (also CCL4), and soluble CD40-ligand (also sCD40L, CD154).

2) Cytokines and Growth Factors

This group included IL-6, IL-10, IL-4, IL-7, IL-15, IL-13, IL-1α, IL-1β, IL-12p40, IL-3, and IL-2. IFN-γ and IFN-α were also secreted. While growth factors included: PDGF-AA and PDGF-AB/BB (platelet-derived growth factor family), VEGF, EGF (epidermal growth factor), bFGF, GM-CSF (granulocyte-macrophage colony-stimulating factor), Flt3L (FMS-like tyrosine kinase 3 ligand), and IL-1β.

3) Other Proteins

Figure 7A:
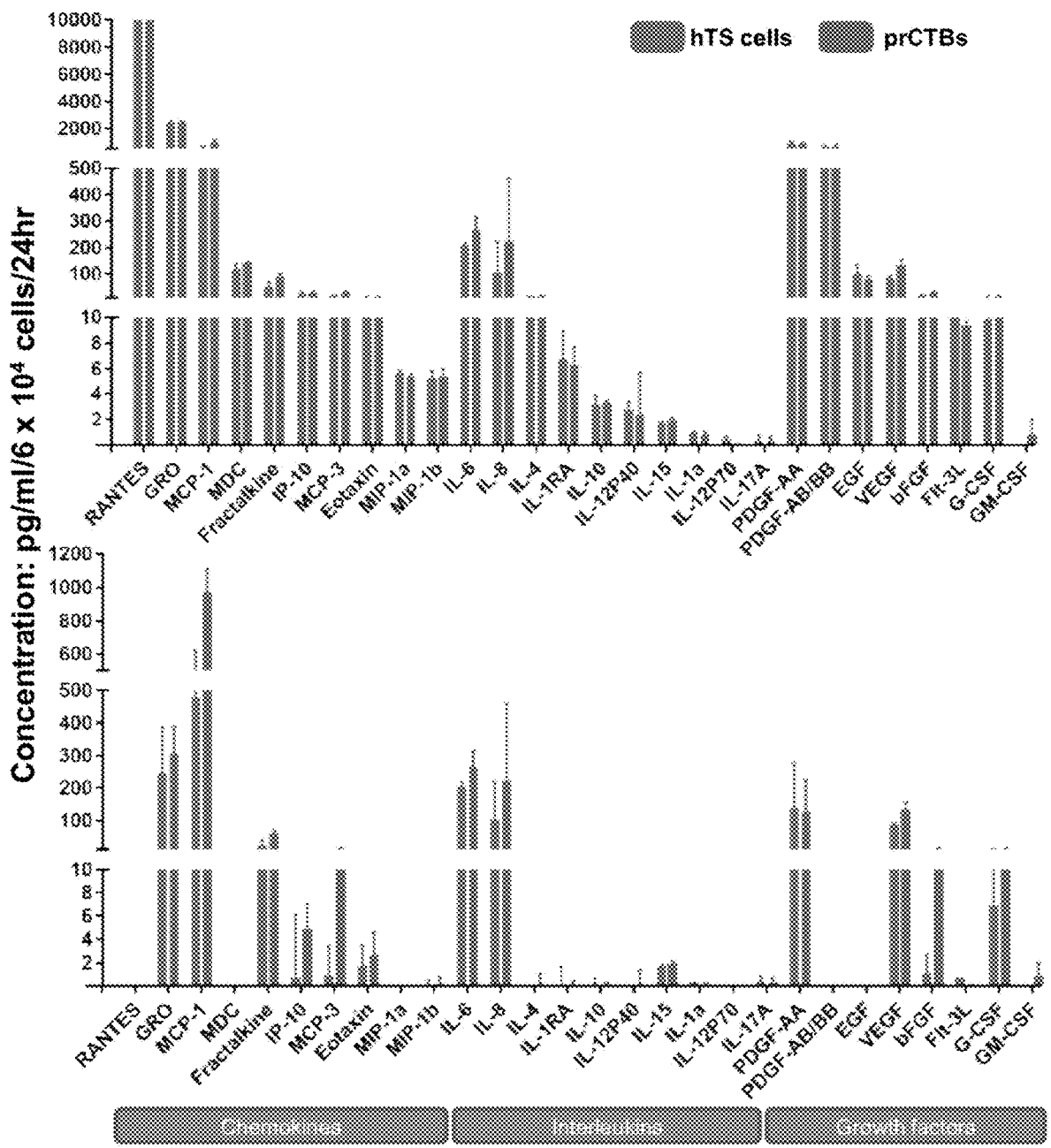
FIGS. 7A to 7Q are described herein.
Figure 7B:
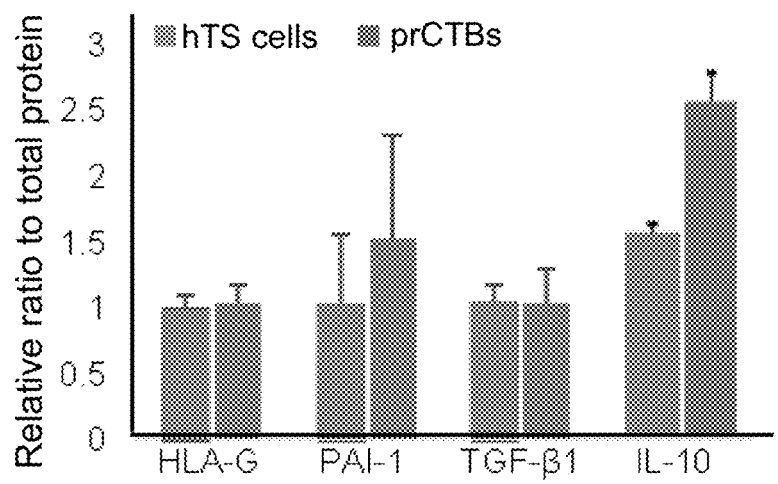
FIG. 7B shows immunoblotting assay results demonstrating the presence of numerous receptor molecules in hTS cells (the left) and prCTBs (the right).

Moreover, both hTS cells and prCTBs were able to release soluble human leukocyte antigen G (sHLA-G), transforming growth factor beta 1 (TGF-β1), plasminogen activator inhibitor-1 (PAI-1), and IL-10 by secretomic analysis (FIG. 7B).

Nevertheless, the commercial human platelet lysates (i.e., PLUS, Compass) used also secrete exosomes in culture media. By excluding the basal effects of PLUS, it was found that both naive hTS cells and prCTBs were actually able to secrete exosomes, including chemokines with mainly GRO, MCP-1, Fractalkine, IP-10, MCP-3, Eotaxin, and less amount of MIP-1β and; cytokines including IL-6 and IL-8 in accompany with less amount of IL-4, IL-1RA, IL-10, IL-12P40, IL-15, IL-1α, and IL-17A (FIG. 7A, lower panel). While the growth factors included PDGF-AA, VEGF, bFGF, and G-CSF as well as Flt-3L and GM-CSF in less amount (FIG. 7A, lower panel). These data suggested that both naive hTS cells and prCTBs can have abilities to release a variety of secretomes or exosomes for functions.

Figure 7C:
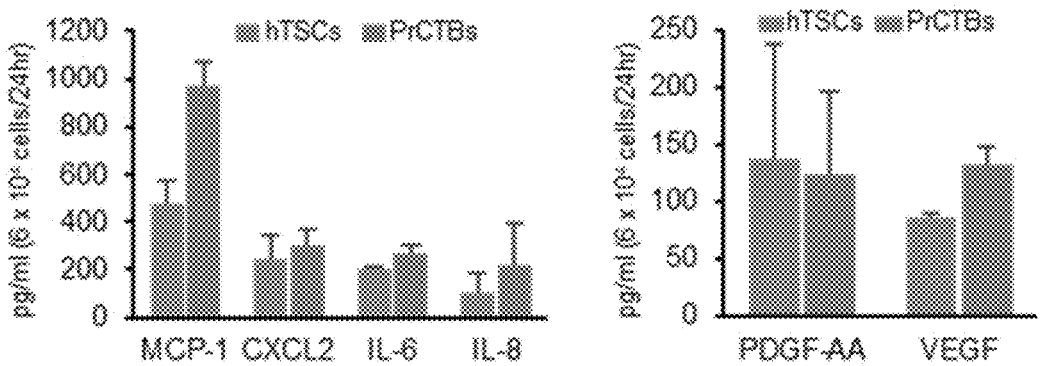
FIG. 7C shows secretomic assay results of proteins released from hTS cells and prCTBs by immunoblotting analysis. sHLA-G: soluble HLA-G. n=3.
Figure 7D:
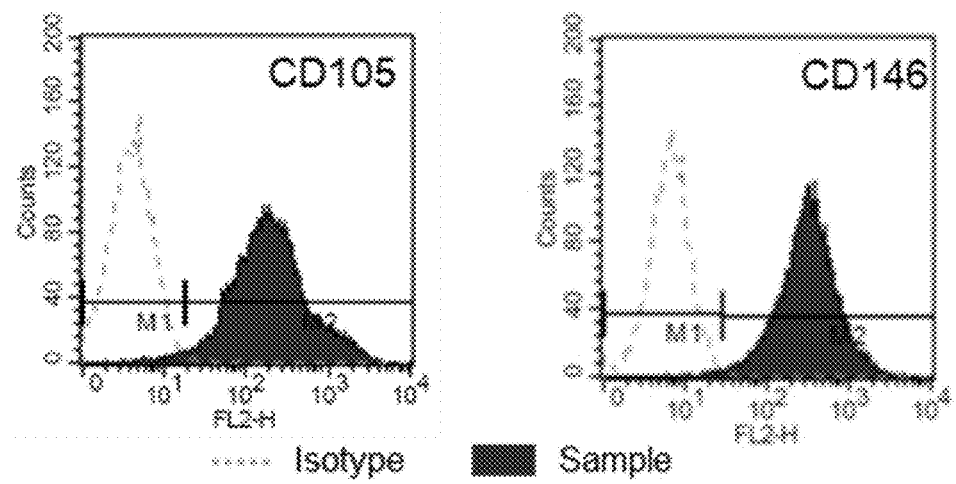
FIG. 7D shows that hTSCs express angiogenetic factors CD105 and CD146 by FACS analysis.

FIG. 7C shows another summary of production of cytokines IL-6 and IL-8; chemokines MCP-1 and CXCL2; and angiogenetic factors PDGF-AA and VEGF in both hTSCs and prCTBs. prCTBs expressed angiogentic molecules CD105 (Endoglin, a receptor for TGF-β to function in angiogenesis) and CD146 (vascular endothelial cadherin) (FIG. 7D). These results suggested that prCTBs have abilities to function in the decidual tissues at the feto-maternal interface.

Example 5 prCTBs Exhibit Immune Cell-Associated Biomarkers

Figure 9A:
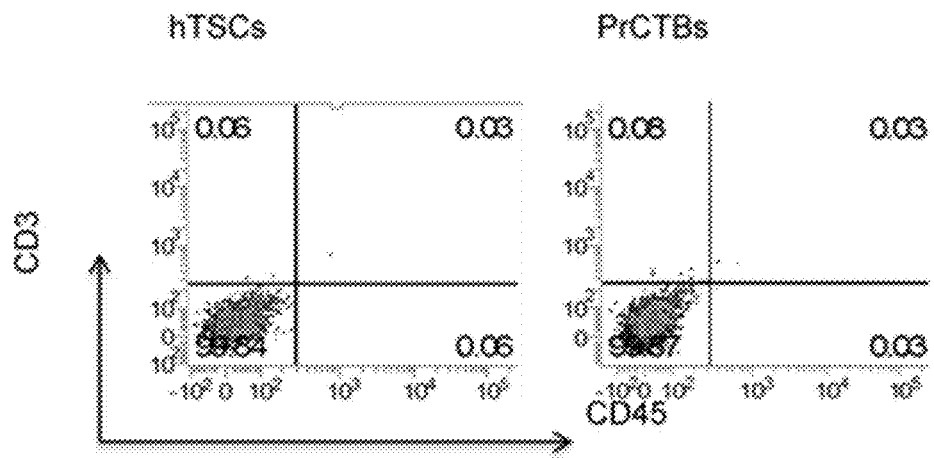
Figure 9B:
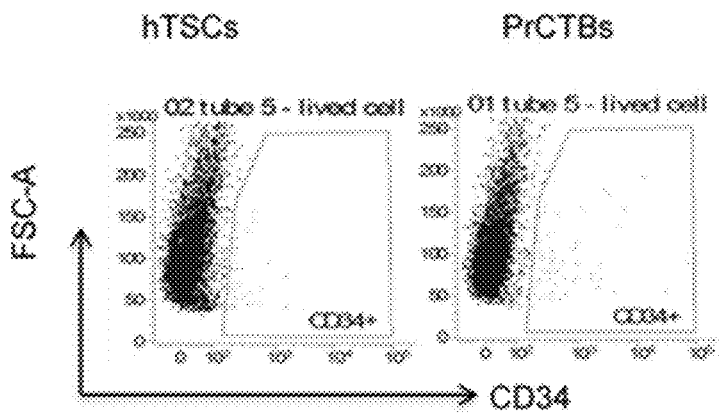
Figure 9C:
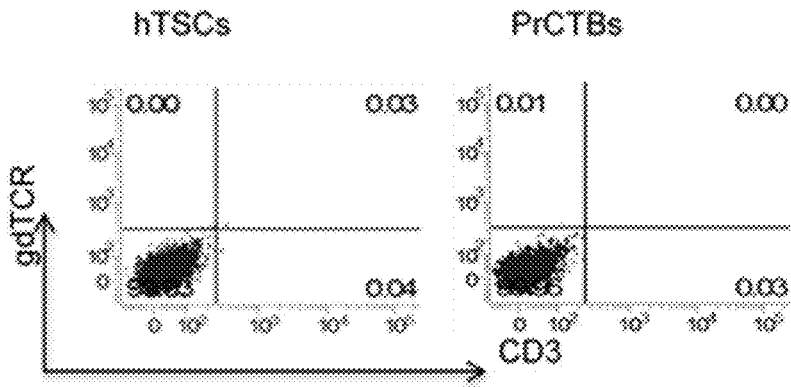
Figure 9D:
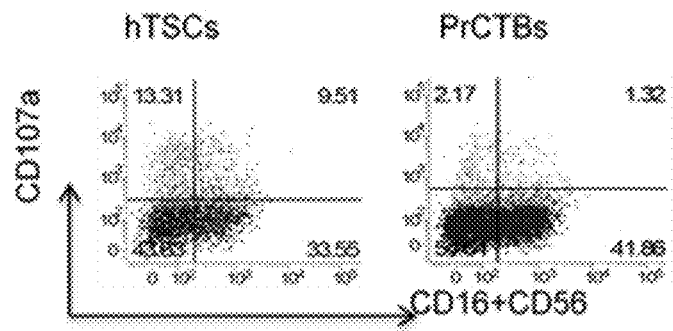
Figure 9E:
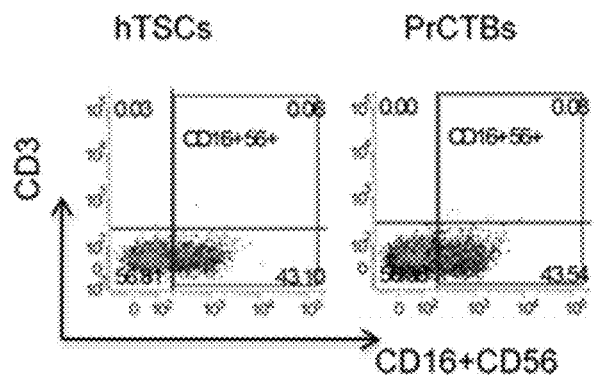
Figure 9F:
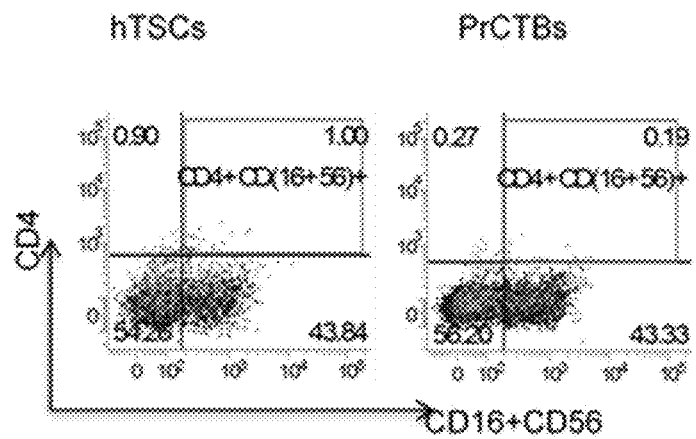
Figure 9G:
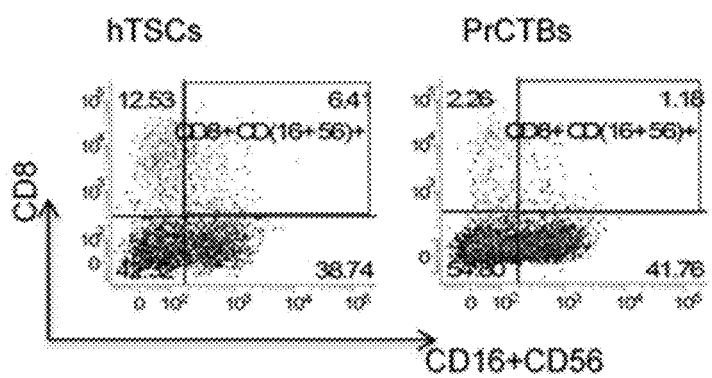
Figure 9H:
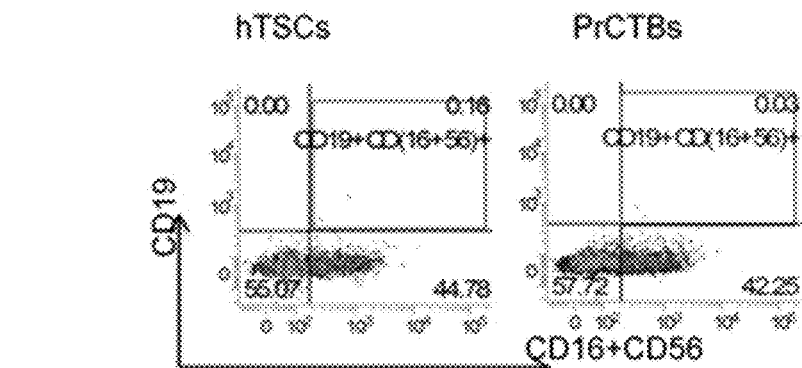
Figure 9I:
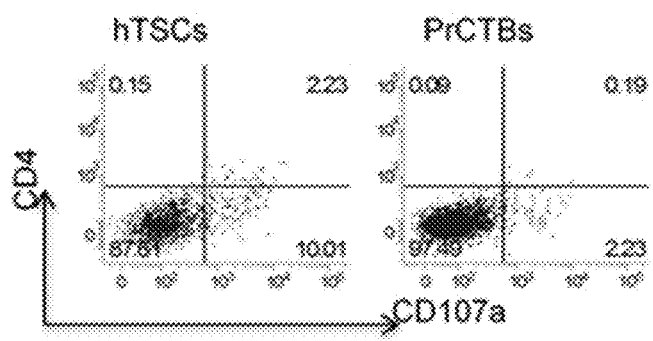
Figure 9J:
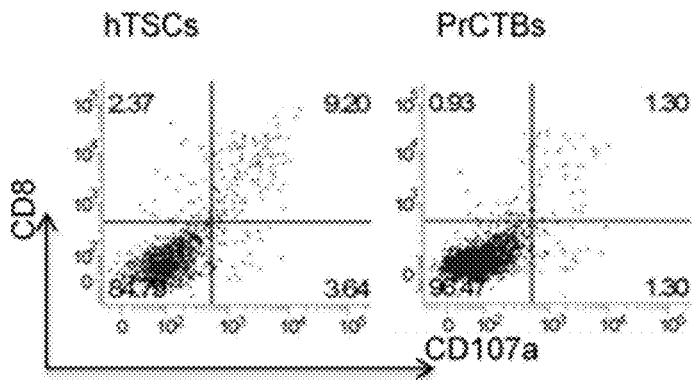
Figure 9K:
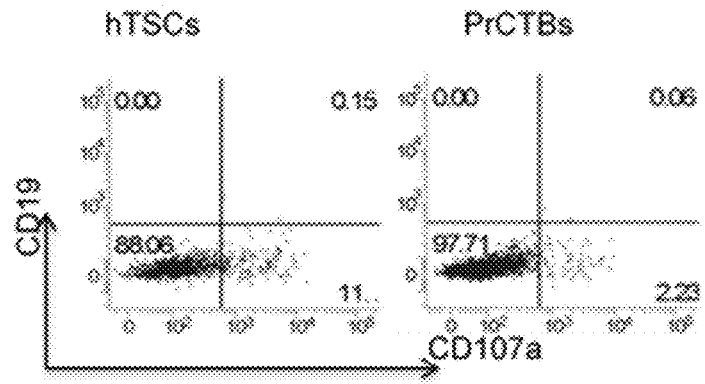

Expression of immune cell-associated biomarkers was examined in prCTBs with 8 independent cell lines by FACS analysis, showing a similar pattern of NK and T cell biomarkers. The results revealed that both of them expressed CD biomarkers, including CD4+, CD8+, CD107a+, and (CD16+CD56)+, sharing similar CD biomarkers with T cells and NK cells. A representative of cytometric analysis is shown in the table in FIG. 8 and FIGS. 9A-9M. (CD16+CD56)$^+$ cells and CD107(+) cells showed the highest expression in both hTSCs and prCTBs (FIGS. 8 and 9L). Their combinatory panels also occupied the most component of cell populations in distribution (FIGS. 8 and 9M). These results suggested that prCTBs have abilities to exert immune cell-like functions at the feto-maternal interface. It was also uncovered by immunostaining that prCTBs expressed CD11b and CD49f (FIG. 9N).

Figure 7E:
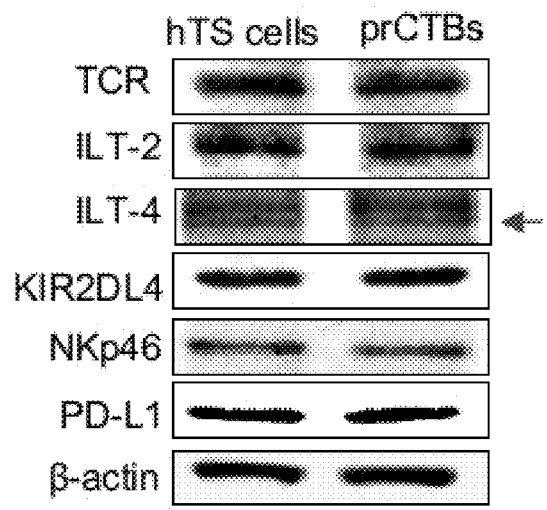
FIG. 7E shows immunoblotting assay results demonstrating the presence of numerous receptor molecules in hTS cells (the left) and prCTBs (the right).
Figure 7F:
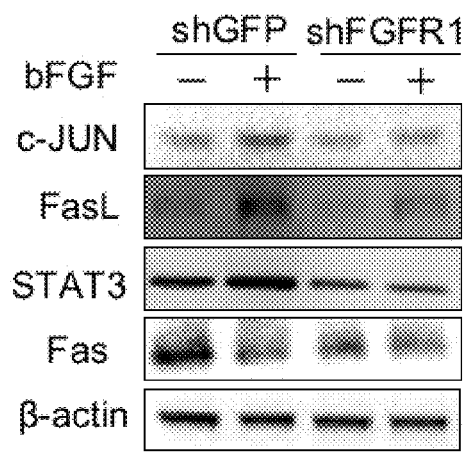
FIG. 7F shows that bFGF (10 ng/ml) induced upregulation of STAT3, c-JUN, and Fas ligand (FasL), but downregulation of Fas by immunoblotting assay. This action was inhibited by shFGFR1. shGFP was used as negative control.
Figure 7G:
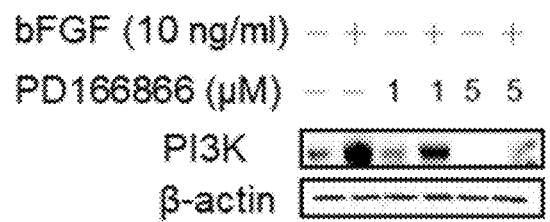
FIGS. 7G-7J show that bFGF (10 ng/ml) induced activation of CREB1 signaling by Western blot assay.
Figure 7H:
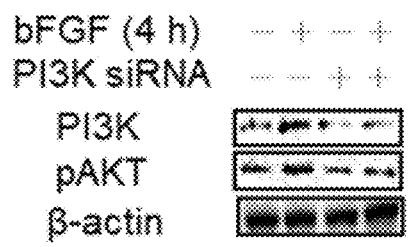
Figure 7I:
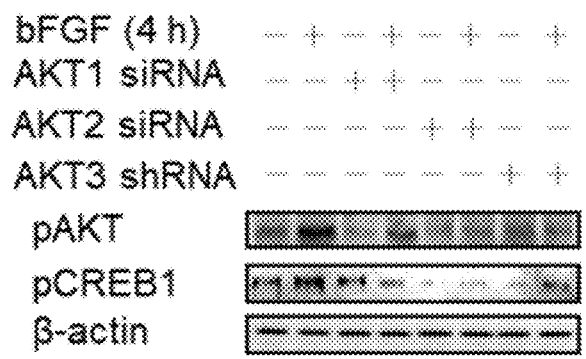
Figure 7J:
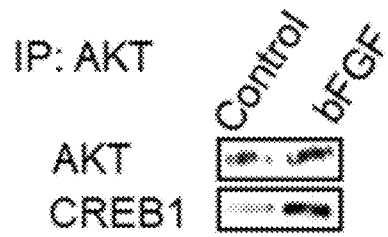

Furthermore, immunoblotting assay identified that both hTS cells and prCTBs expressed ILT-2 (leukocyte Ig-like receptor 1, also LILRB1), ILT-4 (also LILRB2), TCR (T cell receptor), and specifically, KIR2DL4 (killer cell Ig-like receptor) which is expressed by NK cells and subsets of CD8+ T cells to inhibit the cytolytic NK cell function (FIG. 7E). They also expressed PD-L1 (programmed death-ligand 1), Fas (apoptosis signal receptor, also APO-1), FasL (Fas ligand) which induces the apoptosis of infiltrating lymphocytes, and NKp46 (a major NK cell-activating receptor) (FIG. 7E), which are involved in the elimination of target cells Interestingly, bFGF activated the signal transducer and activator of transcription 3 (STAT3) and transcription factor c-JUN to consequently promote the expression of FasL in the differentiation of prCTBs (FIG. 7F). Knockdown of FGFR1 by shRNA confirmed this action. As a result, (CD16+CD56) molecule of prCTBs produced IFN-γ to stimulate PD-L1 production, thereby, recognizing cognate receptor PD-1 in tumor cells and down-regulating immune response against malignancy.

bFGF Induces IL-6 and IL-8 via FGFR1/CREB1 Signaling Pathway in prCTBs.

Figure 7K:
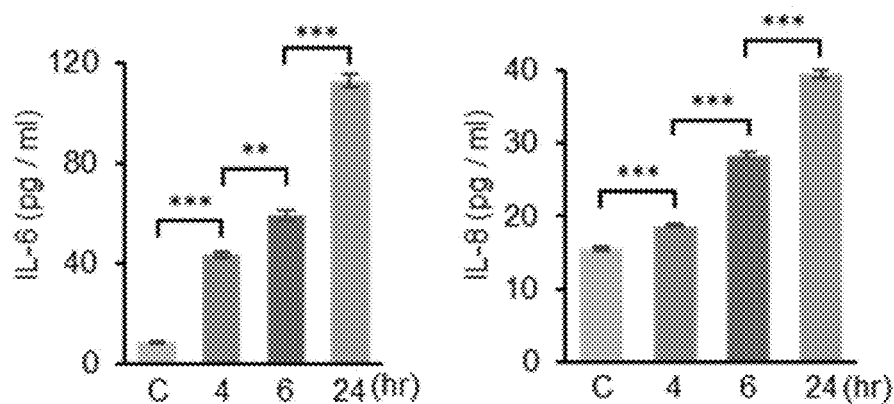
FIG. 7K shows that bFGF (10 ng/ml) induced IL-6 (left panel) and IL-8 (right panel) in a time-dependent manner. Data representing Mean±SD, n=3 independent cell lines, Student-t test: statistical significance: *$p<0.05$, $p<0.01$, *$p<0.001$.

To explore how prCTBs produce cytokines IL-6 and IL-8, hTSCs were incubated with bFGF for 1-day mimicking the transient stay in the fallopian tube. Mechanistically, bFGF activated its receptor FGFR1 at cell membrane to induce PI3K/phosphorylated (p)AKT signaling. In turn, pAKT interacted and phosphorylated downstream pCREB1 (cAMP responsive element binding protein 1) to activate pCREB1 signaling. These molecular processes were verified by using FGFR 1 inhibitor PD166866, and specific shRNAs for PI3K and pAKT (FIGS. 7G-7J). In the nucleus, CREB1 targeted the genes to produce IL-6 in a time-dependent manner (FIG. 7K, left panel) and IL-8 (FIG. 7K, right panel) in a dose-dependent manner, confirmed by ELISA assay (FIG. 7C). These molecular processes occurred co-incidentally with EMT in time and space. In conclusion, bFGF induces transformation of hTSCs into prCTBs and productions of IL-6 and IL-8 in prCTBs via an autocrine/paracrine fashion.

Figure 7L:
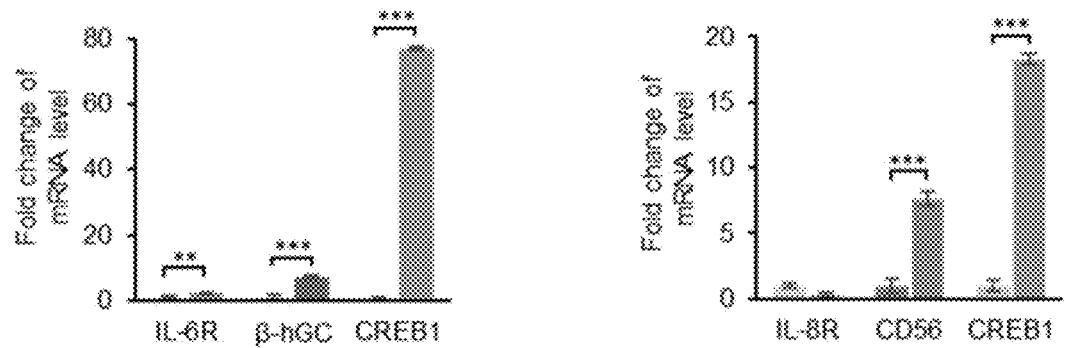
FIG. 7L shows RT-qPCR analysis showing that IL-6 (10 ng/ml) upregulated IL-6R mRNA, CREB1 mRNA, and β-hCG mRNA in hTSCs (left panel) and IL-8 (30 ng/ml) upregulates CREB1 mRNA and CD56 mRNA but not conventional receptor IL-8R (right panel). Data representing mean+/−SD, n=4, Student t-test, statistical significance $p<0.01$, *$p<0.001$.
Figure 7M:
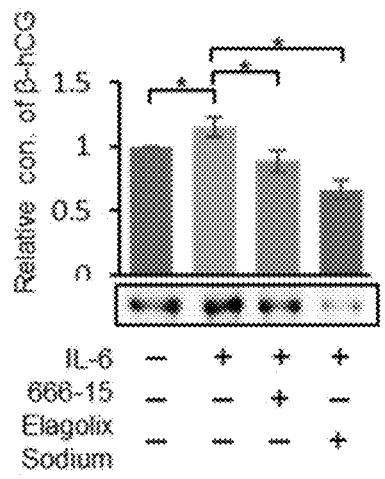
FIGS. 7M-7N show that IL-6 generated β-hCG(+)CD56(+) prCTBs by Western blot assay.
Figure 7N:
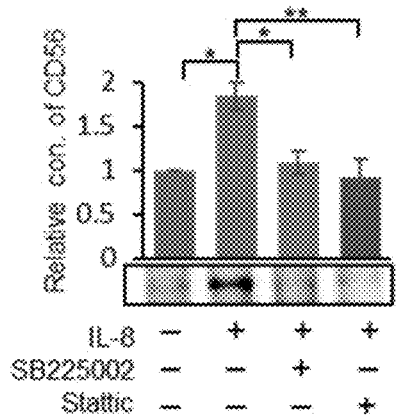

IL-6 Induces Trophoblast Marker β-hCG and IL-8 Induces NK Cell Marker CD56 in prCTBs In prCTBs, IL-6 bound to receptor IL-6R at the cell membrane to activate CREB1 signaling, resulting in the production of β-hCG by RT-qPCR assay (FIG. 7L, left panel). Interestingly, IL-6 enabled to bind another receptor GnRHR to co-incidentally activate CREB1 signaling to consequently produce β-hCG by Western blot assay (FIG. 7M). Meanwhile, IL-8 induced CD56 (also known as NCAM) production but did not through IL-8R by RT-qPCR assay (FIG. 7L, right panel). However, we uncovered that IL-8 enabled to alternatively bind another receptor CXCR2 to activate STAT3 (signal transducer and activator of transcription 3) signaling and in turn, to target genes for transcription to produce CD56 by Western blot assay (FIG. 7N). These molecular processes were verified by using GnRHR inhibitor Elagolix and CREB1 inhibitor 666-15 for β-hCG expression (FIG. 7L); while CXCR2 inhibitor SB225002 and STAT3 inhibitor Stattic were for CD56 expression (FIG. 7N). These results suggested that IL-6 induces trophoblast biomarker β-hCG; while IL-8 co-incidentally induces NK cell biomarker CD56 with an autocrine/paracrine fashion in prCTBs. To this end, we demonstrated that bFGF induces transformation of hTSCs towards prCTBs, resulting in unique β-hCG(+)CD56(+) prCTBs.

IL-8 Induce T Cell Marker CD4 via CXCR2/CREB1 Signaling in prCTBs

Figure 7O:
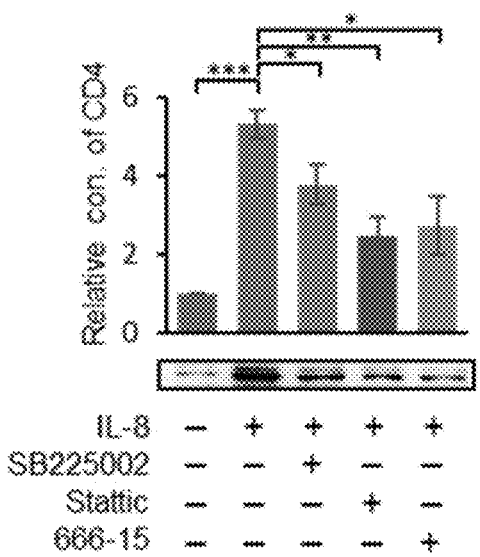
FIG. 7O shows that IL-8 (30 ng/ml) generated CD4(+) prCTBs via both CXCR2/CREB1 and CXCR2/STAT3 signaling pathways, inhibited by CREB1 inhibitor 666-15, CRCR2 inhibitor SB225002, and STAT3 inhibitor Stattic.
Figure 7P:
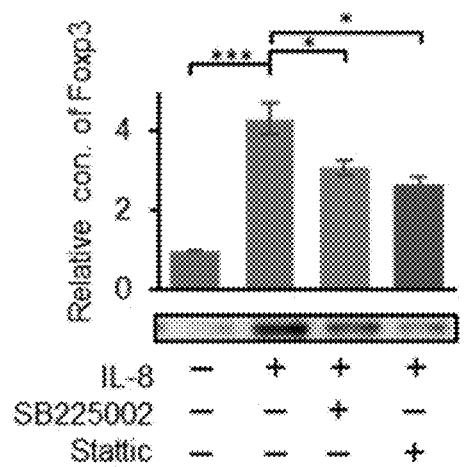
FIG. 7P shows that IL-8 (30 ng/ml) induced Foxp3 via CXCR2/STAT3 signaling pathway, inhibited by CRCR2 inhibitor SB225002 and STAT3 inhibitor Stattic (E). Data representing Mean±SD, n=3 independent cell lines, Student-t test: statistical significance *$p<0.05$, $p<0.01$, *$p<0.001$.

Simultaneously, IL-8 bound and activated receptor CXCR2 at the cell membrane of prCTBs via an autocrine/paracrine fashion to induce CREB1 signaling, allowing its nuclear translocation. In the nucleus, CREB1 targeted CD4 gene for transcription to produce CD4 molecule by Western blot assay (FIG. 7O). However, we uncovered that IL-8 was also able to bind the receptor CXCR2 to consequently activate STAT3 signaling, leading to nuclear translocation of STAT3. In the nucleus, STAT3 targeted at different sites of CD4 gene for transcription to produce CD4 (FIG. 7P). These molecular processes were verified by using CXCR2 inhibitor SB225002, CREB1 inhibitor 666-15, and STAT3 inhibitor Static (FIGS. 7O and 7P).

IL-8 Induces Foxp3 to Form CD4(+)Foxp3(+) Treg Cell-Like prCTBs

Figure 7Q:
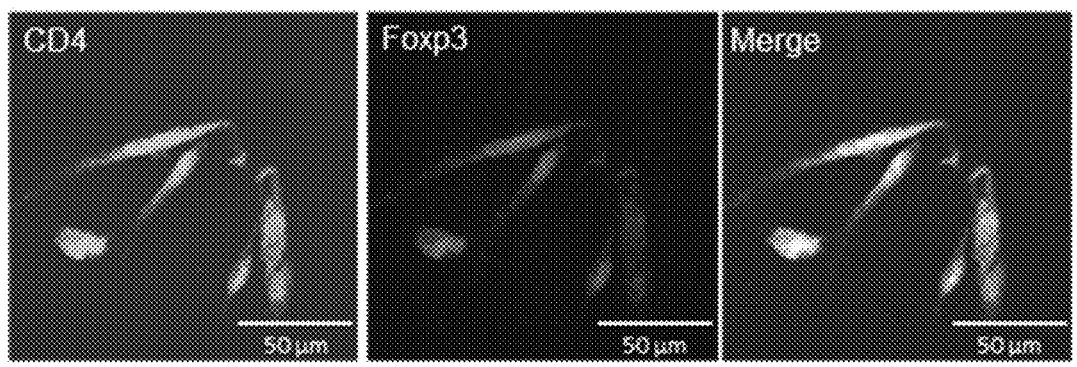

It was uncovered that the IL-8-induced CXCR2 signaling was able to bind to consequently activate STAT3 signaling for nuclear translocation of STAT3. In turn, STAT3 targeted at Foxp3 gene for transcription to produce Foxp3 proteins (also known as scurfin involved in immune system response) by Western blot analysis (FIG. 7P). These molecular processes were verified by using CXCR2 inhibitor SB225002 and STAT3 inhibitor Static (FIG. 7P). These results suggested that IL-8 produces CD4(+) and Foxp3(+) molecules in prCTBs, mimicking CD4(+)Foxp3(+) Treg cells Immunocytochemical co-staining of CD4(+)Foxp3(+) biomarkers was achieved in prCTBs (FIG. 7Q).

Example 6 prCTB Barrier at the Feto-Maternal Interface.

prCTBs Express Factors to Promote Angiogenesis in Decidual Tissues.

prCTBs were able to secrete VEGF and PDGF-AA by MILLIPLEX® assay (FIG. 7C) and plasminogen activator inhibitor-1 (PAI-1) and IL-10 by ELISA assay (FIG. 7B) as well as to express CD105(+) and CD146(+) markers by FACS analysis (FIG. 7D). All expressions of those molecules suggested that prCTBs have ability to promote angiogenesis and vasculogenesis, for example, in the SA remodeling of decidual tissues at the feto-maternal interface.

MCP-1 and CXCL2 Synergistically Drive Movement of prCTBs.

Figure 10A:
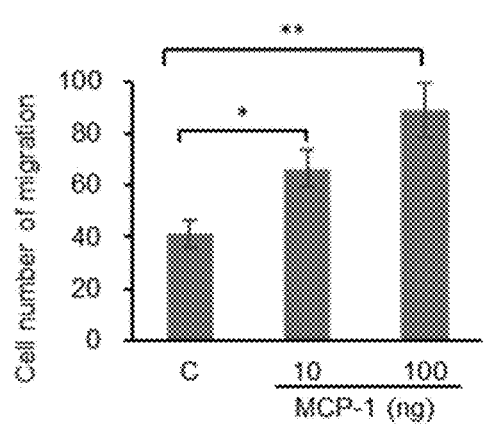
FIGS. 10A to 10K are described herein.
Figure 10B:
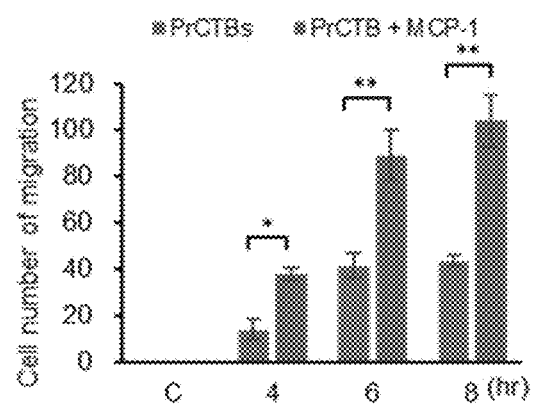
Figure 10C:
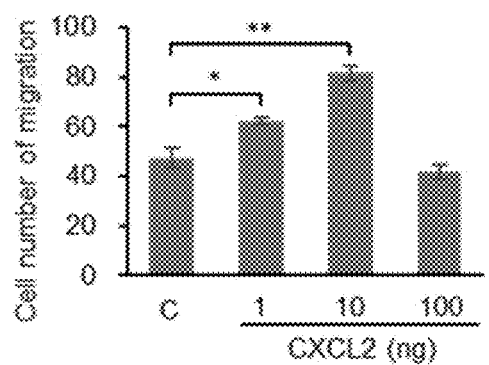
Figure 10D:
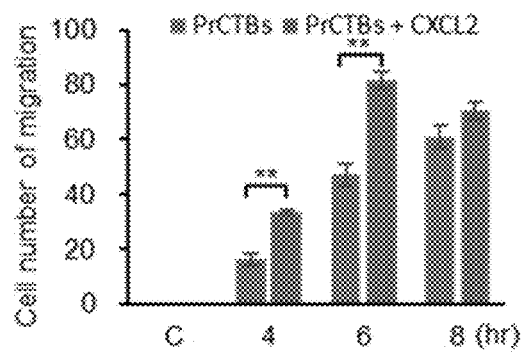

Transwell invasive and migration assay revealed that MCP-1 significantly induced invasion and migration of prCTBs in a dose-dependent manner (FIG. 10A) and in a time-dependent manner of both hTSCs and prCTBs (FIG. 10B). However, CXCL2 promoted cell migration also in a dose-dependent manner in prCTBs (FIG. 10C) and also in a time-dependent in both hTSCs and prCTBs (FIG. 10D). These results suggested that MCP-1 and CXCL2 have abilities to synergistically drive the movement of prCTBs in a time- and dose-dependent manner.

The Formation of Novel prCTB Barrier at the Feto-Maternal Interface.

Figure 10E:
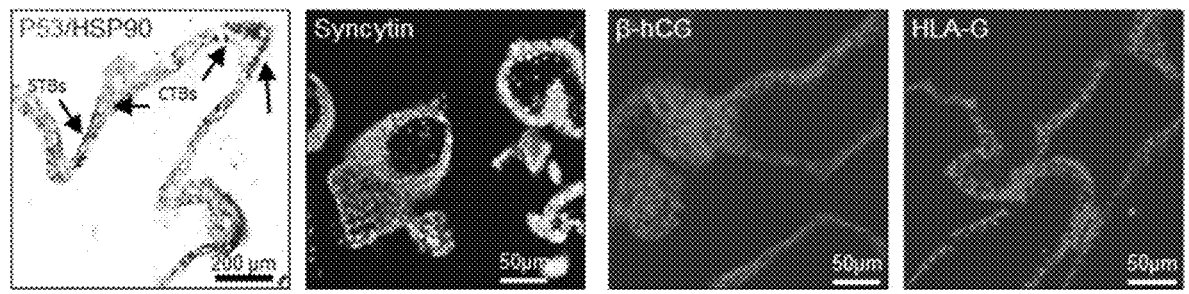
Figure 10F:
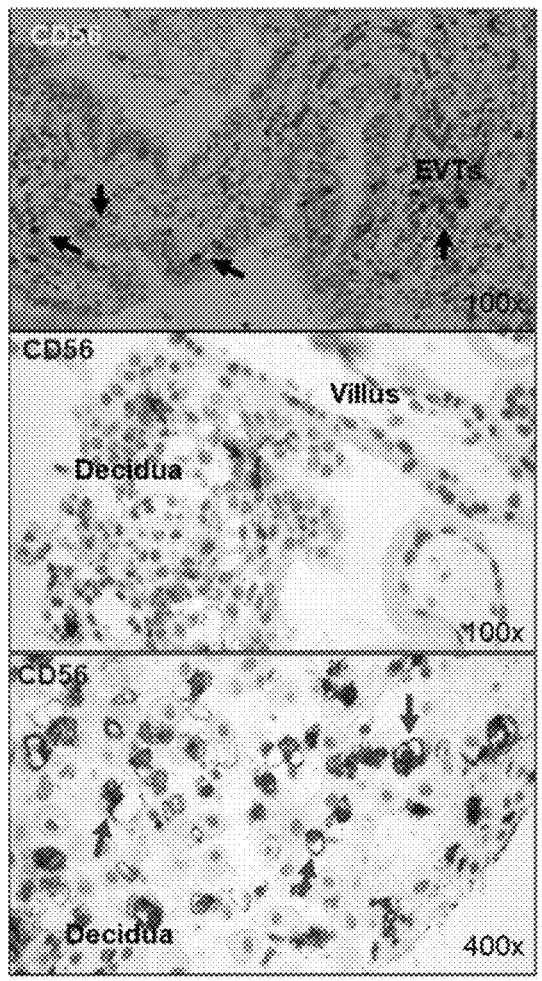

Immunohistochemical imaging revealed that prCTBs migrated towards EVTs with expression of Syncytin, p53, β-hCG, and HLA-G, while HSP90 appeared at the inner CTBs layer (FIG. 10E). At the feto-maternal interface, the CD56(+) prCTBs distributed sporadically at the villous stromal tissues with a trend moving to aggregate at the invasive EVTs by immunohistochemistry (FIG. 10F, upper and middle panels). These results suggested that prCTBs differentiate to EVTs that express Syncytin, p53, β-hCG, and HLA-G to synergistically invade into decidual epithelial cell layer of maternal deciduas for implantation.

Figure 10G:
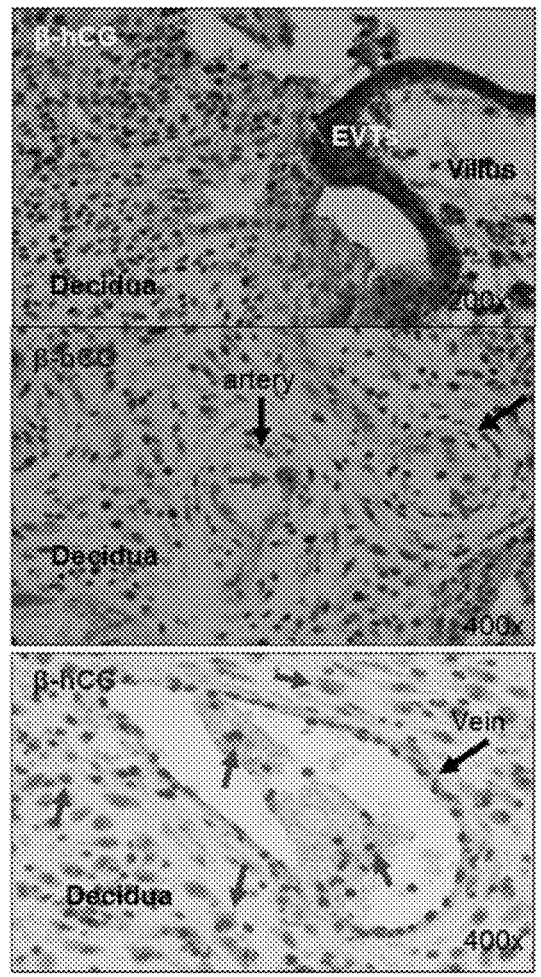
Figure 10H:
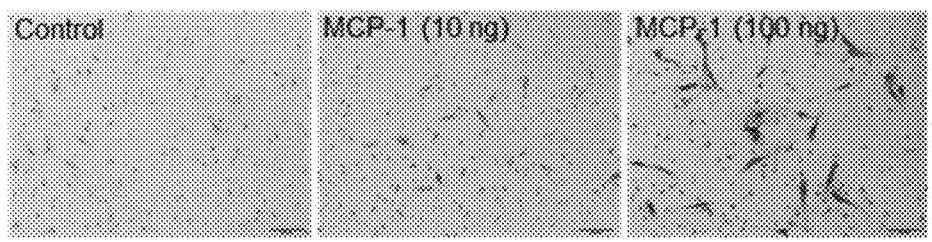
Figure 10I:
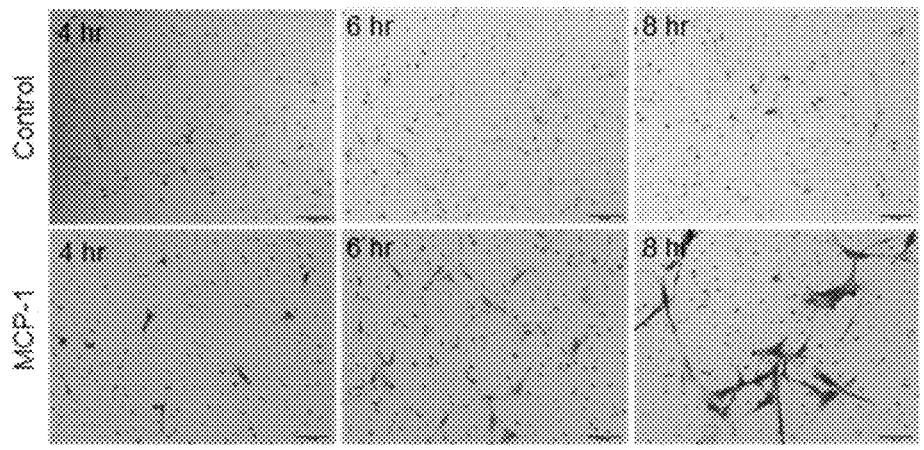
Figure 10J:
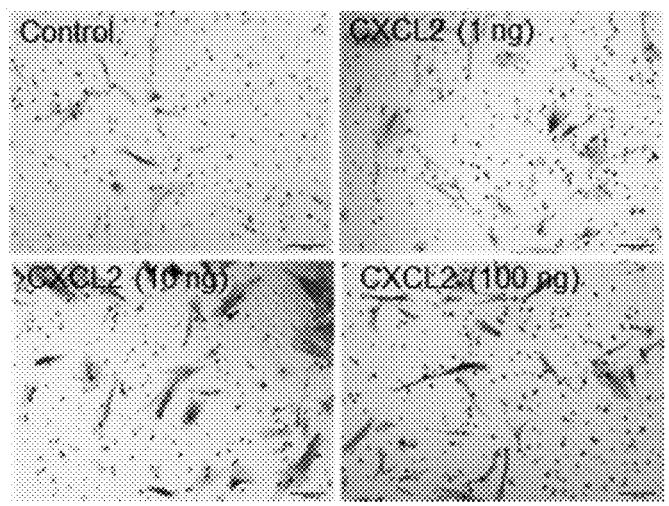
Figure 10K:
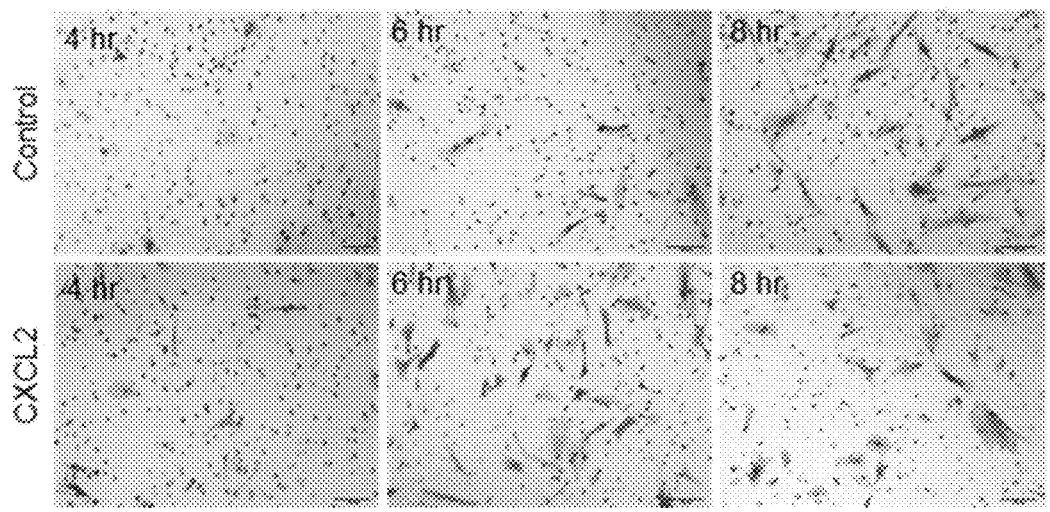

It was uncovered that both CD56(+) and β-hCG(+) prCTBs can be anchored and invaded into maternal deciduas (FIG. 10F, middle panel; FIG. 10G, upper panel). Through the invasion and migration, CD56(+) prCTBs occupied a large amount of cell components similar to the conventional decidual natural killer (dNK) cells in the decidual tissues (FIG. 10F, lower panel), while β-hCG(+) prCTBs behaved in a similar way (FIG. 10G, middle panel). It was uncovered that β-hCG(+) prCTB replaced the position of endothelial cell at arterial vessels (FIG. 10G, middle panel) and also appeared at the vessel cavity of vein (FIG. 10G, lower panel), suggesting a phenomena of SA remodeling and invasion of prCTBs into decidual vein as well. Eventually, plenty of CD56(+)β-hCG(+) prCTBs can accumulate at the decidual side to form a cellular barrier, which are called "prCTB barrier" here at the feto-maternal interface.

Example 7 prCTBs Induces Apoptosis of Solid Tumor Cells Upon Interaction.

Pancreatic Cancer Cells (PANC-1, CRL-1469)

Figure 11A:
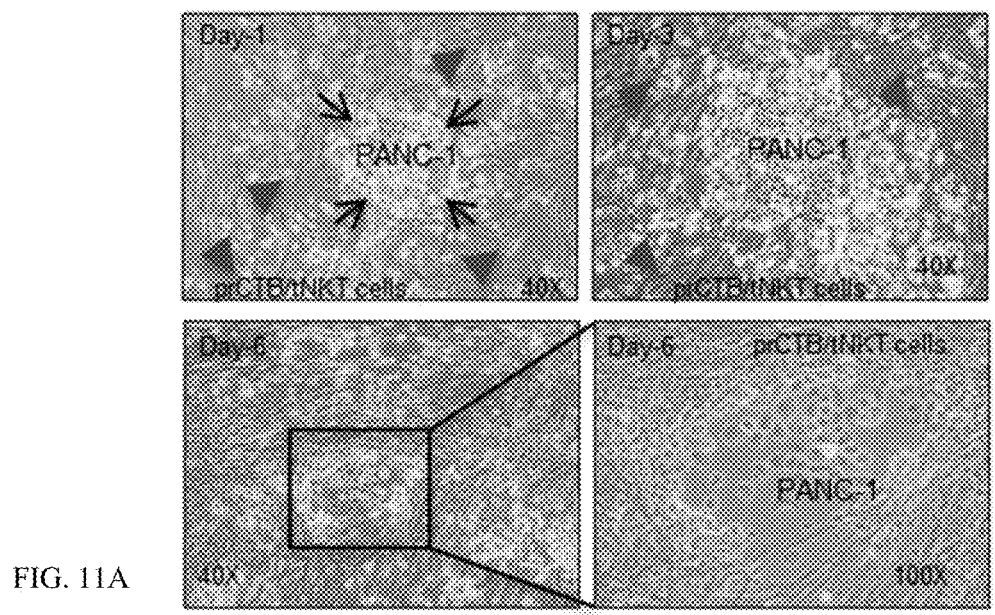
FIGS. 11A to 11K are described herein.
Figure 11B:
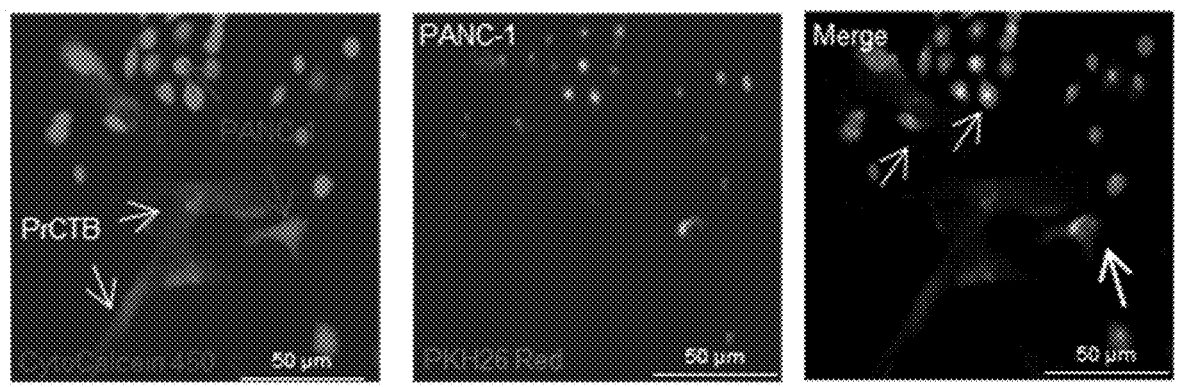
Figure 11C:
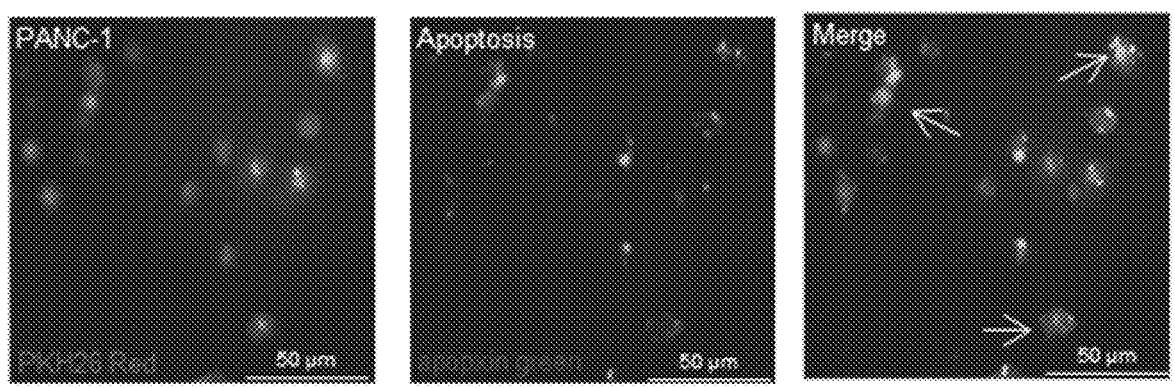
Figure 11D:
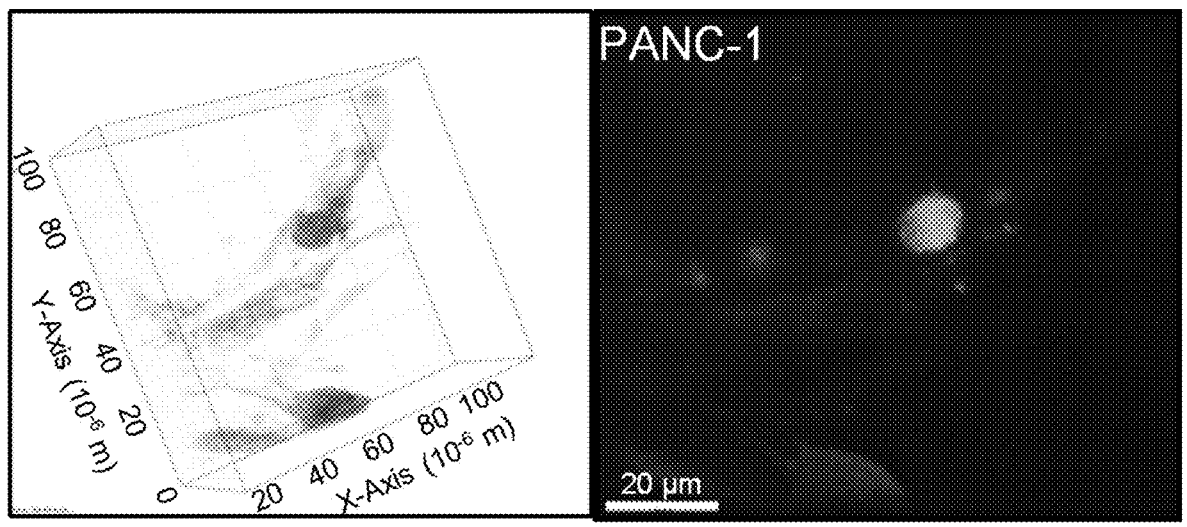

How pancreatic cancer cells (PANC-1) would interact with prCTBs was investigated. Co-culture of prCTBs and PANC-1 revealed that prCTBs enabled to migrate to encompass and infiltrate into the cellular colony of PANC-1, leading to the apoptosis of PANC-1 by light microscopy (FIG. 11A). This apoptotic phenomenon was further evidenced by using Apoptosis/Necrosis detection kit (blue, green, red) according to the manufacturer's instructions (ab176749, Abcam). FIG. 11B showed the interaction of two live cells, while FIG. 11C revealed the apoptosis of PANC-1 upon interaction. This interaction was further evidenced by 3D fluomicroscopy, showing the apoptosis of PANC-1 (FIG. 11D).

Figure 11E:
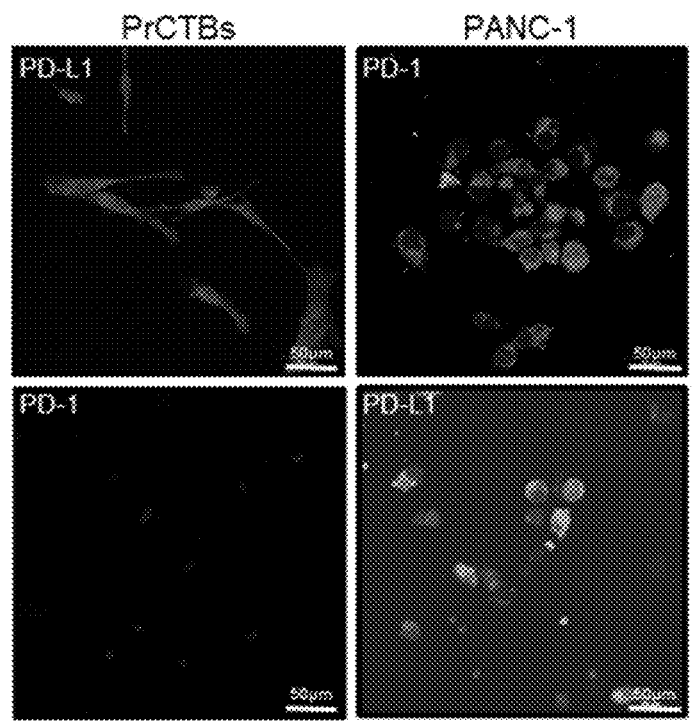
Figure 11F:
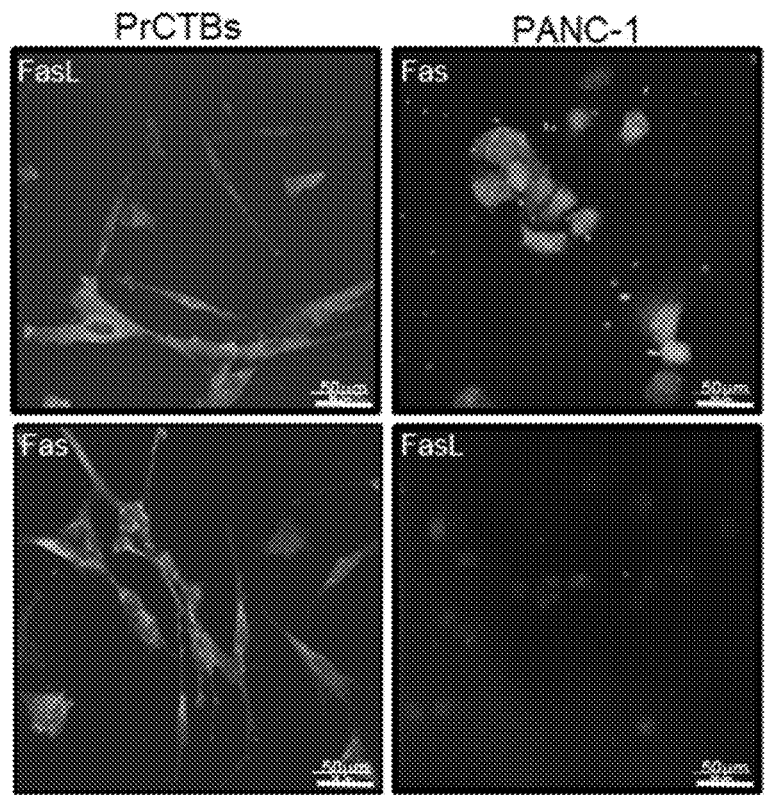

Mechanistically, it was uncovered that prCTBs expressed proteins PD-L1 (programmed cell death-ligand-1) but not PD-1 (programmed cell death protein 1) (FIG. 11E, left column), while PANC-1 expressed both PD-L1 and PD-1 (FIG. 11E, right column). This means that prCTBs enabled to deliver the PD-L1/PD-1 cell death signaling to the target PANC-1 cells, causing PANC-1 cell apoptosis. However, PANC-1 cell's PD-L-1 was unable to send the death signaling towards prCTBs because of the lack of PD-1 in prCTBs, explaining no apoptosis occurred in prCTBs. When we were dealing with the Fas/FasL cell death signaling pathway, we uncovered that prCTBs expressed both Fas ligand (FasL) and Fas (as FasL receptor), while PANC-1 expressed Fas but not FasL (FIG. 11F), thereby, prCTBs might deliver the apoptotic FasL/Fas signaling to target PANC-1, causing apoptosis of PANC-1. In contrast, prCTBs express Fas, but lack of FasL in PANC-1, suggesting no FasL/Fas cell death signaling would occur in prCTBs upon interaction.

Breast Cancer Cells (MCF-7, HTB22)

Figure 11G:
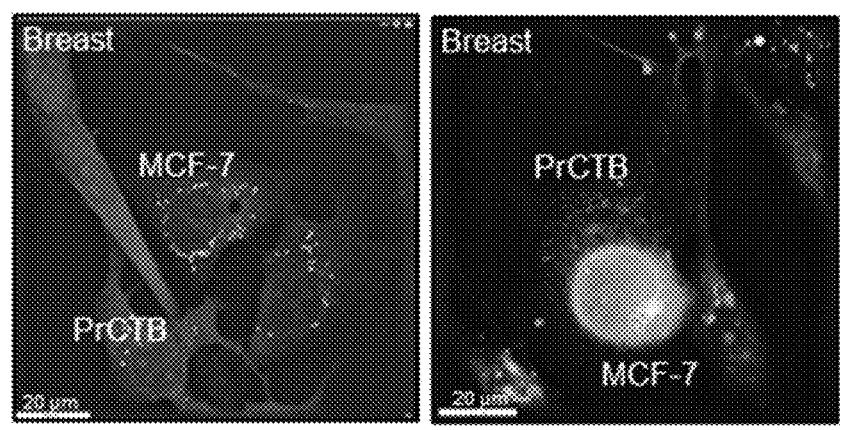
Figure 11H:
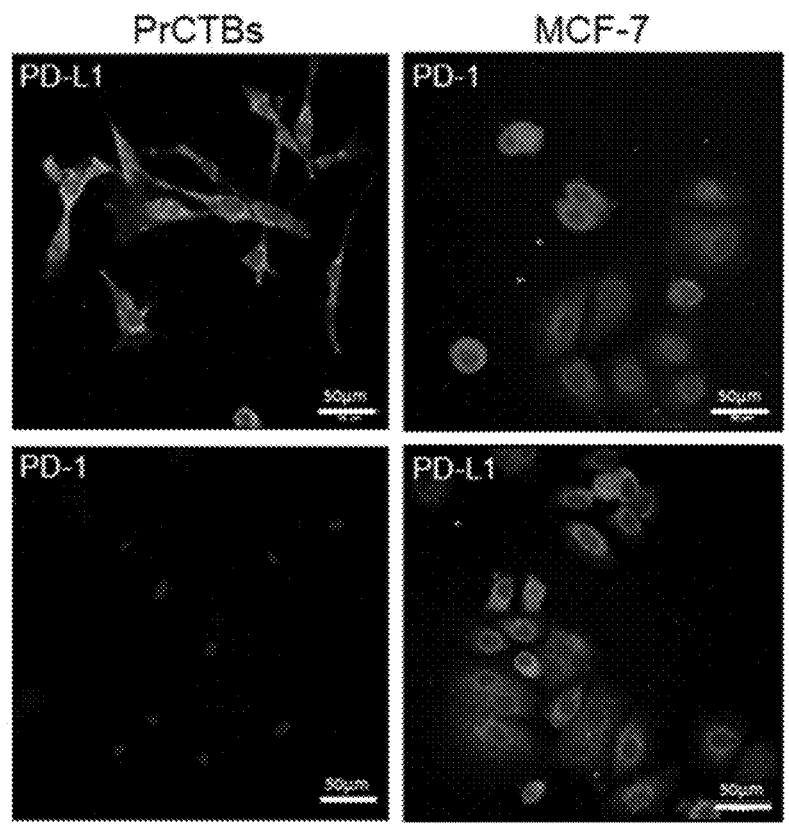

Co-culture of prCTBs with breast cancer cell line (MCF-7) revealed attraction and interaction, leading to the apoptosis of MCF-7 observed by 3D fluomicroscopy (FIG. 11G). prCTB-expressed PD-L1 would send a death signaling to its receptor PD-1 on the MCF-7 cells, resulting in an apoptotic response (FIG. 11H, upper panels). MCF-7 also expressed PD-L1, but prCTBs' lack of PD-1 receptor prevented any apoptosis (FIG. 11H, lower panels). However, when we examined the other FasL/Fas cell death axis, we uncovered that prCTBs expressed FasL while MCF-7 expressed Fas, allowing the occurrence of FasL/Fas death signaling in MCF-7 (FIG. 11I, upper panels).

prCTBs Contain Anti-apoptotic Proteins Bfl-1 and Mcl-1

Figure 11I:
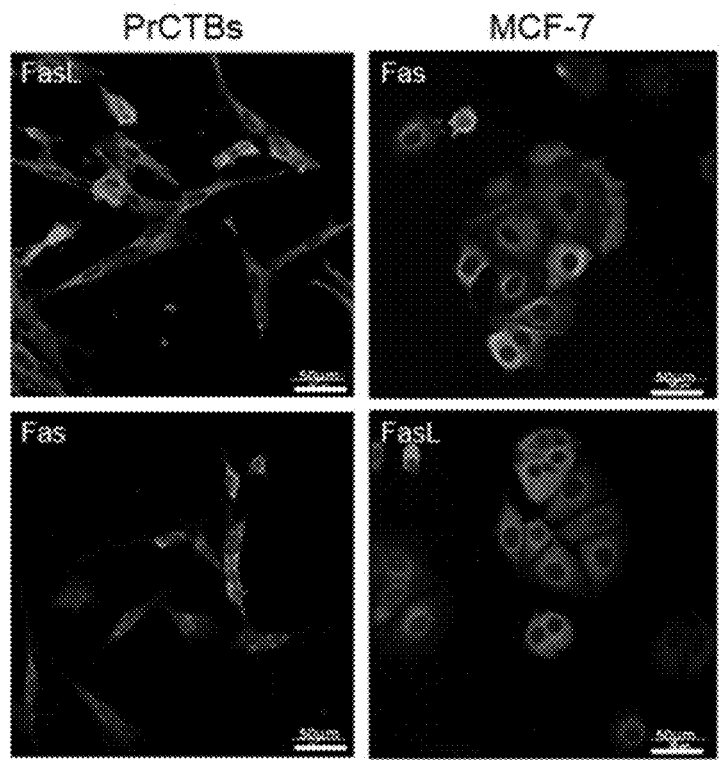
Figure 11J:
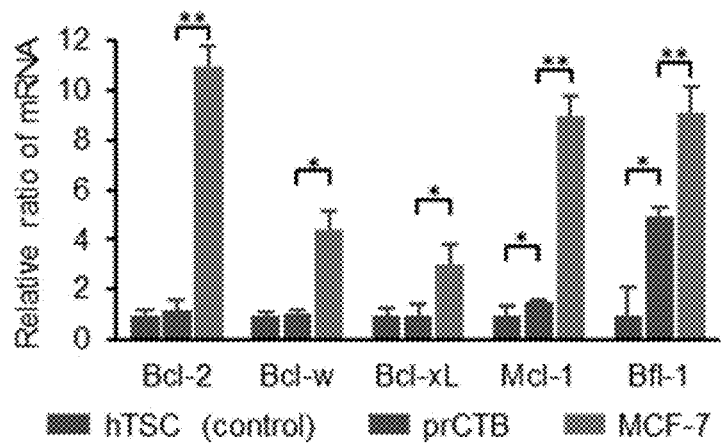

Interestingly, prCTBs expressed Fas while MCF-7 expressed FasL (FIG. 11I, lower panels). This fact implied that apoptosis might occur with prCTBs, but this was not the case. To explain that, we uncovered that prCTBs significantly expressed higher levels of anti-apoptotic Bfl-1 and Mcl-1 mRNAs in prCTBs by RT-qPCR analysis (FIG. 11J). Both Bfl-1 and Mcl-1, members of Bcl-2 family protein, contain anti-apoptotic abilities to avoid the death signaling of cancer cells, thereby, promoting cell survival.

Other Solid Tumor Cells

Figure 11K:
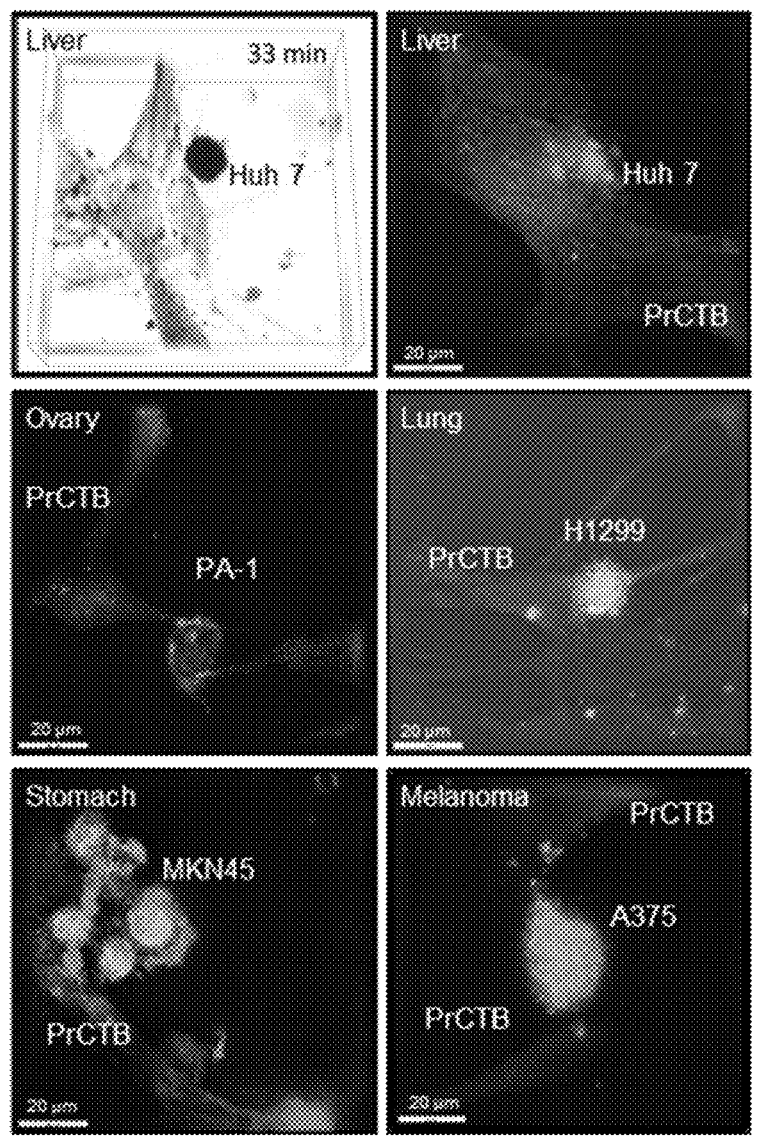

Accordingly, co-culture of prCTBs with a series of solid tumor cells was performed and detected by using the combination of immunocytochemistry and 3D fluomicroscopy. All solid tumor cells included liver Huh 7 cells, ovarian PA-1 (CRL-1572) cells, lung H1299 (CRL-5803) cells, stomach MNK45 (TCP-1008) cells, and melanoma A375 (CRL-1619) cells showed apoptosis during co-culture (FIG. 11K). These results suggested that prCTBs contain the capacity to eradicate a variety of solid tumor cells, depending on what cell death signaling pathways are involved.

Example 8

Similarities Between dNK Cells and prCTBs.

dNK cells in chorionic tissues were obtained from aborted women with medical reason and from ectopic pregnant woman at same gestational age of 8-weeks under consent. Firstly, it was confirmed the presence of CD56 biomarker in dNK cells (CD56 also expressed in prCTBs) by immunocytochemistry (FIG. 12A, top panels). Subsequently, immunohistochemistry in the chorionic villi revealed that sporadic CD56(+) dNK cells were visible among the inner layer villous CTBs and villous stroma, while accumulated at EVT areas (FIG. 12A, middle panel). β-hCG (+) dNK cells (β-hCG also expressed in prCTBs) were observed at the villous trophoblasts and accumulated in the EVT areas (FIG. 12A, right panels). In normal implantation, accumulated CD56(+) dNK cells and β-hCG(+) CTBs were found at the EVT areas and distributed sporadically at the nearby decidual tissues (FIG. 12B, left of upper and lower panels, respectively). Interestingly, large number of CD56(+) dNK cells and β-hCG(+) CTBs were expressed in maternal decidual tissues (FIG. 12B, left of upper and lower panels, respectively). Through the secretory exosomes, prCTBs like dNK cells would have the capacity to migrate into decidual tissues, communicate with decidual stromal cells, modulate with maternal immune system, and finally, complete implantation.

Example 9

Materials and Methods for Experiments Described in Examples 1-8.

Experimental Model and Subject Details.

Human trophoblast stem (hTS) cells were derived from trophoblast tissue. The trophoblast tissue was obtained from women who had suffered from the tubal ectopic pregnancy at 7-8 weeks' gestation with informed consent. This study was approved by the Institutional Review Board of KMUH. Naïve hTS cells were cultured and passaged in α-MEM (Thermo Fisher Scientific) supplemented with 10% (v/v) fetal bovine serum (FBS; SAFC Biosciences), at 37° C. in humidified air containing 5% CO2. Cultures were manually passaged at a 1:3-1:6 split ratio every 2-3 days. Low seeding densities and new culture media were tested for growing hTS cells, including 1) MesenCult™-ACF Plus medium, with MesenCult™-ACF PLUS 500x Supplement and L-Glutamine, with or without a substrate such as Cell Attachment Substrate, and 2) alpha-MEM containing nucleosides, GlutaMAX™ Supplement, and 10% Stemulate™ Human Platelet Lysate Cell Culture Media Supplement, with or without a substrate. For flow cytometric analysis of CD molecules, FBS was replaced by CMP grade PLUS (Compass Biochemical). The characteristic biomarkers, including HLA-G, β-hCG, and CDX2 with undetectable CD34 and CD45 were stably expressed. Induction of the hTSC cells to prCTBs was carried out by treatment with 10 ng/ml bFGF for 24 hr in hTS cells at passages 5-10. Several media for the induction were tested, including 1) MesenCult™-ACF Plus medium, with MesenCult™-ACF PLUS 500x Supplement and L-Glutamine, with or without a substrate such as Cell Attachment Substrate, and 2) alpha-MEM containing nucleosides, GlutaMAX™ Supplement, and 10% Stemulate™ Human Platelet Lysate Cell Culture Media Supplement, with or without a substrate. The seeding density was about 10,000 cells/cm$^2$. The culture was free from penicillin, streptomycin, mercaptoethanol, and/or nicotinamide. The culture can also be free from an animal component, serum such as fetal bovine serum, antibiotic, retinoic acid, dexamethasone, recombinant human oncostatin M, BMP4, and/or HGF. The regimen of differentiation was determined by empirical experience (data not shown). Stage-specific differentiation of lineages was referred to a variety of cellular biomarkers described previously. Cells were harvested at time as indicated for different analysis.

Transfection Experiment.

hTS cells were transfected with either siRNA or shRNA or 3' UTR reporter plasmids using TransIT-LT1 transfection reagent (Minis Bio LLC). Transfection was performed with 2 μg siRNA or shRNA plus 4 μl transfection reagent in 100 al OPTI-MEM (Gibco). After incubation for 10 min at room temperature, the transfection mix was gently added to cells overnight. The transfected cells then re-incubated with the α-MEM supplemented with 10% FBS for further treatment.

Plasmids Construction and Dual Luciferase Reporter Assay.

To construct the luciferase-3' UTR reporter plasmids, we amplified 3'UTR fragments from genomic DNA extract of hTS cells. The 3' UTR region was PCR amplified by using forward primer with a PsiI site and reverse primer with MfeI site for 3' UTR reporter construct were listed as followings: For Cdx2 3' UTR region: 5'-aaattataagctgtttgggttgttggtct-3' (SEQ ID NO: 1) and 5'-aaacaattgcccccataatttctgactgc-3' (SEQ ID NO: 2); For Smad4 3' UTR region 1: 5'-aaattataactcccaaagtgctgggatta-3' (SEQ ID NO: 3) and 5'-aaacaattgctgcactgttcacaggagga-3' (SEQ ID NO: 4); For Smad4 3' UTR region 2: 5'-aaattataacagtttgtcccagtgctgcta-3' (SEQ ID NO: 5) and 5'-aaacaattgatgacttgcccaaaggtcac-3' (SEQ ID NO: 6); For GSK3β 3' UTR region: 5'-aaattataacc-cacaactggggtaaaaga-3' (SEQ ID NO: 7) and 5'-aaacaattgctgtggaaggggcaaagata-3' (SEQ ID NO: 8). After combined PsiI and MfeI digested (NEB), the 3'UTR insert was subcloned to pGL4.51 plasmid (Promega) by using T4 DNA ligase (Takara).

For dual luciferase assays, firefly luciferase reporter (500 ng) or empty vector without any 3'UTR co-transfected with pGL4.74 vector, *Renilla* luciferase plasmid (500 ng, Promega), and non-specific control miRNA (30 pmol) or miR-124a precursor (30 pmol; System Biosciences) were co-transfected to hTS cells (1.5×10$^4$ cells in each well). Further 24 hr after transfection medium replacement, the luciferase activity was analyzed by dual luciferase reporter assay system (Promega) and Centro LB 960 Microplate Luminometer (Berthold Technologies). For evaluation, *Renilla* luciferase value was first normalized to the firefly luciferase activity and the calculated activity of each 3'UTR reporter was further normalized to that of the control vector. Data represented as mean±SD, n=8, p<0.05 as statistical significance. Whole cell extracts prepared in the cell lysis buffer were subjected to immunoblotting with CDX2, SMAD4, GSK3β, and β-actin antibodies.

Secretomic Analysis.

The hTS cell culture media (10 ml) were harvested at 80-90% confluence followed by centrifugation (3,000 rpm, 30 min, 4° C.). The supernatants were further concentrated to 1 ml by using 3 kDa VIVASPIN® concentrator (Sigma). The concentrated supernatant was further detected for TGF-β1, HLA-G, and PAI-1 by immunoblotting assay. IL-10 level was measured by OPTEIA® ELISA assay kit following the supplier's instructions (BD Pharmingen, San Diego). The range of detectable IL-10 concentration was between 2 and 2,000 pg/ml. An aliquot of 100 μl sample was measured in triplicate. Total protein of supernatant was measured by using Pierce BCA protein assay kit (Thermo Scientific). To measure C-peptide and insulin levels in glucose stimulation test, high glucose (20 mM) was added into α-MEM media (5 ml) at over 80% confluent cells after bFGF treatment. Media were collected at different time (5, 10, 20, 30, 60 and 120 min), freeze dried by lyophilizer (VirTis; Warminster), and rehydrated with sterile water (400 μl) for radioimmunoassay (RIA). C-peptide and insulin levels were determined by C-PEP II-RIA-CT (DIAsource ImmunoAssays S.A.) and Coat-A-Count insulin (Siemens Healthcare Diagnostics), respectively, in 5 assays.

Exosome Analysis.

Cell culture supernatants were harvested from: 1) the hTS cell culture (1×1.86 cells/10 ml) for 24 hr and 2) the bFGF (10 ng/ml)-treated hTS cells for 24 hr (prCTBs). These supernatants were subjected for MILLIPLEX® analysis at the National Experimental Research Laboratories, Taiwan using LUMINEX® LX 200 instrument (R&D system, USA) and data were analyzed by MILLIPLEX® analyst software (5.1.0.0.).

Transmission Electron Microscopy.

After high glucose stimulation, hTS cell-formed cellular cluster on the culture dish was dissected with wolfram needles. For transmission electron microscopy, the clumps of cells were fixed in 0.1 M PBS (Merck; pH 7.4) containing 3% (w/v) paraformaldehyde (Merck), 1.5% (w/v) glutaraldehyde (Merck) and 2.5% (w/v) saccharose (Merck) at room temperature for 1 hr at 4° C. overnight. The samples were washed with PBS before and after 2 hr of osmication at 4° C. in Palade's fixative containing 1% (v/v) OsO4, (Sigma), treated with uranyl acetate dihydrate (Merck), dehydrated through a graded series of ethanol solutions, and embedded using the EMBed-812 Embedding kit (Electron Microscopy Sciences). Ultrathin sections were stained with uranyl acetate dehydrate and lead citrate (Electron Microscopy Sciences), and examined using JEM-2000 EXII (JEOL, Tokyo).

Western Blots.

In cell culture, hTS cells were treated with bFGF and harvested at time as indicated and put into RIPA lysis solution (Millipore) supplemented with protease (Thermo Scientific) and phosphatase inhibitor (Cell Signaling Technology). After electrophoresis of 30 μg lysates on polyacrylamide gels, electroblotting onto PDVF membranes (Millipore) was performed. By blocking of 5% non-fat dry milk in PBS at room temperature (1 hr), target proteins were incubated with primary antibodies. All membranes were incubated with chemiluminescent (Millipore) and imaging was captured by the ChemiDoc XRS system (Bio-RAD). Antibodies used were listed in Key Resource Table. Data were analyzed by AlphaEaseFC (version 4.0.0).

Immunofluorescence Imaging.

For immunocytochemistry: Briefly, slide with cultured cells was fixed for 30 min at room temperature in 95% (v/v) ethanol, washed three times in PBS and incubated with blocking buffer PBS containing 0.05% (v/v) Tween 20 (PBST; Sigma) and 5% (v/v) normal donkey serum (MILLIPORE®) for 60 min. Primary and secondary antibodies were diluted in blocking buffer as indicated. Primary antibody was incubated at 4° C. overnight or 2 hr at room temperature. After incubation with specific primary antibody in blocking buffer, appropriate fluorescein isothiocyanate (FITC, Invitrogen) or Alexa Fluor 488, 594, 647 (Invitrogen) or DYLIGHT® 488, 594 (BioLegend) conjugated secondary antibody was added for 1 hr at room temperature. By nuclear counterstained with DAPI, slides were mounted with 50% glycerol. Images were captured by confocal laser scanning microscopy (LSM700; Zeiss Z1 or Olympus FLUOVIEW® 1000 confocal laser scanning microscope) or Countess II FL (Invitrogen), or 3D explorer-fluo microscopy (Nanolive, Swiss), or TissueFAXS system (TISSUEGNOSTICS® GmbH).

For immunohistochemistry: All procedures were performed on the Leica Bond-III automated system (Leica microsystems, Bannockburn). The staining utilized diaminobenzidine and hematoxylin from the Bond polymer refine kit (cat #DS9800, Leica). When the run was completed and the slide trays were removed, the covertiles were carefully lifted upward by the neck to remove. The slides were dehydrated through 2 changes each of 95% and 100% alcohol and 2 changes of xylene before coverslipping.

TAQMAN® miRNA and Quantitative Real-Time PCR Assay.

RNA was isolated from hTS cells in triplicate or quintuple samples using TRIZOL® reagent (Invitrogen) with DNAase I on-column digestion (Qiagen) according to manufacturer's protocol. Total RNA (500 ng) was used for reverse transcription with ISCRIPT™ cDNA synthesis kit (BIO-RAD®). PCR carried out in duplicate using ⅟₄₀th of the cDNA per reaction and 400 nM forward and reverse primers. For miRNA stem-loop qPCR, we used single tube TaqMan miRNA assays as manufacturer's instruction (Applied Biosystems). All RT reactions, including no-template controls and RT minus controls, were carried out in a GENEAMP® PCR 9700 Thermocycler (Applied Biosystems). Comparative real-time PCR was performed in triplicate or quintuple, including no-template controls, using specific primers for miR-124 or RNU6B (Applied Biosystems). U6 snRNA (RNU6B; Applied Biosystems) served as an endogenous control. Relative expression was calculated using SDS2.2.2 software (Applied Biosystems) was used for comparative $\Delta$Ct analysis.

Immunoprecipitation (IP) Assay.

Cell lysates of bFGF-treated hTS cells were collected. By incubation with protein G-agarose (MILLIPORE®) for 30 min, total protein (100 μg) was treated with specific primary antibodies listed in overnight. After treating with protein G-agarose beads for 2 h, the sample was washed three times with RIPA lysis buffer (MILLIPORE®), following by adding with protein loading dye and boiled for 5 min. The sample was resolved by 8% SDS-PAGE and subjected to immunoblotting analysis.

Chromatin Immunoprecipitation (ChIP) Assay.

ChIP assay was performed by using CHIP-IT® Express Chromatin Immunoprecipitation Kits (Active Motif) as manufacturer's instructions. Briefly, immunoprecipitated DNA fragments were extracted from hTS cells ($1\times10^6$). Antibody anti-CREB1 or anti-OCT4 or anti-β-catenin was used. Specific primers were used to amplify the conserved binding site at promoter regions of miR-124a or SOX17 or FOXA2 which was listed as followings: For promoter of miR124-2: forward, 5'-tctgcggctattggtttca-3' (SEQ ID NO: 9), and reverse, 5'-tctgccttcagcacaagagg-3' (SEQ ID NO: 10); and forward, 5'-gcggctctttggtttcaagg-3' (SEQ ID NO: 11); reverse, 5'-ctgccttcagcacaagagga-3' (SEQ ID NO: 12); For promoter of miR124-3: 5'-cccgcagttctcaaggacac-3' (SEQ ID NO: 13), and reverse, 5'-agaagggagccaggcaagtc-3' (SEQ ID NO: 14); for promoter of SOX17: 5'-ttgtagattgctctctctcctcc-3' (SEQ ID NO: 15), and reverse, 5'-gtgaagccttggctagggg-3' (SEQ ID NO: 16); For promoter of FOXA2: 5'-cccatcattgattcctggat-3' (SEQ ID NO: 17), and reverse, 5'-ttgggaggctgagatttgtc-3' (SEQ ID NO: 18).

Exosomes Analysis.

Cell culture supernatants were harvested from: 1) the hTS cell culture ($1\times1.8^6$ cells/10 ml) for 24 hr and 2) the bFGF (10 ng/ml)-treated hTS cells for 24 hr (prCTBs). These supernatants were subjected for MILLIPLEX® analysis at the National Experimental Research Laboratories, Taiwan using LUMINEX® LX 200 instrument (R&D system, USA) and data were analyzed by MILLIPLEX® analyst software (5.1.0.0.).

Flow Cytometry

For insulin analysis, hTS cells were collected by scraping or trypsinization with 1× TRYPLE® (Thermo Fisher Scientific) and washed with PBS. Cells ($5\times10^6$ cells/ml) were incubated in blocking buffer (PBST plus 5% donkey serum) on ice for 1 hr, followed by resuspension in blocking buffer with ALEXA FLUOR® 647 conjugated anti-insulin antibody (9008s, Cell signaling) or unconjugated anti-insulin antibody (sc-7839, Santa Cruz) at 4° C. for 30 min, Cells were washed twice in blocking buffer and strained with unconjugated antibody followed by incubation with blocking buffer with ALEXA FLUOR® 647 conjugated secondary antibodies on ice in dark for 30 min. After wash twice, cells were passed through polystyrene round-bottom tube with cell strainer cap (BD Falcon) before flow cytometry (LSR-II flow cytometer; BD Biosciences). Results were analyzed by FLOWJO® software.

For pluripotent transcription factor analysis, hTS cells were transfected with non-specific shRNA or shRNAs against CDX2 or OCT4 or SOX2 or NANOG. Cells (5×106 cells/ml) were then incubated with specific primary antibodies for 30 min. By incubation with the appropriate fluorescent dye-conjugated primary antibodies at adjusted dilution for 1 hr at 4° C., samples were washed and re-suspended in PBS, followed by passing through polystyrene round-bottom tube with cell strainer cap (BD Falcon) before flow cytometry (FACScan, BD Biosciences, San Jose, Calif.). The data were analyzed with Cell-Quest software (BD Biosciences).

For CD biomarkers analysis, hTS cells or prCTBs ($1×10^5$~$1×10^6$) were suspended in 240 µl of 1× FCM buffer (Leinco, F1175). Cells (30 µl) were stained with 7-AAD (BD, 5599257), fluorescence labeled antibodies (BD multi-test 6-Color TBNK (BD, 337166)+BV421-labeled anti-CD107a (BioLegend, 328625) or BV421-labeled anti-CD34 (BD, 562577) only or PerCP Cy5.5-labeled anti-CD45 (BD, 340952)+APC-labeled anti-CD3 (BD, 555342)+PE-labeled anti-γδTCR (BD, 340887) or fluorescence labeled isotype control antibodies (FITC-labeled IgG1κ (BD, 556649)+PE-labeled IgG (BD, 556650)+PE-labeled IgG2bκ (BD, 556656)+PerCP-Cy™5.5-labeled IgG1κ (BD, 552834)+PE-Cy™7-labeled IgG (BD, 557872)+APC-labeled IgG (BD, 550854)+APC-Cy7-labeled IgG1κ (BD, 557873)+BV421-labeled IgG (BD, 562438) or BV421-labeled IgG1κ (BD, 562438) only. After incubation for 15 minutes at room temperature, cells were washed with 1 ml of 1× FCM buffer and resuspended in 200 µl of 1× FCM buffer. Eventually, cell samples were analyzed by using FACSVerse flow cytometer (BD, 651155) and FACSuite software.

Apoptosis Assay

A variety of cancer cells (2,000 cells), including PANC-1 cells (pancreas), MCF-7 cells (breast), H1299 cells (lung), MKN45 cells (stomach), HepG2 cells (liver), PA-1 cells (ovary), A375 cells (melanoma), and PC-3 cells (prostate), were seeded and cultured with culture medium in the 35 mm glass bottom dish (IBIDI®; Cat #81158) at 5% CO2, 37° C. incubation. After cell adhesion overnight, bFGF-induced hTS cells ($2×10^4$ cells) were added for co-culture over 24 hr. For apoptosis assay, the co-cultured cells were stained by using the Apoptosis/Necrosis kit (ab176749, Abcam, Cambridge, England) according to the manufacture's instruction. Briefly, after removing the media, cells were washed twice by using assay buffer. By adding Apopxin green indicator (apoptotic cell/green color) and CytoCalcein 450 (health cell/blue color) for staining, cells were incubated at room temperature about 40 minutes. After wash twice with buffer, cells were observed under the 3D cell explorer-fluo (NANO-LIVE®, Swiss).

Co-culture of prCTBs and PANC-1 cells at ratio of 2:1 ($3×10^4$ cells/well) was performed in the 12-well plates at 37° C. for 6-days observed by light microscope. For apoptosis assay, the co-cultured cells (at 24 hr) were analyzed with the Apoptosis/Necrosis kit (ab176749, Abcam, Cambridge, England) according to the manufacture's instruction. After removing the media, cells were washed twice by using assay buffer. Then, each well added Apopxin green indicator (apoptotic cell) and CytoCalcein 450 (health cell) for incubation at room temperature for 60 minutes. Cells were washed with assay buffer and analyzed by fluorescence microscope.

Transwell Assays prCTBs ($1×10^6$ cells/nil) are seeded using the 6-well transwell insert (8 µm in pore size, CORNING®) and incubate for 10 minutes at 37° C. and 5% $CO_2$ to allow the cells to settle down. To do this, add extracellular matrix (ECM) materials on top of the transwell membrane and then add cells on top of the ECM. For example, MATRIGEL® is thawed and liquefied on ice, and then 30-50 µl of MATRIGEL® is added to a 24-well transwell insert and solidified in a 37° C. incubator for 15-30 minutes to form a thin gel layer. Cell solution is added on top of the MATRIGEL® coating to simulate invasion through the extracellular matrix. The transwell cell migration assay measures the chemotactic capability of cells toward a chemo-attractant. The transwell cell invasion assay, however, measures both cell chemotaxis and the invasion of cells through extracellular matrix, a process that is commonly found in cancer metastasis or embryonic development.

Using a pipette, very carefully add 600 µl of the desired chemo-attractant into the bottom of the lower chamber in a 24-well plate. Add the chemo-attractant without moving the transwell insert and avoid generating bubbles. Make sure the chemo-attractant liquid in the bottom well makes contact with the membrane in the upper well to form a chemotactic gradient. Incubation time is dependent on cell type and the chemo-attractant being used. Note: Further tests may be needed to determine the incubation period. Note: For adherent cells, the migrated cells will attach to the other side of the membrane[1,8]. The quantification of migrated cells can be performed following steps 2.4 to 2.8 (steps 2.4-2.8 do not need to be performed in a sterile environment). For non-adherent cells, the migrated cells will drop into the media in the lower chamber. The number of migrated cells can be counted by using hemocytometer or flow cytometer[5].

Remove the transwell insert from the plate. Use a cotton-tipped applicator as many times as needed to carefully remove the media and remaining cells that have not migrated from the top of the membrane without damaging it.

Add 600-1,000 µl of 70% ethanol into a well of a 24-well plate. Place the transwell insert into the 70% ethanol for 10 minutes to allow cell fixation. Remove transwell insert from the 24-well plate and use a cotton-tipped applicator to remove the remaining ethanol from the top of the membrane. Allow the transwell membrane to dry (typically 10-15 minutes).

Add 600-1,000 µl of 0.2% crystal violet into a well of a 24-well plate and position the membrane into it for staining. Incubate at room temperature for 5-10 minutes.

Gently remove the crystal violet from the top of the membrane with a pipette tip or cotton tipped applicator. Very carefully, to avoid washing off fixed cells, dip the membrane into distilled water as many times as needed to remove the excess crystal violet. Allow the transwell membrane to dry.

View underneath an inverted microscope and count the number of cells in different fields of view to get an average sum of cells that have migrated through the membrane toward the chemo-attractant and attached on the underside of the membrane.

Statistical Analysis.

Experiments in immunoblotting assay, qPCR assay, reporter assay, and insulin and IL-10 assays were conducted in triplicate or quadruple and repeated two times as indicated. p-value was calculated by Student's t test with two-tails distribution and $p<0.05$ was considered statistically significant.

One or more embodiments, instances, or aspects disclosed herein can be combined with any other embodiment(s), instance(s), or aspect(s) disclosed herein when suitable.

While some embodiments have been shown and described herein, such embodiments are provided by way of example only. Numerous variations, changes, and substitutions can occur without departing from the inventions. It should be understood that various alternatives to the embodiments of the inventions described herein can be employed in practicing the inventions.

What is claimed is:

1. A pharmaceutical composition that comprises an isolated precursory regulatory cytotrophoblast (prCTB) and a pharmaceutically acceptable excipient, wherein:
   (i) the prCTB expresses beta-hormone human chorionic gonadotropin (β-hCG), human leukocyte antigen G (HLA-G), CD56, insulin, heat shock protein 90 (HSP90), CD4, CD16, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof; and
   (ii) the prCTB expresses p53, Ki67, glutamate decarboxylase (GAD65), heat shock protein 70 (HSP70), soluble CD40-ligand (sCD40L), B cell leukemia/lymphoma 2 related protein A1 (BCL2A1 or Bfl-1), myeloid cell leukemia sequence 1 (Mcl-1), or any combination thereof,
   and wherein the prCTB lacks expression of programmed cell death protein 1 (PD-1).

2. The pharmaceutical composition of claim 1, wherein the prCTB expresses CD4, CD16, CD56, CD107a, CD8, or any combination thereof.

3. The pharmaceutical composition of claim 1, wherein the prCTB lacks expression of syncytin.

4. The pharmaceutical composition of claim 1, wherein the prCTB further expresses interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), B cell leukemia/lymphoma 2 related protein A1 (BCL2A1 or Bfl-1), myeloid cell leukemia sequence 1 (Mcl-1), beta-hormone human chorionic gonadotropin (β-hCG), soluble human leukocyte antigen G (sHLA-G), transformation growth factor β1 (TGF-β1), Plasminogen activator inhibitor-1 (PAI-1), interleukin 6 (IL-6), interleukin 8 (IL-8), interleukin 10 (IL-10), CD105, CD146, or any combination thereof.

5. The pharmaceutical composition of claim 1, wherein the prCTB is a human cell.

6. The pharmaceutical composition of claim 1, wherein the prCTB secretes a chemokine, a cytokine, a growth factor, or any combination thereof, or an exosome carrying any of the foregoing.

7. The pharmaceutical composition of claim 1, that comprises a population of cells, wherein the population of cells comprises a plurality of the prCTB.

8. The pharmaceutical composition of claim 7, wherein at least about 10% of the population of cells express CD16 and CD56.

9. The pharmaceutical composition of claim 7, wherein: at least about 2% of the population of cells express CD4; at least about 2% of the population of cells express CD8; at least about 5% of the population of cells express CD107; or any combination thereof.

10. The pharmaceutical composition of claim 7, wherein:
    at least about 10% of the population of cells express CD16 and CD56;
    at least about 2% of the population of cells express CD4;
    at least about 2% of the population of cells express CD8; and
    at least about 5% of the population of cells express CD107.

11. The pharmaceutical composition of claim 7, wherein at least about 2% of the population of cells express CD16, CD56, and CD107.

12. The pharmaceutical composition of claim 1, wherein the prCTB expresses the insulin, the HSP90, and the p53, and wherein the prCTB lacks expression of syncytin.

13. A genetically-engineered, isolated, precursory regulatory cytotrophoblast (prCTB), wherein:
    (i) the prCTB expresses beta-hormone human chorionic gonadotropin (β-hCG), human leukocyte antigen G (HLA-G), CD56, insulin, heat shock protein 90 (HSP90), CD4, CD16, CD107a, CD8, interleukin 15 (IL-15), leukocyte immunoglobulin-like receptor subfamily B member 1 (LILRB1), leukocyte immunoglobulin-like receptor subfamily B member 2 (LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof; and
    (ii) the prCTB expresses p53, Ki67, glutamate decarboxylase (GAD65), heat shock protein 70 (HSP70), soluble CD40-ligand (sCD40L), B cell leukemia/lymphoma 2 related protein A1 (BCL2A1 or Bfl-1), myeloid cell leukemia sequence 1 (Mcl-1), or any combination thereof,
    and wherein the prCTB lacks expression of programmed cell death protein 1 (PD-1).

14. The prCTB of claim 13, wherein the genetically engineered prCTB comprises a polynucleotide that encodes an exogenous protein that comprises a cellular receptor, an immunological checkpoint protein, a cytokine, a T cell receptor (TCR), a B cell receptor (BCR), a chimeric antigen receptor (CAR), or any combination thereof.

15. A method for treating a disease, comprising administering to a subject in need thereof an isolated precursory regulatory cytotrophoblast (prCTB), wherein:
    (i) the prCTB expresses beta-hormone human chorionic gonadotropin (β-hCG), human leukocyte antigen G (HLA-G), CD56, insulin, heat shock protein 90 (HSP90), CD4, CD16, CD107a, CD8, interleukin 15 (IL-15), leukocyte immunoglobulin-like receptor subfamily B member 1 (LILRB1), leukocyte immunoglobulin-like receptor subfamily B member 2

(LILRB2), T cell receptor (TCR), killer cell immunoglobulin-like receptor 2DL4 (KIR2DL4), programmed death-ligand 1 (PD-L1), apoptosis signal receptor (Fas), Fas Ligand (FasL), CD335 (NKp46), CD11b, CD49f, CD3, CD19, CD34, or any combination thereof; and (ii) the prCTB expresses p53, Ki67, glutamate decarboxylase (GAD65), heat shock protein 70 (HSP70), soluble CD40-ligand (sCD40L), B cell leukemia/lymphoma 2 related protein A1 (BCL2A1 or Bfl-1), myeloid cell leukemia sequence 1 (Mcl-1), or any combination thereof, and wherein the prCTB lacks expression of programmed cell death protein 1 (PD-1).

16. The method of claim 15, wherein the method down-regulates an inflammatory pathway in the subject.

17. The method of claim 15, wherein the disease comprises a cancer.

18. The method of claim 17, wherein the cancer comprises a solid tumor.

19. The method of claim 17, wherein the cancer comprises a pancreatic cancer, a breast cancer, a liver tumor, an ovarian tumor, a lung tumor, a stomach tumor, a melanoma, or any combination thereof.

20. The method of claim 15, wherein the disease involves a pathogen.

21. The method of claim 15, wherein the prCTB induces apoptosis of a cancer cell.

22. The method of claim 21, wherein the prCTB itself does not undergo apoptosis from contacting the cancer cell.

23. The method of claim 15, wherein the prCTB expresses the insulin, the HSP90, and the p53, and wherein the prCTB lacks expression of syncytin.

* * * * *